(12) United States Patent
Mason et al.

(10) Patent No.: US 11,325,005 B2
(45) Date of Patent: May 10, 2022

(54) SYSTEMS AND METHODS FOR USING MACHINE LEARNING TO CONTROL AN ELECTROMECHANICAL DEVICE USED FOR PREHABILITATION, REHABILITATION, AND/OR EXERCISE

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM TECHNOLOGIES, INC., Brookfield, CT (US)

( * ) Notice: Subject to any disclaimer, the term of this patent is extended or adjusted under 35 U.S.C. 154(b) by 0 days.

(21) Appl. No.: 17/150,938

(22) Filed: Jan. 15, 2021

(65) Prior Publication Data
US 2021/0138304 A1 May 13, 2021

Related U.S. Application Data

(63) Continuation-in-part of application No. 17/021,895, filed on Sep. 15, 2020, now Pat. No. 11,071,597.
(Continued)

(51) Int. Cl.
*A63B 24/00* (2006.01)
*A63B 21/005* (2006.01)
(Continued)

(52) U.S. Cl.
CPC ...... *A63B 24/0075* (2013.01); *A63B 21/0058* (2013.01); *A63B 24/0062* (2013.01);
(Continued)

(58) Field of Classification Search
CPC ........ A61B 2034/105; A61B 2034/258; A61B 34/10; A61B 34/25; A61B 2022/0094;
(Continued)

(56) References Cited

U.S. PATENT DOCUMENTS

| 59,915 A | 11/1866 | Lallement |
|---|---|---|
| 363,522 A | 5/1887 | Knous |

(Continued)

FOREIGN PATENT DOCUMENTS

| CA | 2698078 A1 | 3/2010 |
|---|---|---|
| CN | 112603295 A | 2/2003 |

(Continued)

OTHER PUBLICATIONS

International Searching Authority, Search Report and Written Opinion for International Application No. PCT/US2021/038617, dated Oct. 15, 2021, 12 pages.
(Continued)

*Primary Examiner* — George Manuel
(74) *Attorney, Agent, or Firm* — Dickinson Wright, PLLC; Stephen A. Mason; Jonathan H. Harder

(57) ABSTRACT

Systems, methods, and computer-readable mediums for operating an electromechanical device are disclosed. The system includes, in one example, the electromechanical device, a patient portal, and a computing device. The computing device is configured to receive user data relating to a user, and receive treatment data relating to treatment plans and outcomes. The computing device is also configured to generate a prehabilitation plan by using a machine learning model to process the user data and the treatment data. The
(Continued)

computing device is further configured to select, for the electromechanical device, an electromechanical device configuration that enables exercises of the prehabilitation plan to be performed by the user such that performance improves an area of the user's body. The computing device is also configured to enable the electromechanical device to implement the electromechanical device configuration.

30 Claims, 45 Drawing Sheets

Related U.S. Application Data

(60) Provisional application No. 62/910,232, filed on Oct. 3, 2019, provisional application No. 63/066,488, filed on Aug. 17, 2020.

(51) Int. Cl.
*G16H 20/30* (2018.01)
*G06N 20/00* (2019.01)
*G16H 10/60* (2018.01)
*A63B 22/00* (2006.01)
*A63B 22/06* (2006.01)

(52) U.S. Cl.
CPC ............. *G06N 20/00* (2019.01); *G16H 10/60* (2018.01); *G16H 20/30* (2018.01); *A63B 22/0605* (2013.01); *A63B 2022/0094* (2013.01); *A63B 2024/0093* (2013.01)

(58) Field of Classification Search
CPC ........ A61B 2024/0093; A61B 21/0058; A61B 22/0605; A61B 24/0062; A61B 24/0075; G06N 20/00; G16H 10/60; G16H 20/30; G16H 40/67
See application file for complete search history.

(56) References Cited

U.S. PATENT DOCUMENTS

| | | |
|---|---|---|
| 446,671 A | 2/1891 | Elliott |
| 610,157 A | 8/1898 | Campbell |
| 631,276 A | 8/1899 | Bulova |
| 823,712 A | 6/1906 | Uhlmann |
| 1,149,029 A | 8/1915 | Clark |
| 1,227,743 A | 5/1917 | Burgedorfp |
| 1,784,230 A | 12/1930 | Freeman |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,606,241 A | 8/1986 | Fredriksson |
| 4,611,807 A | 9/1986 | Castillo |
| 4,616,823 A | 10/1986 | Yang |
| 4,648,287 A | 3/1987 | Preskitt |
| 4,673,178 A | 6/1987 | Dwight |
| 4,824,104 A | 4/1989 | Bloch |
| 4,850,245 A | 7/1989 | Feamster et al. |
| 4,858,942 A | 8/1989 | Rodriguez |
| 4,869,497 A | 9/1989 | Stewart et al. |
| 4,915,374 A | 4/1990 | Watkins |
| 4,930,768 A | 6/1990 | Lapcevic |
| 4,961,570 A | 10/1990 | Chang |
| 5,161,430 A | 11/1992 | Febey |
| 5,202,794 A | 4/1993 | Schnee et al. |
| 5,247,853 A | 9/1993 | Dalebout |
| 5,282,748 A | 2/1994 | Little |
| 5,316,532 A | 5/1994 | Butler |
| 5,324,241 A | 6/1994 | Artigues et al. |
| 5,336,147 A | 8/1994 | Sweeney, III |
| 5,338,272 A | 8/1994 | Sweeney, III |
| 5,361,649 A | 11/1994 | Slocum, Jr. |
| D353,421 S | 12/1994 | Gallivan |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,860,941 A | 1/1999 | Saringer et al. |
| 5,950,813 A | 9/1999 | Hoskins et al. |
| 6,053,847 A | 4/2000 | Stearns et al. |
| 6,077,201 A | 6/2000 | Cheng |
| 6,102,834 A | 8/2000 | Chen |
| 6,155,958 A | 12/2000 | Goldberg |
| 6,182,029 B1 | 1/2001 | Friedman |
| 6,253,638 B1 | 7/2001 | Bermudez |
| 6,273,863 B1 | 8/2001 | Avni et al. |
| 6,371,891 B1 | 4/2002 | Speas |
| 6,413,190 B1 | 7/2002 | Wood et al. |
| 6,430,436 B1 | 8/2002 | Richter |
| 6,474,193 B1 | 11/2002 | Farney |
| 6,491,649 B1 | 12/2002 | Ombrellaro |
| 6,535,861 B1 | 3/2003 | OConnor et al. |
| 6,543,309 B2 | 4/2003 | Heim |
| D475,424 S | 6/2003 | Lee |
| 6,589,139 B1 | 7/2003 | Butterworth |
| 6,602,191 B2 | 8/2003 | Quy |
| 6,626,805 B1 | 9/2003 | Lightbody |
| D482,416 S | 11/2003 | Yang |
| 6,640,662 B1 | 11/2003 | Baxter |
| D484,931 S | 1/2004 | Tsai |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 7,156,665 B1 | 1/2007 | OConnor et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| 7,406,003 B2 | 7/2008 | Burkhardt et al. |
| D575,836 S | 8/2008 | Hsiao |
| 7,594,879 B2 | 9/2009 | Johnson |
| 7,726,034 B2 | 6/2010 | Wixey |
| 7,778,851 B2 | 8/2010 | Schoenberg et al. |
| 7,809,601 B2 | 10/2010 | Shaya et al. |
| 7,974,689 B2 | 7/2011 | Volpe et al. |
| 8,287,434 B2 | 10/2012 | Zavadsky et al. |
| 8,506,458 B2 | 8/2013 | Dugan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,672,812 B2 | 3/2014 | Dugan |
| 8,751,264 B2 | 6/2014 | Beraja et al. |
| 8,784,273 B2 | 7/2014 | Dugan |
| 8,823,448 B1 | 9/2014 | Shen |
| 8,979,711 B2 | 3/2015 | Dugan |
| 9,167,281 B2 | 10/2015 | Petrov et al. |
| 9,272,185 B2 | 3/2016 | Dugan |
| 9,311,789 B1 | 4/2016 | Gwin |
| 9,409,054 B2 | 8/2016 | Dugan |
| 9,443,205 B2 | 9/2016 | Wall |
| 9,480,873 B2 | 11/2016 | Chuang |
| 9,566,472 B2 | 2/2017 | Dugan |
| 9,579,056 B2 | 2/2017 | Rosenbek et al. |
| 9,629,558 B2 | 4/2017 | Yuen et al. |
| D793,494 S | 8/2017 | Mansfield et al. |
| 9,872,087 B2 | 1/2018 | DelloStritto et al. |

(56) References Cited

U.S. PATENT DOCUMENTS

| | | |
|---|---|---|
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 10,074,148 B2 | 9/2018 | Cashman et al. |
| 10,130,298 B2 | 11/2018 | Mokaya et al. |
| 10,155,134 B2 | 12/2018 | Dugan |
| 10,254,804 B2 | 4/2019 | Dusan |
| 10,325,070 B2 | 6/2019 | Beale et al. |
| 10,327,697 B1 | 6/2019 | Stein et al. |
| 10,424,033 B2 | 9/2019 | Romeo |
| 10,430,552 B2 | 10/2019 | Mihai |
| 10,542,914 B2 | 1/2020 | Forth et al. |
| 10,572,626 B2 | 2/2020 | Balram |
| 10,576,331 B2 | 3/2020 | Kuo |
| 10,660,534 B2 | 5/2020 | Lee et al. |
| 10,678,890 B2 | 6/2020 | Bitran et al. |
| 10,685,092 B2 | 6/2020 | Paparella et al. |
| 10,705,619 B2 | 7/2020 | Johri |
| 10,777,200 B2 | 9/2020 | Will et al. |
| 10,792,495 B2 | 10/2020 | Izvorski et al. |
| 10,874,905 B2 | 12/2020 | Belson et al. |
| 10,931,643 B1 | 2/2021 | Neumann |
| 11,000,735 B2 | 5/2021 | Orady et al. |
| 11,040,238 B2 | 6/2021 | Colburn |
| 11,045,709 B2 | 6/2021 | Putnam |
| 11,065,527 B2 | 7/2021 | Putnam |
| 2002/0160883 A1 | 10/2002 | Dugan |
| 2003/0036683 A1 | 2/2003 | Kehr et al. |
| 2003/0083596 A1 | 5/2003 | Kramer et al. |
| 2003/0092536 A1 | 5/2003 | Romanelli et al. |
| 2003/0109814 A1 | 6/2003 | Rummerfield |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2005/0020411 A1 | 1/2005 | Andrews |
| 2005/0049122 A1 | 3/2005 | Vallone et al. |
| 2005/0085346 A1 | 4/2005 | Johnson |
| 2005/0085353 A1 | 4/2005 | Johnson |
| 2005/0274220 A1 | 12/2005 | Reboullet |
| 2006/0003871 A1 | 1/2006 | Houghton |
| 2006/0064329 A1 | 3/2006 | Abolfathi et al. |
| 2006/0247095 A1 | 11/2006 | Rummerfield |
| 2008/0021834 A1 | 1/2008 | Holla et al. |
| 2008/0161166 A1 | 7/2008 | Lo |
| 2008/0300914 A1 | 12/2008 | Karkanias et al. |
| 2009/0011907 A1 | 1/2009 | Radow et al. |
| 2009/0046056 A1 | 2/2009 | Rosenberg et al. |
| 2009/0058635 A1 | 3/2009 | LaLonde et al. |
| 2009/0070138 A1 | 3/2009 | Langheier et al. |
| 2009/0211395 A1 | 8/2009 | Mul'e |
| 2010/0248899 A1 | 9/2010 | Bedell et al. |
| 2010/0248905 A1 | 9/2010 | Lu |
| 2010/0268304 A1 | 10/2010 | Matos |
| 2011/0047108 A1 | 2/2011 | Chakrabarty et al. |
| 2011/0172059 A1 | 7/2011 | Watterson et al. |
| 2011/0218814 A1 | 9/2011 | Coats |
| 2011/0275483 A1 | 11/2011 | Dugan |
| 2012/0065987 A1 | 3/2012 | Farooq et al. |
| 2012/0167709 A1 | 7/2012 | Chen et al. |
| 2012/0190502 A1 | 7/2012 | Paulus et al. |
| 2012/0295240 A1 | 11/2012 | Walker et al. |
| 2012/0310667 A1 | 12/2012 | Altman et al. |
| 2013/0123667 A1 | 5/2013 | Komatireddy et al. |
| 2013/0296987 A1 | 11/2013 | Rogers et al. |
| 2014/0006042 A1 | 1/2014 | Keefe et al. |
| 2014/0011640 A1 | 1/2014 | Dugan |
| 2014/0155129 A1 | 6/2014 | Dugan |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0207264 A1 | 7/2014 | Quy |
| 2014/0246499 A1 | 9/2014 | Proud et al. |
| 2014/0257837 A1 | 9/2014 | Walker et al. |
| 2014/0309083 A1 | 10/2014 | Dugan |
| 2014/0315689 A1 | 10/2014 | Vauquelin et al. |
| 2014/0322686 A1 | 10/2014 | Kang |
| 2015/0088544 A1 | 3/2015 | Goldberg |
| 2015/0151162 A1 | 6/2015 | Dugan |
| 2015/0158549 A1 | 6/2015 | Gros et al. |
| 2015/0161331 A1 | 6/2015 | Oleynik |
| 2015/0265205 A1* | 9/2015 | Rosenbek ............ A61B 5/4803 600/586 |
| 2015/0339442 A1 | 11/2015 | Oleynik |
| 2015/0341812 A1 | 11/2015 | Dion et al. |
| 2016/0023081 A1 | 1/2016 | Popa-Simil |
| 2016/0117471 A1 | 4/2016 | Belt et al. |
| 2016/0140319 A1 | 5/2016 | Stark et al. |
| 2016/0151670 A1 | 6/2016 | Dugan |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2017/0004260 A1 | 1/2017 | Moturu et al. |
| 2017/0014671 A1 | 1/2017 | Burns, Sr. |
| 2017/0046488 A1 | 2/2017 | Pereira |
| 2017/0095692 A1 | 4/2017 | Chang et al. |
| 2017/0095693 A1 | 4/2017 | Chang et al. |
| 2017/0106242 A1 | 4/2017 | Dugan |
| 2017/0113092 A1 | 4/2017 | Johnson |
| 2017/0136296 A1 | 5/2017 | Barrera et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0243028 A1 | 8/2017 | LaFever et al. |
| 2017/0265800 A1 | 9/2017 | Auchinleck et al. |
| 2017/0278209 A1 | 9/2017 | Olsen et al. |
| 2017/0282015 A1 | 10/2017 | Wicks et al. |
| 2017/0300654 A1 | 10/2017 | Stein et al. |
| 2017/0312614 A1 | 11/2017 | Tran et al. |
| 2017/0329917 A1 | 11/2017 | McRaith et al. |
| 2017/0344726 A1 | 11/2017 | Duffy et al. |
| 2017/0360586 A1 | 12/2017 | Dempers et al. |
| 2017/0368413 A1 | 12/2017 | Shavit |
| 2018/0052962 A1 | 2/2018 | Van Der Koijk et al. |
| 2018/0056104 A1 | 3/2018 | Cromie et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0102190 A1 | 4/2018 | Hogue et al. |
| 2018/0200577 A1 | 7/2018 | Dugan |
| 2018/0220935 A1 | 8/2018 | Tadano et al. |
| 2018/0240552 A1 | 8/2018 | Tuyl et al. |
| 2018/0263530 A1 | 9/2018 | Jung |
| 2018/0271432 A1 | 9/2018 | Auchinleck et al. |
| 2018/0280784 A1 | 10/2018 | Romeo et al. |
| 2018/0330058 A1 | 11/2018 | Bates |
| 2018/0330824 A1 | 11/2018 | Athey et al. |
| 2018/0373844 A1 | 12/2018 | Ferrandez-Escamez et al. |
| 2019/0019578 A1 | 1/2019 | Vaccaro |
| 2019/0035043 A1 | 1/2019 | Jones et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0088356 A1 | 3/2019 | Oliver et al. |
| 2019/0115097 A1 | 4/2019 | Macoviak et al. |
| 2019/0117128 A1 | 4/2019 | Chen et al. |
| 2019/0126099 A1 | 5/2019 | Hoang |
| 2019/0134454 A1 | 5/2019 | Mahoney et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |

(56) References Cited

U.S. PATENT DOCUMENTS

| | | |
|---|---|---|
| 2019/0200920 A1 | 7/2019 | Tien et al. |
| 2019/0209891 A1 | 7/2019 | Fung |
| 2019/0244540 A1 | 8/2019 | Errante et al. |
| 2019/0269343 A1 | 9/2019 | Ramos Murguialday et al. |
| 2019/0290964 A1 | 9/2019 | Oren |
| 2019/0304584 A1 | 10/2019 | Savolainen |
| 2019/0307983 A1 | 10/2019 | Goldman |
| 2019/0354632 A1 | 11/2019 | Mital et al. |
| 2020/0005928 A1 | 1/2020 | Daniel |
| 2020/0051446 A1 | 2/2020 | Rubinstein et al. |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0152339 A1 | 5/2020 | Pulitzer et al. |
| 2020/0160198 A1 | 5/2020 | Reeves et al. |
| 2020/0285322 A1 | 5/2020 | Johri |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0289878 A1 | 9/2020 | Arn et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0395112 A1 | 12/2020 | Ronner |
| 2020/0401224 A1 | 12/2020 | Cotton |
| 2021/0074178 A1 | 3/2021 | Ilan et al. |
| 2021/0098129 A1 | 4/2021 | Neumann |
| 2021/0128978 A1 | 5/2021 | Gilstrom et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |

FOREIGN PATENT DOCUMENTS

| | | |
|---|---|---|
| CN | 103488880 A | 1/2014 |
| CN | 104335211 | 2/2015 |
| CN | 105894088 A | 8/2016 |
| CN | 105930668 A | 9/2016 |
| CN | 106127646 A | 11/2016 |
| CN | 107430641 A | 12/2017 |
| CN | 207220817 U | 4/2018 |
| CN | 112603295 A | 4/2021 |
| DE | 102018202497 A1 | 8/2018 |
| DE | 102018211212 A1 | 1/2019 |
| DE | 102019108425 B3 | 8/2020 |
| EP | 3688537 A1 | 8/2020 |
| EP | 3731733 A1 | 11/2020 |
| JP | 2003225875 A | 8/2003 |
| JP | 6659831 B2 | 10/2017 |
| JP | 2019134909 A | 8/2019 |
| JP | 6573739 B1 | 9/2019 |
| JP | 6710357 B1 | 6/2020 |
| JP | 6775757 B1 | 10/2020 |
| JP | 2021026768 A | 2/2021 |
| JP | 2021027917 A | 2/2021 |
| KR | 20020009724 A | 2/2002 |
| KR | 20020065253 A | 8/2002 |
| KR | 20110099953 A | 9/2011 |
| KR | 20160093990 A | 8/2016 |
| KR | 20170038837 A | 4/2017 |
| KR | 20190011885 A | 2/2019 |
| KR | 101988167 B1 | 6/2019 |
| KR | 102116664 B1 | 7/2019 |
| KR | 102116968 B1 | 3/2020 |
| KR | 20200025290 A | 3/2020 |
| KR | 102162522 B1 | 4/2020 |
| KR | 102142713 B1 | 5/2020 |
| KR | 20200056233 A | 5/2020 |
| KR | 102120828 B1 | 6/2020 |
| KR | 102173553 B1 | 11/2020 |
| KR | 102180079 B1 | 11/2020 |
| KR | 102224618 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102264498 B1 | 6/2021 |
| WO | 2001050387 A1 | 7/2001 |
| WO | 2020200891 A1 | 2/2003 |
| WO | 2003043494 | 5/2003 |
| WO | 2005018453 A1 | 3/2005 |
| WO | 2018132999 A1 | 1/2017 |
| WO | 2018171853 A1 | 9/2018 |
| WO | 2019204876 A1 | 4/2019 |
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021038980 A1 | 3/2021 |
| WO | 2021061061 A1 | 4/2021 |
| WO | 2021138620 A1 | 7/2021 |

OTHER PUBLICATIONS

International Search Report and Written Opinion for International Application No. PCT/US2021/032807, dated Sep. 6, 2021, 11 pages.

* cited by examiner

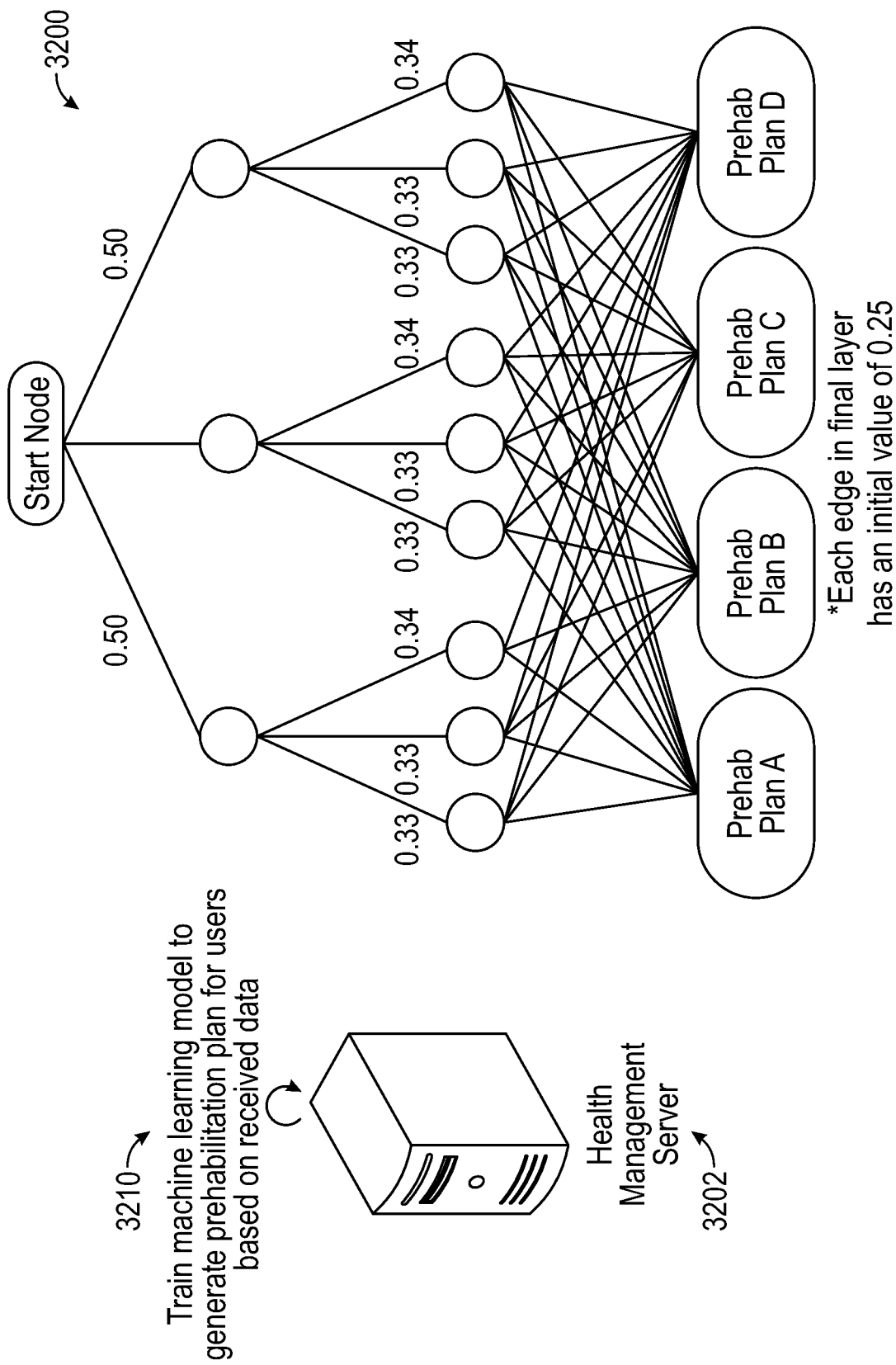

SYSTEMS AND METHODS FOR USING MACHINE LEARNING TO CONTROL AN ELECTROMECHANICAL DEVICE USED FOR PREHABILITATION, REHABILITATION, AND/OR EXERCISE

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. This application also claims priority to and the benefit of U.S. Provisional Patent Application Ser. No. 63/066,488, filed Aug. 17, 2020, titled "Systems and Methods for using Machine Learning to Control an Electromechanical Device used for Prehabilitation and/or Exercise," the entire disclosure of which is hereby incorporated by reference for all purposes.

TECHNICAL FIELD

This disclosure relates generally to electromechanical devices. More specifically, this disclosure relates to a control system that uses machine learning to control a prehabilitation and exercise electromechanical device.

BACKGROUND

Various devices may be used by people for exercising and/or rehabilitating parts of their bodies. For example, to maintain a desired level of fitness, users may operate devices for a period of time or distance as part of a workout regime. In another example, a person may undergo knee surgery and a physician may provide a treatment plan for prehabilitation that includes operating an electromechanical device (e.g., an exercise bike, a device used for prehabilitation, etc.) for a period of time and/or distance periodically to strengthen and/or improve flexibility of the knee. The exercise and/or prehabilitation devices may include pedals on opposite sides. The devices may be operated by a user engaging the pedals with their feet or their hands and rotating the pedals.

Machine learning is a field of computer science for discovering methodologies, algorithms, heuristics, and the like, whether in hardware, software or both, for the purpose of enabling computers or applications running on computers to learn without being explicitly programmed. Machine learning works through a variety of mechanisms, including iteration, optimization, pruning, testing, and the like. For example, a machine learning model may be trained on a set of training data, such that the model may be used to process newly received data to generate useful predictions and/or classifications. Further, machine learning is continual or even continuous: The model developed for machine learning can always be further improved in light of the goals toward which the model is trained to achieve. While machine learning could, in principle, be terminated at some point, the learning aspect would cease at that point.

SUMMARY

In general, the present disclosure provides a control system for an adjustable prehabilitation and exercise device and associated components.

In one aspect, the present disclosure provides a computer-implemented system. The computer-implemented system includes, in one example, an electromechanical device, a user portal, and a computing device. The electromechanical device is configured to be manipulated by a user while the user performs a prehabilitation procedure. The user portal includes an output device and an input device. The output device is configured to communicate a prehabilitation plan to the user. The prehabilitation plan includes at least one exercise session comprising one or more exercises to be performed on the electromechanical device. The computing device is configured to receive user data relating to the user. The user data includes health history data relating to health indicators of the user. The computing device is also configured to receive treatment data relating to a set of treatment plans and outcomes. The set of treatment plans is capable of being offered to the user. The computing device is further configured to generate the prehabilitation plan by using a machine learning model to process the user data and the treatment data. The computing device is also configured to select, for the electromechanical device, an electromechanical device configuration that enables the one or more exercises of the prehabilitation plan to be performed by the user. The electromechanical device configuration enables the one or more exercises to be performed to improve performance of an area of the user's body. The computing device is further configured to enable the electromechanical device to implement the electromechanical device configuration by providing the electromechanical device configuration to the electromechanical device.

In another aspect, the present disclosure provides a method for using machine learning to control an electromechanical device is configured. The method includes receiving user data relating to a user capable of operating the electromechanical device as part of a prehabilitation procedure. The user data comprises health history data relating to health indicators of the user. The method further comprises receiving treatment data relating to a set of treatment plans and outcomes. The set of treatment plans is capable of being offered to the user. The method further comprises generating a prehabilitation plan by using a machine learning model to process the user data and the treatment data. The prehabilitation plan includes at least one exercise session comprising one or more exercises to be performed on the electromechanical device. The method further comprises enabling the prehabilitation plan to be distally accessible by one or more user portals. The method further comprises selecting, for the electromechanical device, an electromechanical device configuration that enables the one or more exercises of the prehabilitation plan to be performed by the user. The electromechanical device configuration enables the one or more exercises to be performed to improve performance of an area of the user's body. The method further comprises enabling the electromechanical device to implement the electromechanical device configuration by providing the electromechanical device configuration to the electromechanical device.

In another aspect, the present disclosure provides a system for operating an electromechanical device includes a memory device storing instructions and a processing device communicatively coupled to the memory device. The processing device, when executing the instructions, is to receive user data relating to a user capable of operating the electromechanical device as part of a prehabilitation procedure. The user data comprises health history data relating to health indicators of the user. The processing device, when executing the instructions, is further to receive treatment data relating to a set of treatment plans and outcomes. The set of treatment plans is capable of being offered to the user. The processing device, when executing the instructions, is further to generate a prehabilitation plan by using a machine learning model to process the user data and the treatment data. The prehabilitation plan includes at least one exercise session comprising one or more exercises to be performed on the electromechanical device. The processing device, when executing the instructions, is further to enable the prehabilitation plan to be distally accessible by one or more user portals. The processing device, when executing the instructions, is further to enable the prehabilitation plan to be distally accessible by one or more user portals. The processing device, when executing the instructions, is further to select, for the electromechanical device, an electromechanical device configuration that enables the one or more exercises of the prehabilitation plan to be performed by the user. The electromechanical device configuration enables the one or more exercises to be performed to improve performance of an area of the user's body. The processing device, when executing the instructions, is further to enable the electromechanical device to implement the electromechanical device configuration by providing the electromechanical device configuration to the electromechanical device.

In yet another aspect, the present disclosure provides a tangible, non-transitory computer-readable medium storing instructions that, when executed by a processing device, cause the processing device to receive user data relating to a user capable of operating the electromechanical device as part of a prehabilitation procedure. The user data comprises health history data relating to one or more health indicators of the user. The instructions, when executed by the processing device, further cause the processing device to receive treatment data relating to a set of treatment plans and outcomes. The set of treatment plans is capable of being offered to the user. The instructions, when executed by the processing device, further cause the processing device to generate a prehabilitation plan by using a machine learning model to process the user data and the treatment data. The prehabilitation plan includes at least one exercise session comprising one or more exercises to be performed on the electromechanical device. The instructions, when executed by the processing device, further cause the processing device to enable the prehabilitation plan to be distally accessible by one or more user portals. The instructions, when executed by the processing device, further cause the processing device to select, for the electromechanical device, an electromechanical device configuration that enables the one or more exercises of the prehabilitation plan to be performed by the user. The electromechanical device configuration enables the one or more exercises to be performed to improve performance of an area of the user's body. The instructions, when executed by the processing device, further cause the processing device to enable the electromechanical device to implement the electromechanical device configuration by providing the electromechanical device configuration to the electromechanical device.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

The terminology used herein is for the purpose of describing particular example embodiments only, and is not intended to be limiting. As used herein, the singular forms "a," "an," and "the" may be intended to include the plural forms as well, unless the context clearly indicates otherwise. For example, where only one item is intended, the phrase "only one" or similar language is used. The method steps, processes, and operations described herein are not to be construed as necessarily requiring their performance in the particular order discussed or illustrated, unless specifically identified as an order of performance. It is also to be understood that additional or alternative steps may be employed. Further, the phrase "based on" is intended to mean "based, at least in part, on" unless explicitly stated otherwise.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a user, such as a patient (or directed to be performed by or on a patient, including, without limitation, remotely, i.e., distally, through telemedicine), to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy.

As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all of the foregoing procedures. In one embodiment of prehabilitation, a pre-surgical procedure or a pre-non-surgical treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation plan for a user. Additionally, or alternatively, the systems and methods described herein may use artificial intelligence and/or machine learning to recommend an optimal exercise machine configuration for a user. For example, a machine learning model may be trained on historical data such that the machine learning model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended healthcare professional specialist to contact, and/or the like.

The terms telemedicine, telehealth, telemed, teletherapeutic, etc. may be used interchangeably herein.

Some embodiments are described in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

The term "health-related event" may refer to an event that causes a change to the health of the user, such as a change that adversely affects the health of the user. For example, a health-related event may be a medical condition, an injury, an ailment, a medical procedure such as a surgery, and/or any other event capable of affecting the health of the user. In some embodiments, a health-related event may be an event that adversely affects the health of the user such that the user has to undergo prehabilitation. One of the purposes of prehabilitation is to prevent or to reduce the likelihood that the health-related event occurs. This may be done by improving one or more health indicators relating to a target area of the user's body that would be affected by the health-related event. For example, prehabilitation may be used to improve a ROM of a target area of a user, to strengthen one or more muscles and/or tendons relating to the target area, to improve existing muscle memory for the one or more muscles, to establish new muscle memory for the one or more muscles, to improve blood flow, and/or the like.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

FIGS. 32A-32G generally illustrate an example prehabilitation system that utilizes machine learning to generate and optimize a prehabilitation plan of a user.

DETAILED DESCRIPTION

Figure 1:
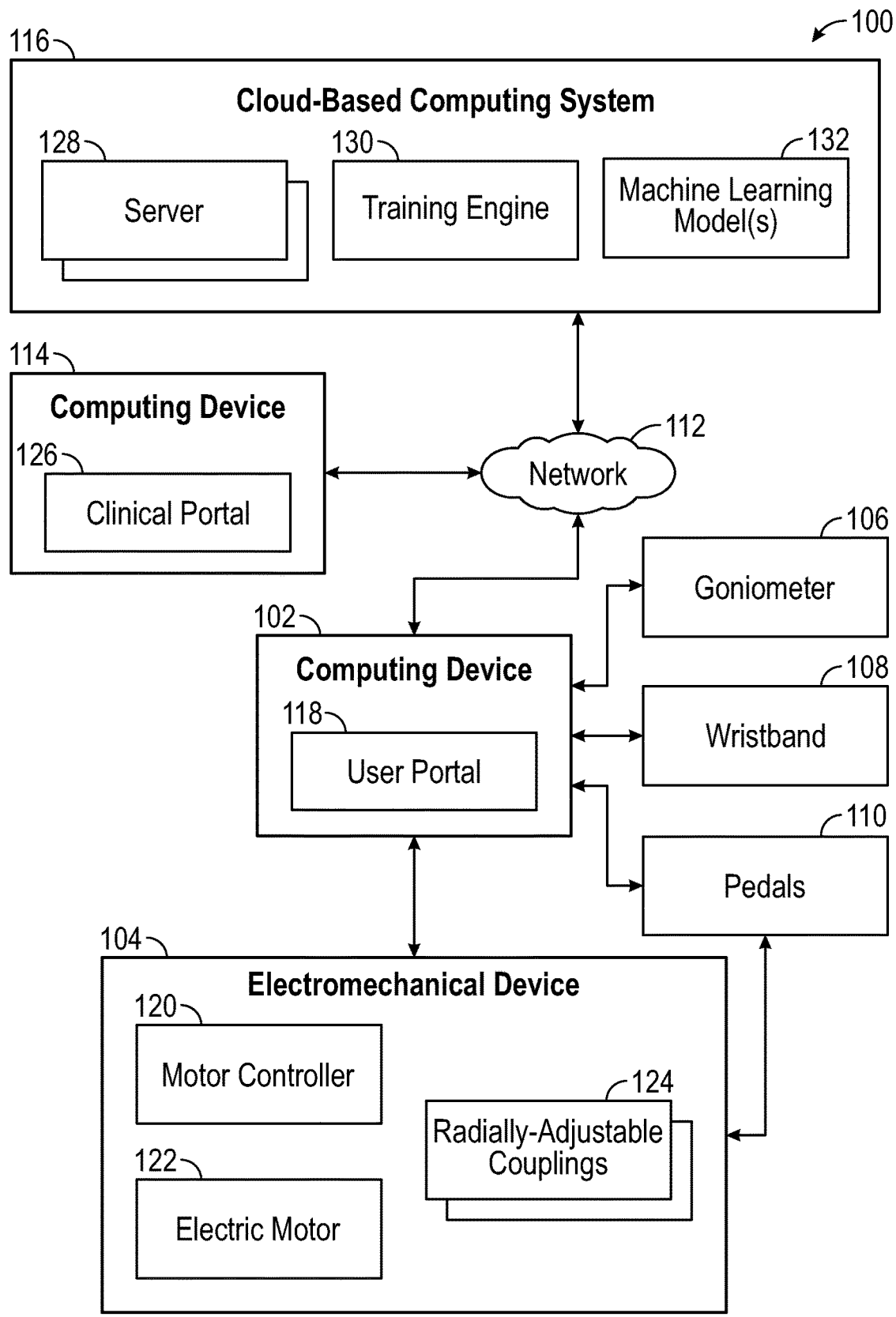
FIG. 1 generally illustrates a block diagram of an embodiment of a computer-implemented system for managing a prehabilitation plan according to principles of the present disclosure.

Improvement is desired in the field of devices used for prehabilitation and exercise. People may injure, sprain, or tear a body part and consult a healthcare professional to diagnose the injury. As used herein, and without limiting the foregoing, a "healthcare professional" may be a human being, a robot, a virtual assistant, a virtual assistant in a virtual and/or augmented reality, or an artificially intelligent entity, including a software program, integrated software and hardware, or hardware alone. If, for example, the healthcare professional is a human being, the healthcare professional may be any person with a credential, license, degree, or the like in the field of medicine, physical therapy, prehabilitation, rehabilitation, exercise, strength training, endurance training, and/or the like. A healthcare professional may refer to a doctor, physician assistant, nurse, chiropractor, dentist, physical therapist, physiotherapist, kinesiologist, acupuncturist, physical train, coach, personal trainer, neurologist, cardiologist, or the like. A healthcare professional may refer to any person with a credential, license, degree, or the like in the field of medicine, physical therapy, rehabilitation, or the like.

In some situations, a healthcare professional, such as a physician, may prescribe a treatment plan to a patient. A treatment plan, as used herein, may refer to a plan for a patient who is receiving treatment relating to a past, present, or future illness, condition, or ailment; an exercise plan, strength training plan, or endurance-increasing plan for an individual trying to improve his or her fitness; and/or any other plan capable of affecting the health of the patient. A treatment plan may, for example, include a prehabilitation plan for an individual who is to undergo surgery or who may have to undergo surgery at a later time period, a rehabilitation plan for a patient who has undergone surgery or who has a particular illness, condition, or ailment, and/or the like.

In some instances, the physician may prescribe a treatment plan that includes operating one or more electrical, mechanical, optic, electro-optical and/or electromechanical devices (e.g., pedaling devices for arms or legs) for a period of time to exercise the affected area in an attempt to improve one or more characteristics of the affected body part and to attempt to regain as much normal operability of that affected body part as possible. In other instances, the person with the affected body part may determine to operate a device without consulting a physician. In either scenario, the devices that are operated lack effective monitoring of progress of the affected area and control over the electromechanical device 104 during operation by the user. Conventional devices lack components that enable operating the electromechanical device in various modes that are designed to enhance the rate and effectiveness of prehabilitation, rehabilitation, and/or the like.

Further, conventional systems lack monitoring devices that aid in determining one or more properties of the user (e.g., range of motion of the affected area, heartrate of the user, etc.) and enable adjusting components based on the determined properties. When the user is supposed to be adhering to a treatment plan, conventional systems may not provide real-time results of sessions to the healthcare professionals. That is, typically the healthcare professionals have to rely on the patient's word as to whether the patient adhering to the treatment plan.

Additionally, computer-implemented treatment systems do not provide a mechanism for a healthcare professional and/or patient to closely monitor patient progress in real-time. Consequently, the user may over-exert himself or herself while exercising, may exercise using improper form, exercise using a sub-optimal range of motion, and/or exercise in any other manner that risks adversely affecting a health indicator of the user (e.g., by reinjuring a body part that was previously operated on or injured) and/or increasing the cost of the user's patient recovery or improvement process without an attendant benefit in improvement to the underlying condition. These risks are especially apparent in both rehabilitation and prehabilitation.

Furthermore, computer-implemented treatment systems are unable to generate optimal prehabilitation for patients. For example, if a patient undergoing prehabilitation has previously torn an ACL, the patient may have a reduced or limited range of motion (ROM) of one or more body parts affected by the torn ACL. The torn ACL may have also affected strength and/or endurance of the patient. Consequently, an optimal prehabilitation plan should improve the patient's ROM, strength, and/or endurance (e.g., stamina, etc.) to reduce the likelihood that the patient experiences a recurring injury. Additionally, an optimal prehabilitation plan for a patient may vary based on a degree to which a surgery for the torn ACL was successful, based on the patient's medical history, based on the patient's demographic information, based on the patient's ability to accurately carry out a prehabilitation plan, and/or the like. Computer-implemented treatment systems that use electromechanical devices are unable to generate optimal treatment plans that account for these variances.

Moreover, in the context of patient rehabilitation, a computer-implemented treatment system will have the benefit of generating a rehabilitation plan based in part on data relating to an injury that has already occurred. However, in order to generate an optimal prehabilitation plan for a patient undergoing prehabilitation, a prehabilitation system should be configured to determine characteristics of the optimal prehabilitation plan before any injury occurs (wherein the prehabilitation system is unable to rely on data relating to an injury that has already occurred when generating the optimal prehabilitation plan).

Another technical problem may relate to information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to a medical condition of the patient). That is, some sources that are used by various healthcare professional entities may be installed on their local computing devices and may use proprietary formats. Accordingly, some embodiments of the present disclosure may use an API to obtain, via interfaces exposed by APIs used by the sources, the formats used by the sources. In some embodiments, when information is received from the sources, the API may map and convert the format used by the sources to a standardized format used by the artificial intelligence engine. Further, the information converted to the standardized format used by the artificial intelligence engine may be stored in a database accessed by the artificial intelligence engine when performing any of the techniques disclosed herein. Using the information converted to a standardized format may enable more accurately determining the procedures to perform for the patient.

To that end, the standardized information may enable generating prehabilitation plans having a particular format that can be processed by various applications (e.g., telehealth). For example, applications, such as telehealth applications, may be executing on various computing devices of healthcare professionals and/or patients. The applications (e.g., standalone or web-based) may be provided by a server and may be configured to process data according to a format in which the treatment plans are implemented. Accordingly, the disclosed embodiments may provide a technical solution by (i) receiving, from various sources (e.g., EMR systems), information in non-standardized and/or different formats; (ii) standardizing the information; and (iii) generating, based on the standardized information, prehabilitation plans having standardized formats that are capable of being processed by applications (e.g., telehealth application) executing on computing devices of healthcare professional and/or patients.

Still further, another technical problem may involve distally treating, via a computing device during a telemedicine or telehealth session, a patient from a location different than a location at which the patient is located. An additional technical problem is controlling or enabling the control of, from the different location, an electromechanical device used by the patient at the location at which the patient is located. Oftentimes, when a patient undergoes rehabilitative surgery (e.g., knee surgery), a physical therapist or other healthcare professional may prescribe an electromechanical device to the patient to use to perform a treatment protocol at their residence or any mobile location or temporary domicile.

Since the healthcare professional is located in a location different from the patient and the electromechanical device, it may be technically challenging for the healthcare professional to monitor the patient's actual progress (as opposed to relying on the patient's word about their progress) in using the electromechanical device, to modify the treatment plan according to the patient's progress, to adapt the electromechanical device to the personal characteristics of the patient as the patient performs the treatment plan, and the like.

Accordingly, aspects of the present disclosure generally relate to a prehabilitation system for a prehabilitation and exercise electromechanical device (referred to herein as "electromechanical device"). The electromechanical device may include an electric motor configured to drive one or more radially-adjustable couplings to rotationally move pedals coupled to the radially-adjustable couplings. The electromechanical device may be operated by a user engaging the pedals with their hands or their feet and rotating the pedals to exercise and/or rehabilitate a desired body part. The electromechanical device and the prehabilitation system may be included as part of a larger prehabilitation system. The prehabilitation system may also include monitoring devices (e.g., goniometer, wristband, force sensors in the pedals, etc.) that provide valuable information about the user to the prehabilitation system. As such, the monitoring devices may be in direct or indirect communication with the prehabilitation system.

The monitoring devices may include a goniometer that is configured to measure range of motion (e.g., angles of extension and/or bend) of a body part to which the goniometer is attached. The measured range of motion may be presented to the user and/or a physician via a user portal and/or a clinical portal. Also the prehabilitation system may use the measured range of motion to determine whether to adjust positions of the pedals on the radially-adjustable couplings and/or to adjust the mode types (e.g., passive, active-assisted, resistive, active) and/or durations to operate the electromechanical device during a treatment plan. The monitoring devices may also include a wristband configured to track the steps of the user over a time period (e.g., day, week, etc.) and/or measure vital signs of the user (e.g., heartrate, blood pressure, oxygen level). The monitoring devices may also include force sensors disposed in the pedals that are configured to measure the force exerted by the user on the pedals.

The prehabilitation system may enable operating the electromechanical device in a variety of modes, such as a passive mode, an active-assisted mode, a resistive mode, and/or an active mode. The prehabilitation system may use the information received from the measuring devices to adjust parameters (e.g., reduce resistance provided by electric motor, increase resistance provided by the electric motor, increase/decrease speed of the electric motor, adjust position of pedals on radially-adjustable couplings, etc.) while operating the electromechanical device in the various modes. The prehabilitation system may receive the information from the monitoring devices, aggregate the information, make determinations using the information, and/or transmit the information to a cloud-based computing system for storage. The cloud-based computing system may maintain the information that is related to each user.

A clinician and/or a machine learning model may generate a treatment plan, such as a prehabilitation plan for a user, to improve and/or strengthen a part of the user's body using at least the electromechanical device. A treatment plan may include a set of pedaling sessions using the electromechanical device, a set of joint extension sessions, a set of flex sessions, a set of walking sessions, a set of heartrates per pedaling session and/or walking session, and the like. Additionally, or alternatively, the treatment plan may include a medical procedure to perform on the patient, a treatment protocol for the patient using the electromechanical device, a diet regimen for the patient, a medical regiment for the patient, a sleep regiment for the patient, and/or the like.

Each pedaling session may specify that a user is to operate the electromechanical device in a combination of one or more modes, including: passive, active-passive, active, and resistive. The pedaling session may specify that the user is to wear the wristband and the goniometer during the pedaling session. Further, each pedaling session may include a set amount of time that the electromechanical device is to operate in each mode, a target heartrate for the user during each mode in the pedaling session, target forces that the user is to exert on the pedals during each mode in the pedaling session, target ranges of motion the body parts are to attain during the pedaling session, positions of the pedals on the radially-adjustable couplings, and the like.

Each joint extension session may specify a target angle of extension at the joint, and each set of joint flex sessions may specify a target angle of flex at the joint. Each walking session may specify a target number of steps the user should take over a set period of time (e.g., day, week etc.) and/or a target heartrate to achieve and/or maintain during the walking session.

The treatment plans may be stored in the cloud-based computing system and downloaded to the computing device of the user when the user is ready to begin the treatment plan. In some embodiments, the computing device that executes a clinical portal may transmit the treatment plan to the computing device that executes a user portal and the user may initiate the treatment plan when ready.

In addition, the disclosed prehabilitation system may enable a physician to monitor the progress of the user in real-time using the clinical portal. The clinical portal may present information pertaining to when the user is engaged in one or more sessions, statistics (e.g., speed, revolutions per minute, position of pedals, force on the pedals, vital signs, number of steps taken by user, range of motion, etc.) of the sessions, and the like. The clinical portal may also enable the physician to view before and after session images of the affected body part of the user to enable the physician to judge how well the treatment plan is working and/or to make adjustments to the treatment plan. The clinical portal may enable the physician to dynamically change a parameter (e.g., position of pedals, amount of resistance provided by electric motor, speed of the electric motor, duration of one of the modes, etc.) of the treatment plan in real-time based on information received from the prehabilitation system.

Furthermore, the disclosed prehabilitation system may generate a prehabilitation plan by using a machine learning model to process received user data and treatment data. The prehabilitation plan may include an exercise session to be performed on an electromechanical device. The disclosed prehabilitation system may select a device configuration for the electromechanical device, where the device configuration corresponds to the prehabilitation plan. The disclosed prehabilitation system may provide the device configuration to the electromechanical device such that the device configuration may be implemented on the electromechanical device.

The disclosed techniques provide numerous benefits over conventional systems. For example, the prehabilitation system provides granular control over the components of the electromechanical device to enhance the efficiency and effectiveness of prehabilitation of the user. The prehabilitation system enables operating the electromechanical device in any suitable combination of the modes described herein by controlling the electric motor, for example. To provide a specific example, the prehabilitation system uses information received from the monitoring devices to adjust parameters of components of the electromechanical device in real-time during a pedaling session. By adjusting parameters of components of the electromechanical device in real-time, the prehabilitation system enables the user to exercise efficiently and effectively while reducing chances of injury. For example, if a user is applying too much pressure to a pedal, a resistance of the pedal may be adjusted to reduce the risk of injury during the pedaling session. This adjustment conserves resources (e.g., power resources, processing resources, network resources, and/or the like) of the electromechanical device and related computing or other devices. For example, resources are conserved relative to a prior system that produces inferior performance, results, etc., such as a prior system that is unable to adjust parameters of one or more components of an exercise device while a user is using the exercise device to exercise. Additional benefits of this disclosure include enabling a computing device operated by a physician to monitor the progress of a user participating in a prehabilitation plan in real-time (e.g., during a telemedicine or telehealth session) and/or to control operation of the electromechanical device during a pedaling session.

Furthermore, some embodiments described herein use machine learning to generate a prehabilitation plan that is optimal for the user. For example, the prehabilitation system may use machine learning to generate a prehabilitation plan that includes an exercise session, where the exercise session may be performed by the user when a device configuration is implemented on the electromechanical device. The device configuration allows the exercise session to be performed using an optimal Range of Motion (ROM), performed at an optimal strength, and/or performed at an optimal endurance. By using machine learning to generate an optimal treatment plan for the user, the prehabilitation system conserves resources of the electromechanical device (and/or related devices) relative to a prior system that does not utilize machine learning to generate an optimal prehabilitation plan for a user. For example, the prehabilitation system conserves resources that a prior system may expend generating, transmitting, and/or displaying data relating to an inferior treatment plan. An inferior treatment plan, as used herein, may refer to a treatment plan not optimized for the user, a treatment plan not generated using machine learning, a treatment plan more likely to injure or re-injure a user (relative to an optimal treatment plan generated for the user), a treatment plan requiring more time for the user to recover from an exercise session performed using an exercise device (relative to the optimal treatment plan), and/or the like. Further, by using machine learning to generate an optimal prehabilitation plan that accounts for a number of factors that influence optimality (e.g., user demographic, medical history, surgery results relating to past injuries and/or conditions, and/or the like), the prehabilitation system reduces a likelihood of injury or re-injury, improves or strengthens one or more body parts of the user at risk for injury or re-injury, improves the overall health of the user, and/or the like.

FIGS. 1 through 34, discussed below, and the various embodiments used to describe the principles of this disclosure are by way of illustration only and should not be construed in any way to limit the scope of the disclosure.

FIG. 1 generally illustrates a block diagram of an embodiment of a computer-implemented system 100 for managing a prehabilitation plan architecture according to principles of the present disclosure. In some embodiments, the computer-implemented system 100 may include a computing device 102 communicatively coupled to an electromechanical device 104, a goniometer 106, a wristband 108, and/or pedals 110 of the electromechanical device 104. Each of the computing device 102, the electromechanical device 104, the goniometer 106, the wristband 108, and the pedals 110 may include one or more processing devices, memory devices, and network interface cards. The network interface cards may enable communication via a wireless protocol for transmitting data over short distances, such as Bluetooth, ZigBee, etc. In some embodiments, the computing device 102 is communicatively coupled to the electromechanical device 104, goniometer 106, the wristband 108, and/or the pedals 110 via Bluetooth.

Additionally, the network interface cards may enable communicating data over long distances, and in one example, the computing device 102 may communicate with a network 112. Network 112 may be a public network (e.g., connected to the Internet via wired (Ethernet) or wireless (WiFi)), a private network (e.g., a local area network (LAN) or wide area network (WAN)), or a combination thereof. The computing device 102 may be communicatively coupled with a computing device 114 and a cloud-based computing system 116.

The computing device 102 may be any suitable computing device, such as a laptop, tablet, smartphone, or computer. The computing device 102 may include a display that is capable of presenting a user interface, such as a user portal 118. The user portal 118 may be implemented in computer instructions stored on the one or more memory devices of the computing device 102 and executable by the one or more processing devices of the computing device 102. The user portal 118 may present various screens to a user that enable the user to view a treatment plan, initiate a pedaling session of the treatment plan, control parameters of the electromechanical device 104, view progress of prehabilitation during the pedaling session, and so forth as described in more detail below. The computing device 102 may also include instructions stored on the one or more memory devices that, when executed by the one or more processing devices of the computing device 102, perform operations to control the electromechanical device 104.

The computing device 114 may execute a clinical portal 126. The clinical portal 126 may be implemented in computer instructions stored on the one or more memory devices of the computing device 114 and executable by the one or more processing devices of the computing device 114. The clinical portal 126 may present various screens to a physician that enable the physician to create a treatment plan for a patient, view progress of the user throughout the treatment plan, view measured properties (e.g., angles of bend/extension, force exerted on pedals 110, heartrate, steps taken, images of the affected body part) of the user during sessions of the treatment plan, view properties (e.g., modes completed, revolutions per minute, etc.) of the electromechanical device 104 during sessions of the treatment plan. The treatment plan specific to a patient may be transmitted via the network 112 to the cloud-based computing system 116 for storage and/or to the computing device 102 so the patient may begin the treatment plan.

The electromechanical device 104 may be an adjustable pedaling device for exercising a target area of the body of a user (e.g., a body part, muscle, tendon, and/or the like). For example, a user may perform one or more exercise sessions on the electromechanical device 104 to strengthen, increase flexibility, and/or improve endurance of the target area. The electromechanical device 104 may include at least one or more motor controllers 120, one or more electric motors 122, and one or more radially-adjustable couplings 124. Two pedals 110 may be coupled to two radially-adjustable couplings 124 via a left and right pedal assemblies that each include a respective stepper motor. The motor controller 120 may be operatively coupled to the electric motor 122 and configured to provide commands to the electric motor 122 to control operation of the electric motor 122. The motor controller 120 may include any suitable microcontroller including a circuit board having one or more processing devices, one or more memory devices (e.g., read-only memory (ROM) and/or random access memory (RAM)), one or more network interface cards, and/or programmable input/output peripherals. The motor controller 120 may provide control signals or commands to drive the electric motor 122. The electric motor 122 may be powered to drive one or more radially-adjustable couplings 124 of the electromechanical device 104 in a rotational manner. The electric motor 122 may provide the driving force to rotate the radially-adjustable couplings 124 at configurable speeds. The couplings 124 are radially-adjustable in that a pedal 110 attached to the coupling 124 may be adjusted to a number of positions on the coupling 125 in a radial fashion. Further, the electromechanical device 104 may include current shunt to provide resistance to dissipate energy from the electric motor 122. As such, the electric motor 122 may be configured to provide resistance to rotation of the radially-adjustable couplings 124.

The computing device 102 may be communicatively connected to the electromechanical device 104 via the network interface card on the motor controller 120. The computing device 102 may transmit commands to the motor controller 120 to control the electric motor 122. The network interface card of the motor controller 120 may receive the commands and transmit the commands to the electric motor 122 to drive the electric motor 122. In this way, the computing device 102 is operatively coupled to the electric motor 122.

The computing device 102 and/or the motor controller 120 may be referred to herein as a prehabilitation system or a control system. The user portal 118 may be referred to as a user interface of the control system herein. The control system may control the electric motor 122 to operate in a number of modes: passive, active-assisted, resistive, and active. The passive mode may refer to the electric motor 122 independently driving the one or more radially-adjustable couplings 124 rotationally coupled to the one or more pedals 110. In the passive mode, the electric motor 122 may be the only source of driving force on the radially-adjustable couplings 124. That is, the user may engage the pedals 110 with their hands or their feet and the electric motor 122 may rotate the radially-adjustable couplings 124 for the user. This may enable moving the affected body part and stretching the affected body part without the user exerting excessive force.

The active-assisted mode may refer to the electric motor 122 receiving measurements of revolutions per minute of the one or more radially-adjustable couplings 124, and causing the electric motor 122 to drive the one or more radially-adjustable couplings 124 rotationally coupled to the one or more pedals 110 when the measured revolutions per minute satisfy a threshold condition. The threshold condition may be configurable by the user and/or the physician. The electric motor 122 may be powered off while the user provides the driving force to the radially-adjustable couplings 124 as long as the revolutions per minute are above a revolutions per minute threshold and the threshold condition is not satisfied. When the revolutions per minute are less than the revolutions per minute threshold then the threshold condition is satisfied and the electric motor 122 may be controlled to drive the radially-adjustable couplings 124 to maintain the revolutions per minute threshold.

The resistive mode may refer to the electric motor 122 providing resistance to rotation of the one or more radially-adjustable couplings 124 coupled to the one or more pedals 110. The resistive mode may increase the strength of the body part undergoing prehabilitation by causing the muscle to exert force to move the pedals against the resistance provided by the electric motor 122.

The active mode may refer to the electric motor 122 powering off to provide no driving force assistance to the radially-adjustable couplings 124. Instead, in this mode, the user provides the sole driving force of the radially-adjustable couplings 124 using their hands or feet, for example.

During one or more of the modes, each of the pedals 110 may measure force exerted by a part of the body of the user on the pedal 110. For example, the pedals 110 may each contain any suitable sensor (e.g., strain gauge load cell, piezoelectric crystal, hydraulic load cell, etc.) for measuring force exerted on the pedal 110. Further, the pedals 110 may each contain any suitable sensor for detecting whether the body part of the user separates from contact with the pedals 110. In some embodiments, the measured force may be used to detect whether the body part has separated from the pedals 110. The force detected may be transmitted via the network interface card of the pedal 110 to the control system (e.g., computing device 102 and/or motor controller 120). As described further below, the control system may modify a parameter of operating the electric motor 122 based on the measured force. Further, the control system may perform one or more preventative actions (e.g., locking the electric motor 122 to stop the radially-adjustable couplings 124 from moving, slowing down the electric motor 122, presenting a notification to the user, etc.) when the body part is detected as separated from the pedals 110, among other things.

The goniometer 106 may be configured to measure angles of extension and/or bend of body parts and transmit the measured angles to the computing device 102 and/or the computing device 114. The goniometer 106 may be included in an electronic device that includes the one or more processing devices, memory devices, and/or network interface cards. The goniometer 106 may be disposed in a cavity of a mechanical brace. The cavity of the mechanical brace may be located near a center of the mechanical brace where the mechanical brace affords to bend and extend. The mechanical brace may be configured to secure to an upper body part (e.g., leg, arm, etc.) and a lower body part (e.g., leg, arm, etc.) to measure the angles of bend as the body parts are extended away from one another or retracted closer to one another.

The wristband 108 may include a 3-axis accelerometer to track motion in the X, Y, and Z directions, an altimeter for measuring altitude, and/or a gyroscope to measure orientation and rotation. The accelerometer, altimeter, and/or gyroscope may be operatively coupled to a processing device in the wristband 108 and may transmit data to the processing device. The processing device may cause a network interface card to transmit the data to the computing device 102 and the computing device 102 may use the data representing acceleration, frequency, duration, intensity, and patterns of movement to track steps taken by the user over certain time periods (e.g., days, weeks, etc.). The computing device 102 may transmit the steps to the computing device 114 executing a clinical portal 126. Additionally, in some embodiments, the processing device of the wristband 108 may determine the steps taken and transmit the steps to the computing device 102. In some embodiments, the wristband 108 may use photo plethysmography (PPG) to measure heartrate that detects an amount of red light or green light on the skin of the wrist. For example, blood may absorb green light so when the heart beats, the blood flow may absorb more green light, thereby enabling detecting heartrate. The heartrate may be sent to the computing device 102 and/or the computing device 114.

The computing device 102 may present the steps taken by the user and/or the heartrate via respective graphical element on the user portal 118, as discussed further below. The computing device 102 may also use the steps taken and/or the heart rate to control a parameter of operating the electromechanical device 104. For example, if the heartrate exceeds a target heartrate for a pedaling session, the computing device 102 may control the electric motor 122 to reduce resistance being applied to rotation of the radially-adjustable couplings 124. In another example, if the steps taken are below a step threshold for a day, the treatment plan may increase the amount of time for one or more modes that the user in which the user is to operate the electromechanical device 104 to ensure the affected body part is getting sufficient movement.

In some embodiments, the cloud-based computing system 116 may include one or more servers 128 that form a distributed computing architecture. Each of the servers 128 may include one or more processing devices, memory devices, data storage, and/or network interface cards. The servers 128 may be in communication with one another via any suitable communication protocol. The servers 128 may store profiles for each of the users that use the electromechanical device 104. The profiles may include information about the users such as a treatment plan, the affected body part, any procedure the user had performed on the affected body part, health, age, race, measured data from the goniometer 106, measured data from the wristband 108, measured data from the pedals 110, user input received at the user portal 118 during operation of any of the modes of the treatment plan, a level of discomfort the user experiences before and after any of the modes, before and after session images of the affected body part, and so forth.

In some embodiments the cloud-based computing system 116 may include a training engine 130 that is capable of generating one or more machine learning models 132. The machine learning models 132 may be trained to generate treatment plans for the patients in response to receiving various inputs (e.g., a procedure performed on the patient, an affected body part the procedure was performed on, other health characteristics (age, race, fitness level, etc.). The one or more machine learning models 132 may be generated by the training engine 130 and may be implemented in computer instructions that are executable by one or more processing device of the training engine 130 and/or the servers 128. To generate the one or more machine learning models 132, the training engine 130 may train the one or more machine learning models 132. The training engine 130 may use a base data set of patient characteristics, treatment plans followed by the patient, and results of the treatment plan followed by the patients. The results may include information indicating whether the treatment plan led to full recovery of the affected body part, partial recover of the affect body part, or lack of recovery of the affected body part. The training engine 130 may be a rackmount server, a router computer, a personal computer, a portable digital assistant, a smartphone, a laptop computer, a tablet computer, a camera, a video camera, a netbook, a desktop computer, a media center, or any combination of the above. The one or more machine learning models 132 may refer to model artifacts that are created by the training engine 130 using training data that includes training inputs and corresponding target outputs. The training engine 130 may find patterns in the training data that map the training input to the target output, and generate the machine learning models 132 that capture these patterns. Although depicted separately from the computing device 102, in some embodiments, the training engine 130 and/or the machine learning models 132 may reside on the computing device 102 and/or the computing device 114.

The machine learning models 132 may include one or more of a neural network, such as an image classifier, recurrent neural network, convolutional network, generative adversarial network, a fully connected neural network, or some combination thereof, for example. In some embodiments, a machine learning model may be supported by a data structure such as a data model. For example, a data model may be a structural framework that is organized according to one or more schemata. A machine learning model may use the data model by applying one or more machine learning techniques to the data model to generate output values or to identify specific data points. In some embodiments, the machine learning models 132 may be composed of a single level of linear or non-linear operations or may include multiple levels of non-linear operations. For example, the machine learning model 132 may include numerous layers and/or hidden layers that perform calculations (e.g., dot products) using various neurons.

Figure 2A:
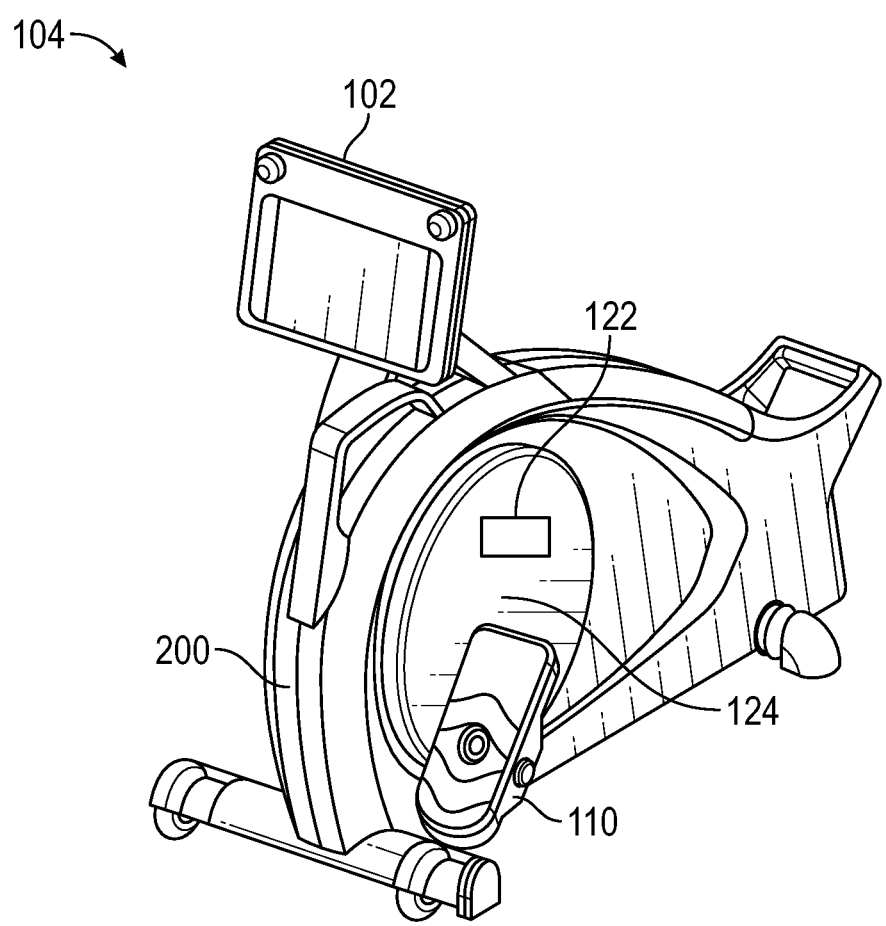
FIG. 2A generally illustrates a perspective view of an example of an exercise and prehabilitation device according to principles of the present disclosure.

FIG. 2A illustrates a perspective view of an example of a device used for prehabilitation, such as the electromechanical device 104, according to principles of the present disclosure. The electromechanical device 104 is shown having pedal 110 on opposite sides that are adjustably positionable relative to one another on respective radially-adjustable couplings 124. The electromechanical device 104 is configured as a small and portable unit so that it is easily transported to different locations at which prehabilitation or treatment is to be provided, such as at patients' homes, alternative care facilities, or the like. The patient may sit in a chair proximate the electromechanical device 104 to engage the device 104 with their feet, for example.

The electromechanical device 104 includes a rotary device such as radially-adjustable couplings 124 or flywheel or the like rotatably mounted such as by a central hub to a frame 16 or other support. The pedals 110 are configured for interacting with a patient to be rehabilitated and may be configured for use with lower body extremities such as the feet, legs, or upper body extremities, such as the hands, arms, and the like. For example, the pedal 110 may be a bicycle pedal of the type having a foot support rotatably mounted onto an axle with bearings. The axle may or may not have exposed end threads for engaging a mount on the radially-adjustable coupling 124 to locate the pedal on the radially-adjustable coupling 124. The radially-adjustable coupling 124 may include an actuator configured to radially adjust the location of the pedal to various positions on the radially-adjustable coupling 124.

The radially-adjustable coupling 124 may be configured to have both pedals 110 on opposite sides of a single coupling 124. In some embodiments, as depicted, a pair of radially-adjustable couplings 124 may be spaced apart from one another but interconnected to the electric motor 122. In the depicted example, the computing device 102 may be mounted on the frame 200 and may be detachable and held by the user while the user operates the device 104. The computing device 102 may present the user portal 118 and control the operation of the electric motor 122, as described herein.

Figure 2B:
FIG. 2B generally illustrates a perspective view of another example of an exercise and prehabilitation device according to principles of the present disclosure.

FIG. 2B generally illustrates a perspective view of another example of an exercise and prehabilitation device, such as the electromechanical device 104 according to principles of the present disclosure. The electromechanical device 104 takes the form of a traditional exercise/prehabilitation device which is more or less non-portable and remains in a fixed location, such as a prehabilitation clinic or medical practice. The electromechanical device 104 in FIG. 2B may include similar features described in FIG. 2A except the electromechanical device 104 in FIG. 2B includes a seat and is less portable.

Figure 3:
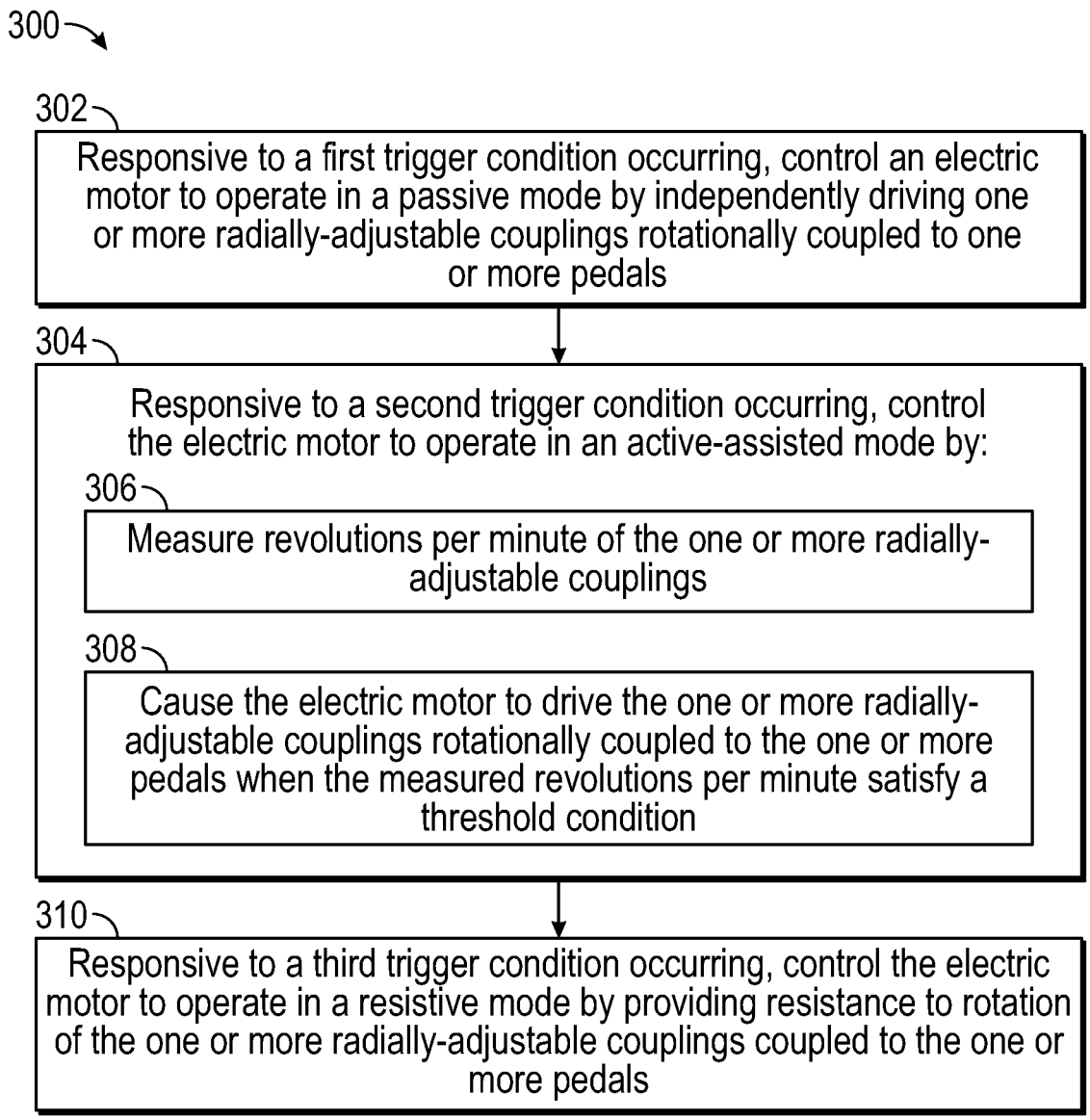
FIG. 3 generally illustrates example operations of a method for controlling an electromechanical device for prehabilitation in various modes according to principles of the present disclosure.

FIG. 3 generally illustrates example operations of a method 300 for controlling an electromechanical device 104 for prehabilitation in various modes according to principles of the present disclosure. The method 300 may be performed by processing logic that may include hardware (circuitry, dedicated logic, etc.), software, or a combination of both. The method 300 and/or each of their individual functions, subroutines, or operations may be performed by one or more processors of a control system (e.g., computing device 102 of FIG. 1) implementing the method 300. The method 300 may be implemented as computer instructions that, when executed by a processing device, execute the user portal 118. In certain implementations, the method 300 may be performed by a single processing thread. Alternatively, the method 300 may be performed by two or more processing threads, each thread implementing one or more individual functions, routines, subroutines, or operations of the methods. Various operations of the method 300 may be performed by one or more of the cloud-based computing system 116, the motor controller 120, the pedals 110, the goniometer 106, the wristband 108, and/or the computing device 114 of FIG. 1.

As discussed above, an electromechanical device 104 may include one or more pedals 110 coupled to one or more radially-adjustable couplings 124, an electric motor 122 coupled to the one or more pedals 110 via the one or more radially-adjustable couplings 124, and the control system including one or more processing devices operatively coupled to the electric motor 122. In some embodiments, the control system (e.g., computing device 102 and/or motor controller 120) may store instructions and one or more operations of the control system may be presented via the user portal 118. In some embodiments the radially-adjustable couplings 124 are configured for translating rotational motion of the electric motor 122 to radial motion of the pedals 110.

At block 302, responsive to a first trigger condition occurring, the processing device may control the electric motor 122 to operate in a passive mode by independently driving the one or more radially-adjustable couplings 124 rotationally coupled to the one or more pedals 110. "Independently drive" may refer to the electric motor 122 driving the one or more radially-adjustable couplings 124 without the aid of another driving source (e.g., the user). The first trigger condition may include an initiation of a pedaling session via the user interface of the control system, a period of time elapsing, a detected physical condition (e.g., heartrate, oxygen level, blood pressure, etc.) of a user operating the electromechanical device 104, a request received from the user via the user interface, or a request received via a computing device communicatively coupled to the control system (e.g., a request received from the computing device 114 executing the clinical portal 126). The processing device may control the electric motor 122 to independently drive the one or more radially-adjustable couplings 124 rotationally coupled to the one or more pedals 110 at a controlled speed specified in a treatment plan for a user operating the electromechanical device 104 while operating in the passive mode.

In some embodiments, the electromechanical device 104 may be configured such that the processor controls the electric motor 122 to individually drive the radially-adjustable couplings 124. For example, the processing device may control the electric motor 122 to individually drive the left or right radially-adjustable coupling, while allowing the user to provide the force to drive the other radially-adjustable coupling. As another example, the processing device may control the electric motor 122 to drive both the left and right radially-adjustable couplings but at different speeds. This granularity of control may be beneficial by controlling the speed at which a healing body part is moved (e.g., rotated, flexed, extended, etc.) to avoid tearing tendons or causing pain to the user.

At block 304, responsive to a second trigger condition occurring, the processing device may control the electric motor 122 to operate in an active-assisted mode by measuring (block 306) revolutions per minute of the one or more radially-adjustable couplings 124, and causing (block 308) the electric motor 122 to drive the one or more radially-adjustable couplings 124 rotationally coupled to the one or more pedals 110 when the measured revolutions per minute satisfy a threshold condition. The second trigger condition may include an initiation of a pedaling session via the user interface of the control system, a period of time elapsing, a detected physical condition (e.g., heartrate, oxygen level, blood pressure, etc.) of a user operating the electromechanical device 104, a request received from the user via the user interface, or a request received via a computing device communicatively coupled to the control system (e.g., a request received from the computing device 114 executing the clinical portal 126). The threshold condition may be satisfied when the measured revolutions per minute are less than a minimum revolutions per minute. In such an instance, the electric motor 122 may begin driving the one or more radially-adjustable couplings 124 to increase the revolutions per minute of the radially-adjustable couplings 124.

As with the passive mode, the processing device may control the electric motor 122 to individually drive the one or more radially-adjustable couplings 124 in the active-assisted mode. For example, if just a right knee is being rehabilitated, the revolutions per minute of the right radially-adjustable coupling 124 may be measured and the processing device may control the electric motor 122 to individually drive the right radially-adjustable coupling 124 when the measured revolutions per minute is less than the minimum revolutions per minute. In some embodiments, there may be different minimum revolution per minutes set for the left radially-adjustable coupling and the right radially-adjustable coupling, and the processing device may control the electric motor 122 to individually drive the left radially-adjustable coupling and the right radially-adjustable coupling as appropriate to maintain the different minimum revolutions per minute.

At block 310, responsive to a third trigger condition occurring, the processing device may control the electric motor 122 to operate in a resistive mode by providing resistance to rotation of the one or more radially-adjustable couplings 124 coupled to the one or more pedals 110. The third trigger condition may include an initiation of a pedaling session via the user interface of the control system, a period of time elapsing, a detected physical condition (e.g., heartrate, oxygen level, blood pressure, etc.) of a user operating the electromechanical device 104, a request received from the user via the user interface, or a request received via a computing device communicatively coupled to the control system (e.g., a request received from the computing device 114 executing the clinical portal 126).

In some embodiments, responsive to a fourth trigger condition occurring, the processing device is further configured to control the electric motor 122 to operate in an active mode by powering off to enable another source (e.g., the user) to drive the one or more radially-adjustable couplings 124 via the one or more pedals 110. In the active mode, another source may drive the one or more radially-adjustable couplings 124 via the one or more pedals 110 at any desired speed.

In some embodiments, the processing device may control the electric motor 122 to operate in each of the passive mode, the active-assisted mode, the resistive mode, and/or the active mode for a respective period of time during a pedaling session based on a treatment plan for a user operating the electromechanical device 104. In some embodiments, the various modes and the respective periods of time may be selected by a clinician that sets up the treatment plan using the clinical portal 126. In some embodiments, the various modes and the respective periods of time may be selected by a machine learning model trained to receive parameters (e.g., procedure performed on the user, body part on which the procedure was performed, health of the user) and to output a treatment plan to rehabilitate the affected body part, as described above.

In some embodiments, the processing device may modify one or more positions of the one or more pedals 110 on the one or more radially-adjustable couplings 124 to change one or more diameters of ranges of motion of the one or more pedals 110 during any of the passive mode, active-assisted mode, the resistive mode, and/or the active mode throughout a pedaling session for a user operating the electromechanical device 104. The processing device may be further configured to modify the position of one of the one or more pedals 110 on one of the one or more radially-adjustable couplings 124 to change the diameter of the range of motion of the one of the one or more pedals 110 while maintaining another position of another of the one or more pedals 110 on another of the one or more radially-adjustable couplings 124 to maintain another diameter of another range of motion of the another pedal. In some embodiments, the processing device may cause both positions of the pedals 110 to move to change the diameter of the range of motion for both pedals 110. The amount of movement of the positions of the pedals 110 may be individually controlled in order to provide different diameters of ranges of motions of the pedals 110 as desired.

In some embodiments, the processing device may receive, from the goniometer 106 worn by the user operating the electromechanical device 104, at least one of an angle of extension of a joint of the user during a pedaling session or an angle of bend of the joint of the user during the pedaling session. In some instances, the joint may be a knee or an elbow. The goniometer 106 may be measuring the angles of bend and/or extension of the joint and continuously or periodically transmitting the angle measurements that are received by the processing device. The processing device may modify the positions of the pedals 110 on the radially-adjustable couplings 124 to change the diameters of the ranges of motion of the pedals 110 based on the at least one of the angle of extension of the joint of the user or the angle of bend of the joint of the user.

In some embodiments, the processing device may receive, from the goniometer 106 worn by the user, a set of angles of extension between an upper leg and a lower leg at a knee of the user as the user extends the lower leg away from the upper leg via the knee. In some embodiments, the goniometer 106 may send the set of angles of extension between an upper arm, upper body, etc. and a lower arm, lower body, etc. The processing device may present, on a user interface of the control system, a graphical animation of the upper leg, the lower leg, and the knee of the user as the lower leg is extended away from the upper leg via the knee. The graphical animation may include the set of angles of extension as the set of angles of extension change during the extension. The processing device may store, in a data store of the control system, a lowest value of the set of angles of extension as an extension statistic for an extension session. A set of extension statistics may be stored for a set of extension sessions specified by the treatment plan. The processing device may present progress of the set of extension sessions throughout the treatment plan via a graphical element (e.g., line graph, bar chart, etc.) on the user interface presenting the set of extension statistics.

In some embodiments, the processing device may receive, from the goniometer 106 worn by the user, a set of angles of bend or flex between an upper leg and a lower leg at a knee of the user as the user retracts the lower leg closer to the upper leg via the knee. In some embodiments, the goniometer 106 may send the set of angles of bend between an upper arm, upper body, etc. and a lower arm, lower body, etc. The processing device may present, on a user interface of the control system, a graphical animation of the upper leg, the lower leg, and the knee of the user as the lower leg is retracted closer to the upper leg via the knee. The graphical animation may include the set of angles of bend as the set of angles of bend change during the bending. The processing device may store, in a data store of the control system, a highest value of the set of angles of bend as a bend statistic for a bend session. A set of bend statistics may be stored for a set of bend sessions specified by the treatment plan. The processing device may present progress of the set of bend sessions throughout the treatment plan via a graphical element (e.g., line graph, bar chart, etc.) on the user interface presenting the set of bend statistics.

In some embodiments, the angles of extension and/or bend of the joint may be transmitted by the goniometer 106 to the computing device 114 executing the clinical portal 126. A clinician may be operating the computing device 114 executing the clinical portal 126. The clinical portal 126 may present a graphical animation of the upper leg extending away from the lower leg and/or the upper leg bending closer to the lower leg in real-time during a pedaling session, extension session, and/or a bend session of the user. In some embodiments, the clinician portal 126 may provide notifications to the computing device 102 to present via the user portal 118. The notifications may indicate that the user has satisfied a target extension and/or bend angle. Other notifications may indicate that the user has extended or retracted a body part too far and should cease the extension and/or bend session. In some embodiments, the computing device 114 executing the clinical portal 126 may transmit a control signal to the control system to move a position of a pedal 110 on the radially-adjustable coupling 124 based on the angle of extension or angle of bend received from the goniometer 106. That is, the clinician can increase a diameter of range of motion for a body part of the user in real-time based on the measured angles of extension and/or bend during a pedaling session. This may enable the clinician dynamically control the pedaling session to enhance the prehabilitation results of the pedaling session.

In some embodiments, the processing device may receive, from a wearable device (e.g., wristband 108), an amount of steps taken by a user over a certain time period (e.g., day, week, etc.). The processing device may calculate whether the amount of steps satisfies a step threshold of a walking session of a treatment plan for the user. The processing device may present the amount of steps taken by the user on a user interface of the control system and may present an indication of whether the amount of steps satisfies the step threshold.

The wristband 108 may also measure one or more vital statistics of the user, such as a heartrate, oxygen level, blood pressure, and the like. The measurements of the vital statistics may be performed at any suitable time, such as during a pedaling session, walking session, extension session, and/or bend session. The wristband 108 may transmit the one or more vital statistics to the control system. The processing device of the control system may use the vital statistics to determine whether to reduce resistance the electric motor 122 is providing to lower one of the vital statistics (e.g., heartrate) when that vital statistic is above a threshold, to determine whether the user is in pain when one of the vital statistics is elevated beyond a threshold, to determine whether to provide a notification indicating the user should take a break or increase the intensity of the appropriate session, and so forth.

In some embodiments, the processing device may receive a request to stop the one or more pedals 110 from moving. The request may be received by a user selecting a graphical icon representing "stop" on the user portal 118 of the control system. The processing device may cause the electric motor 122 to lock and stop the one or more pedals from moving over a configured period of time (e.g., instantly, over 1 second, 2 seconds, 3 seconds, 5 seconds, 10 seconds, etc.). One benefit of including an electric motor 122 in the electromechanical device 104 is the ability to stop the movement of the pedals 110 as soon as a user desires.

In some embodiments, the processing device may receive, from one or more force sensors operatively coupled to the one or more pedals and the one or more processing devices, one or more measurements of force on the one or more pedals. The force sensors may be operatively coupled with the one or more processing devices via a wireless connection (e.g., Bluetooth) provided by wireless circuitry of the pedals. The processing device may determine whether the user has fallen from the electromechanical device 104 based on the one or more measurements of force. Responsive to determining that the user has fallen from the electromechanical device 104, the processing device may lock the electric motor 122 to stop the one or more pedals 110 from moving.

Additionally or alternatively, the processing device may determine that feet or hands have separated from the pedals 110 based on the one or more measurements of force. In response to determining that the feed or hands have separated from the pedals 110, the processing device may lock the electric motor 122 to stop the one or more pedals 110 from moving. Also, the processing device may present a notification on a user interface of the control system that instructs the user to place their feet or hands in contact with the pedals 110.

In some embodiments, the processing device may receive, from the force sensors operatively coupled to the one or more pedals 110, the measurements of force exerted by a user on the pedals 110 during a pedaling session. The processing device may present the respective measurements of force on each of the pedals 110 on a separate respective graphical scale on the user interface of the control system while the user pedals during the pedaling session. Various graphical indicators may be presented on the user interface to indicate when the force is below a threshold target range, within the threshold target range, and/or exceeds the threshold target range. Notifications may be presented to encourage the user to apply more force and/or less force to achieve the threshold target range of force. For example, the processing device is to present a first notification on the user interface when the one or more measurements of force satisfy a pressure threshold and present a second notification on the user interface when the one or more measurements do not satisfy the pressure threshold.

In addition, the processing device may provide an indicator to the user based on the one or more measurements of force. The indicator may include at least one of (1) providing haptic feedback in the pedals, handles, and/or seat of the electromechanical device 104, (2) providing visual feedback on the user interface (e.g., an alert, a light, a sign, etc.), (3) providing audio feedback via an audio subsystem (e.g., speaker) of the electromechanical device 104, or (4) illuminating a warning light of the electromechanical device 104.

In some embodiments, the processing device may receive, from an accelerometer of the control system, motor controller 120, pedal 110, or the like, a measurement of acceleration of movement of the electromechanical device 104. The processing device may determine whether the electromechanical device 104 has moved excessively relative to a vertical axis (e.g., fallen over) based on the measurement of acceleration. Responsive to determining that the electromechanical device 104 has moved excessively relative to the vertical axis based on the measurement of acceleration, the processing device may lock the electric motor 122 to stop the one or more pedals 110 from moving.

After a pedaling session is complete, the processing device may lock the electric motor 122 to prevent the one or more pedals from moving a certain amount of time after the completion of the pedaling session. This may enable healing of the body part being rehabilitated and prevent strain on that body part by excessive movement. Upon expiration of the certain amount of time, the processing device may unlock the electric motor 122 to enable movement of the pedals 110 again.

The user portal 118 may provide an option to image the body part being rehabilitated. For example, the user may place the body part within an image capture section of the user portal 118 and select an icon to capture an image of the body part. The images may be captured before and after a pedaling session, walking session, extension session, and/or bend session. These images may be sent to the cloud-based computing system to use as training data for the machine learning model to determine the effects of the session. Further, the images may be sent to the computing device 114 executing the clinical portal 126 to enable the clinician to view the results of the sessions and modify the treatment plan if desired and/or provide notifications (e.g., reduce resistance, increase resistance, extend the joint further or less, etc.) to the user if desired.

Figure 4:
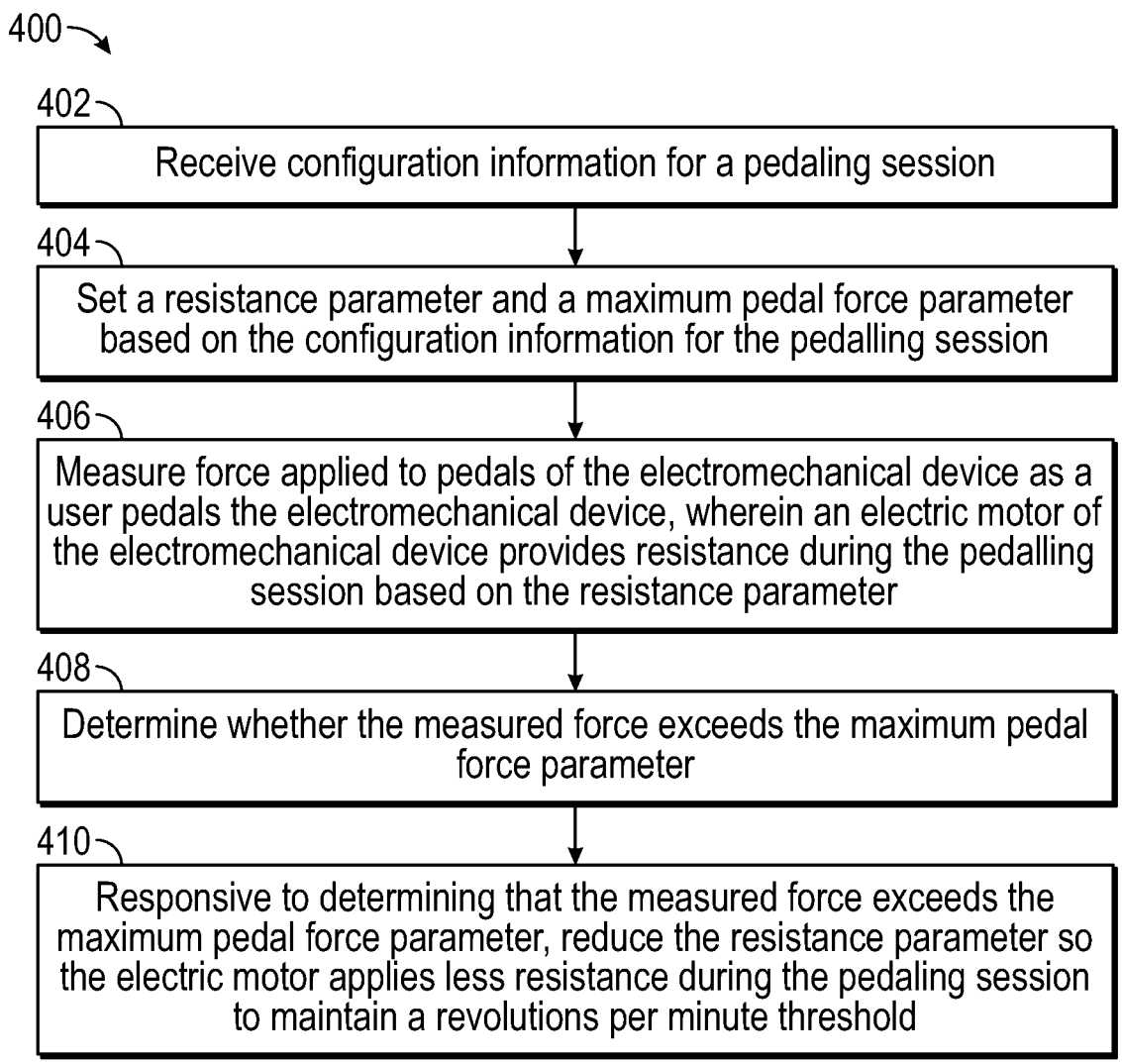
FIG. 4 generally illustrates example operations of a method for controlling an amount of resistance provided by an electromechanical device according to principles of the present disclosure.

FIG. 4 generally illustrates example operations of a method 400 for controlling an amount of resistance provided by an electromechanical device 104 according to principles of the present disclosure. Method 400 includes operations performed by processing devices of the control system (e.g., computing device 102) of FIG. 1. In some embodiments, one or more operations of the method 400 are implemented in computer instructions that, when executed by a processing device, execute the control system and/or the user portal 118. Various operations of the method 400 may be performed by one or more of the computing device 114, the cloud-based computing system 116, the motor controller 120, the pedal 110, the goniometer 106, and/or the wristband 108. The method 400 may be performed in the same or a similar manner as described above in regards to method 300.

At block 402, the processing device may receive configuration information for a pedaling session. The configuration information may be received via selection by the user on the user portal 118 executing on the computing device 102, received from the computing device 114 executing the clinical portal 126, downloaded from the cloud-based computing system 116, retrieved from a memory device of the computing device 102 executing the user portal 118, or some combination thereof. For example, the clinician may select the configuration information for a pedaling session of a patient using the clinical portal 126 and upload the configuration information from the computing device 114 to a server of the cloud-based computing system 116.

The configuration information for the pedaling session may specify one or more modes in which the electromechanical device 104 is to operate, and configuration information specific to each of the modes, an amount of time to operate each mode, and the like. For example, for a passive mode, the configuration information may specify a position for the pedal to be in on the radially-adjustable couplings 124 and a speed at which to control the electric motor 122. For the resistive mode, the configuration information may specify an amount of resistive force the electric motor 122 is to apply to rotation of radially-adjustable couplings 124 during the pedaling session, a maximum pedal force that is desired for the user to exert on each pedal 110 of the electromechanical device 104 during the pedaling session, and/or a revolutions per minute threshold for the radially-adjustable couplings 124. For the active-assisted mode, the configuration information may specify a minimum pedal force and a maximum pedal force that is desired for the user to exert on each pedal of the electromechanical device 104, a speed to operate the electric motor 122 at which to drive one or both of the radially-adjustable couplings 124, and so forth.

In some embodiments, responsive to receiving the configuration information, the processing device may determine that a trigger condition has occurred. The trigger condition may include receiving a selection of a mode from a user, an amount of time elapsing, receiving a command from the computing device 114 executing the clinical portal 126, or the like. The processing device may control, based on the trigger condition occurring, the electric motor 122 to operate in a resistive mode by providing a resistance to rotation of the pedals 110 based on the trigger condition.

At block 404, the processing device may set a resistance parameter and a maximum pedal force parameter based on the amount of resistive force and the maximum pedal force, respectively, included in the configuration information for the pedaling session. The resistance parameter and the maximum force parameter may be stored in a memory device of the computing device 102 and used to control the electric motor 122 during the pedaling session. For example, the processing device may transmit a control signal along with the resistance parameter and/or the maximum pedal force parameter to the motor controller 120, and the motor controller 120 may drive the electric motor 122 using at least the resistance parameter during the pedaling session.

At block 406, the processing device may measure force applied to pedals 110 of the electromechanical device 104 as a user operates (e.g., pedals) the electromechanical device 104. The electric motor 122 of the electromechanical device 104 may provide resistance during the pedaling session based on the resistance parameter. A force sensor disposed in each pedal 110 and operatively coupled to the motor controller 120 and/or the computing device 102 executing the user portal 118 may measure the force exerted on each pedal throughout the pedaling session. The force sensors may transmit the measured force to a processing device of the pedals 110, which in turn causes a communication device to transmit the measured force to the processing device of the motor controller 120 and/or the computing device 102.

At block 408, the processing device may determine whether the measured force exceeds the maximum pedal force parameter. The processing device may compare the measured force to the maximum pedal force parameter to make this determination.

At block 410, responsive to determining that the measured force exceeds the maximum pedal force parameter, the processing device may reduce the resistance parameter so the electric motor 122 applies less resistance during the pedaling session to maintain the revolutions per minute threshold specified in the configuration information. Reducing the resistance may enable the user to pedal faster, thereby increasing the revolutions per minute of the radially-adjustable couplings 124. Maintaining the revolutions per minute threshold may ensure that the patient is exercising the affected body part as rigorously as desired during the mode. In response to determining that the measured force does not exceed the maximum pedal force parameter, the processing device may maintain the same maximum pedal force parameter specified by the configuration information during the pedaling session.

In some embodiments, the processing device may determine than a second trigger condition has occurred. The second trigger condition may include receiving a selection of a mode from a user via the user portal 118, an amount of time elapsing, receiving a command from the computing device 114 executing the clinical portal 126, or the like. The processing device may control, based on the trigger condition occurring, the electric motor 122 to operate in a passive mode by independently driving one or more radially-adjustable couplings 124 coupled to the pedals 110 in a rotational fashion. The electric motor 122 may drive the one or more radially-adjustable couplings 124 at a speed specified in the configuration information without another driving source. Also, the electric motor 122 may drive each of the one or more radially-adjustable couplings 124 individually at different speeds.

In some embodiments, the processing device may determine that a third trigger condition has occurred. The third trigger condition may be similar to the other trigger conditions described herein. The processing device may control, based on the third trigger condition occurring, the electric motor 122 to operate in an active-assisted mode by measuring revolutions per minute of the one or more radially-adjustable couplings 124 coupled to the pedals 110 and causing the electric motor 122 to drive in a rotational fashion the one or more radially-adjustable couplings 124 coupled to the pedals 110 when the measured revolutions per minute satisfy a threshold condition.

In some embodiments, the processing device may receive, from the goniometer 106 worn by the user operating the electromechanical device 104, a set of angles of extension between an upper leg and a lower leg at a knee of the user. The set of angles are measured as the user extends the lower leg away from the upper leg via the knee. In some embodiments, the angles of extension may represent angles between extending a lower arm away from an upper arm at an elbow. Further, the processing device may receive, from the goniometer 106, a set of angles of bend between the upper leg and the lower leg at the knee of the user. The set of angles of bend are measured as the user retracts the lower leg closer to the upper leg via the knee. In some embodiments, the angles of bend represent angles between bending a lower arm closer to an upper arm at an elbow.

The processing device may determine whether a range of motion threshold condition is satisfied based on the set of angles of extension and the set of angles of bend. Responsive to determining that the range of motion threshold condition is satisfied, the processing device may modify a position of one of the pedals 110 on one of the radially-adjustable couplings 124 to change a diameter of a range of motion of the one of the pedals 110. Satisfying the range of motion threshold condition may indicate that the affected body part is strong enough or flexible enough to increase the range of motion allowed by the radially-adjustable couplings 124.

Figure 5:
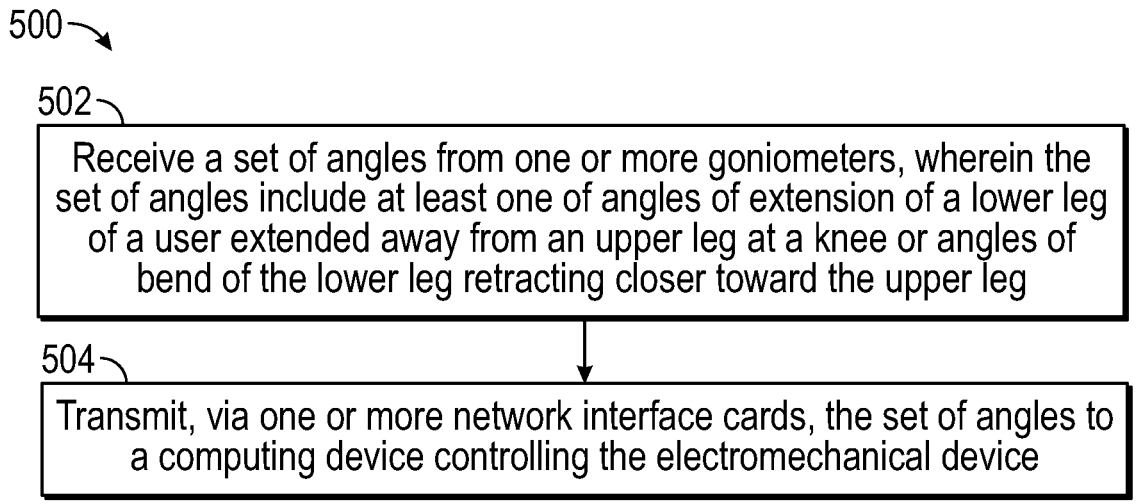
FIG. 5 generally illustrates example operations of a method for measuring angles of bend and/or extension of a lower leg relative to an upper leg using a goniometer according to principles of the present disclosure.

FIG. 5 generally illustrates example operations of a method 500 for measuring angles of bend and/or extension of a lower leg relative to an upper leg using the goniometer 106 according to principles of the present disclosure. In some embodiments, one or more operations of the method 500 are implemented in computer instructions that are executed by the processing devices of the goniometer 106. 106 of FIG. 1. The method 500 may be performed in the same or a similar manner as described above in regards to method 300.

At block 502, the processing device may receive a set of angles from the one or more goniometers 106. The goniometer 106 may measure angles of extension and/or bend between an upper body part (leg, arm, torso, neck, head, etc.) and a lower body part (leg, arm, torso, neck head, hand, feet, etc.) as the body parts are extended and/or bent during various sessions (e.g., pedaling session, walking session, extension session, bend session, etc.). The set of angles may be received while the user is pedaling one or more pedals 110 of the electromechanical device 104.

At block 504, the processing device may transmit, via one or more network interface cards, the set of angles to a computing device controlling the electromechanical device 104. The electromechanical device 104 may be operated by a user rehabilitating an affected body part. For example, the user may have recently had surgery to repair a second or third degree sprain of an anterior cruciate ligament (ACL). Accordingly, the goniometer 106 may be secured proximate to the knee around the upper and lower leg by the affected ACL.

In some embodiments, transmitting the set of angles to the computing device 102 controlling the electromechanical device 104 may cause the computing device 102 to adjust a position of one of one or more pedals 110 on the radially-adjustable coupling 124 based on the set of angles satisfying a range of motion threshold condition. The range of motion threshold condition may be set based on configuration information for a treatment plan received from the cloud-based computing system 116 or the computing device 114 executing the clinical portal 126. The position of the pedal 110 is adjusted to increase a diameter of a range of motion transited by an upper body part (e.g., leg), lower body part (e.g., leg), and a joint (e.g., knee) of the user as the user operates the pedal 110. In some embodiments, the position of the pedal 110 may be adjusted in real-time while the user is operating the electromechanical device 104. In some embodiments, the user portal 118 may present a notification to the user indicating that the position of the pedal 110 should be modified, and the user may modify the position of the pedal 110 and resume operating the electromechanical device 104 with the modified pedal position.

In some embodiments, transmitting the set of angles to the computing device 102 may cause the computing device 102 executing the user portal 118 to present the set of angles in a graphical animation of the lower body part and the upper body part moving in real-time during the extension or the bend. In some embodiments, the set of angles may be transmitted to the computing device 114 executing the clinical portal 126, and the clinical portal 126 may present the set of angles in a graphical animation of the lower body part and the upper body part moving in real-time during the extension or the bend. In addition, the set of angles may be presented in one or more graphs or charts on the clinical portal 126 and/or the user portal 118 to depict progress of the extension or bend for the user.

FIGS. 6-12 generally illustrate various detailed views of the components of the prehabilitation system disclosed herein.

Figure 6:
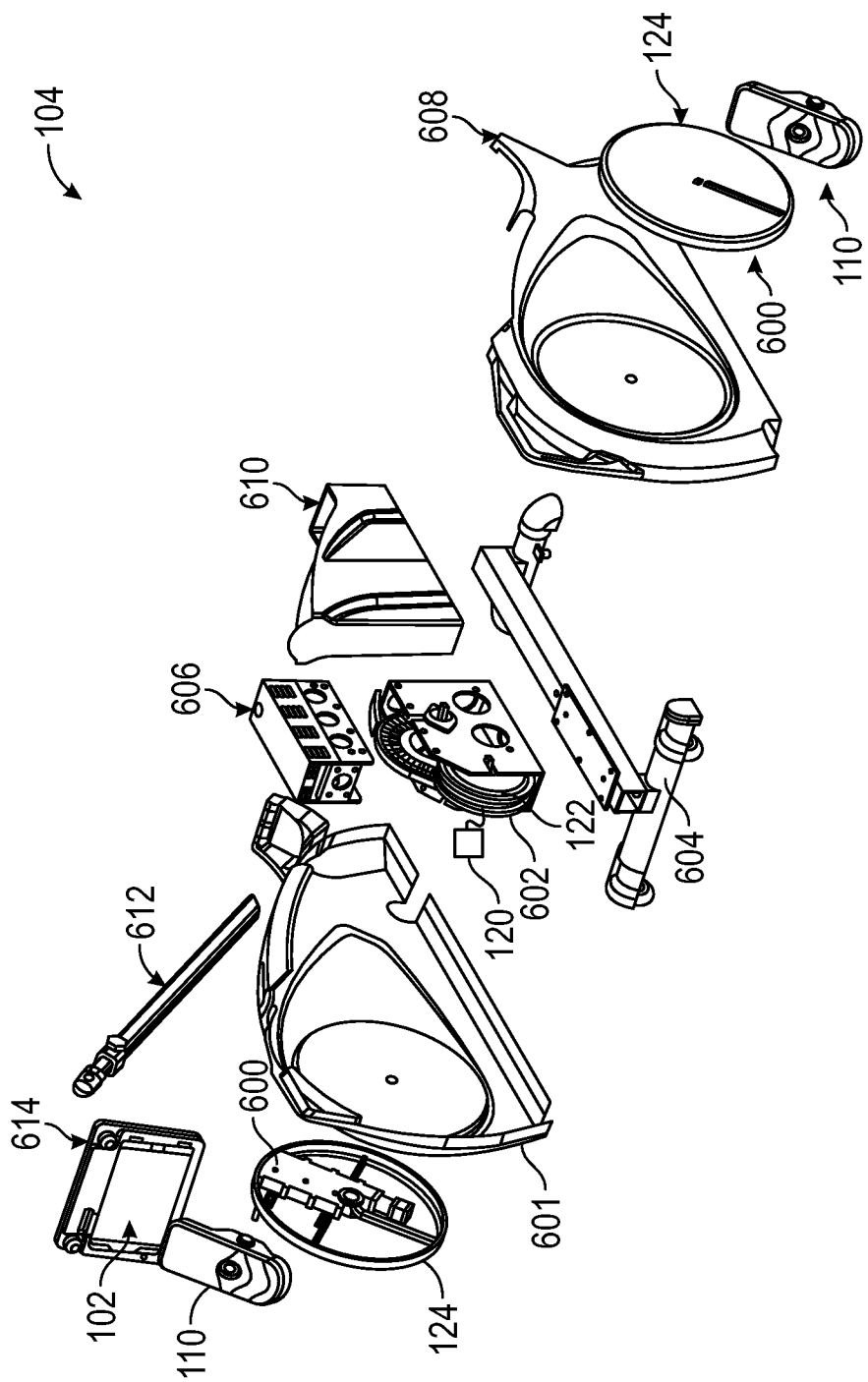
FIG. 6 generally illustrates an exploded view of components of the exercise and prehabilitation device according to principles of the present disclosure.

For example, FIG. 6 generally illustrates an exploded view of components of the electromechanical device 104 according to principles of the present disclosure. The electromechanical device 104 may include a pedal 110 that couples to a left radially-adjustable coupling via a left pedal arm assembly 600 disposed within a cavity of the left radially-adjustable coupling. The radially-adjustable coupling 124 may be disposed in a circular opening of a left outer cover 601 and the pedal arm assembly 600 may be secured to a drive sub-assembly 602. The drive sub-assembly 602 may include the electric motor 122 that is operatively coupled to the motor controller 120. The drive sub-assembly 602 may include one or more braking mechanisms, such as disk brakes, that enable instantaneously locking the electric motor 122 or stopping the electric motor 122 over a period of time. The electric motor 122 may be any suitable electric motor (e.g., a crystallite electric motor). The drive sub-assembly 602 may be secured to a frame sub-assembly 604. A top support sub-assembly 606 may be secured on top of the drive sub-assembly 602.

A right pedal 110 couples to a left radially-adjustable coupling 124 via a right pedal arm assembly 600 disposed within a cavity of the right radially-adjustable coupling 124. The right radially-adjustable coupling 124 may be disposed in a circular opening of a right outer cover 608 and the right pedal arm assembly 600 may be secured to the drive sub-assembly 602. An internal volume may be defined when the left outer cover 601 and the right outer cover 608 are secured together around the frame sub-assembly 604. The left outer cover 601 and the right outer cover 608 may also make up the frame of the device 104 when secured together. The drive sub-assembly 602, top support sub-assembly 606, and pedal arm assemblies 600 may be disposed within the internal volume upon assembly. A storage compartment 610 may be secured to the frame.

Further, a computing device arm assembly 612 may be secured to the frame and a computing device mount assembly 614 may be secured to an end of the computing device arm assembly 612. The computing device 102 may be attached or detached from the computing device mount assembly 614 as desired during operation of the device 104.

Figure 7:
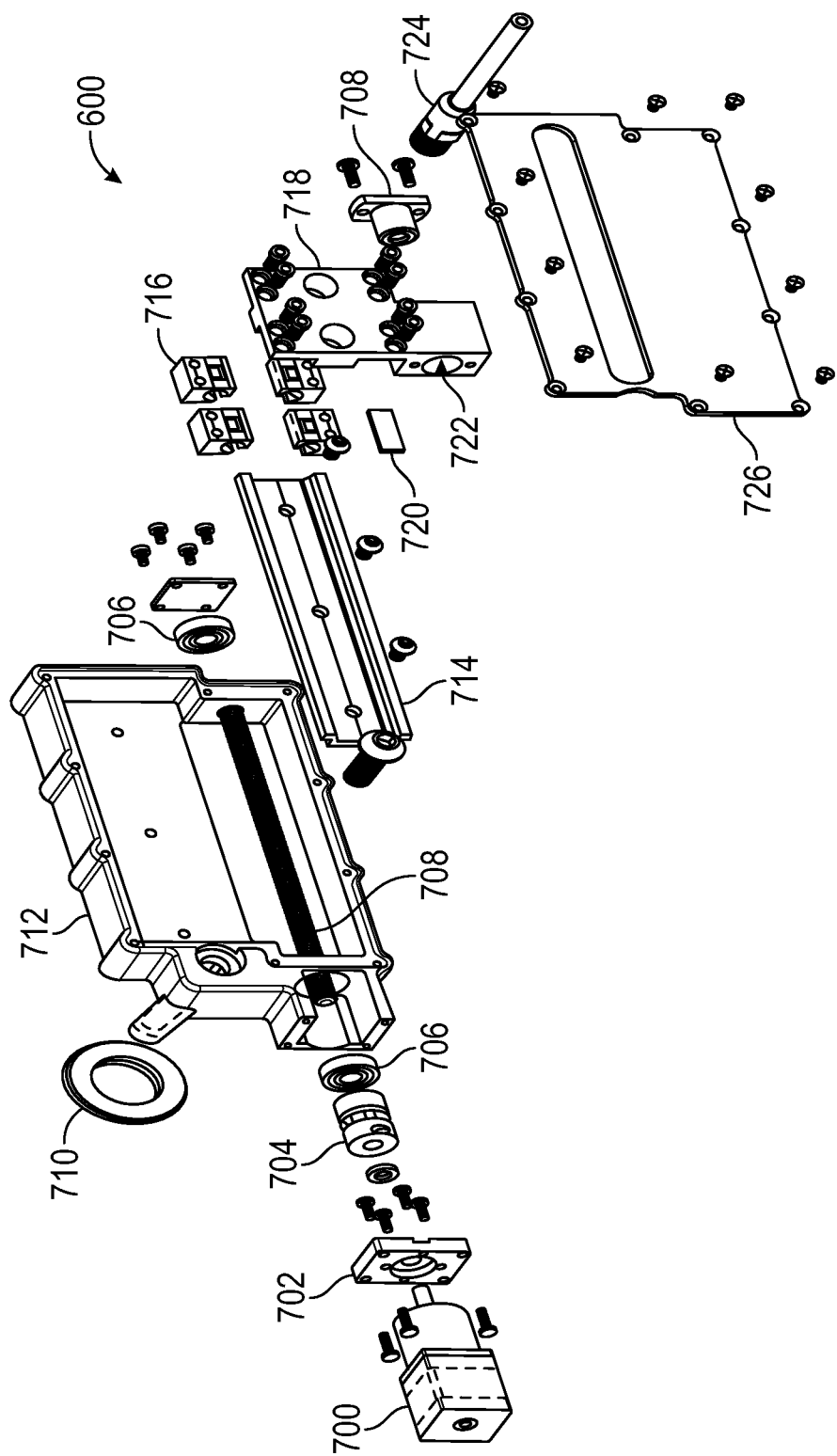
FIG. 7 generally illustrates an exploded view of a right pedal assembly according to principles of the present disclosure.

FIG. 7 generally illustrates an exploded view of a pedal assembly 600 according to principles of the present disclosure. The pedal assembly 600 includes a stepper motor 700. The stepper motor 700 may be any suitable stepper motor. The stepper motor 700 may include multiple coils organized in groups referred to as phases. Each phase may be energized in sequence to rotate the motor one step at a time. The control system may use the stepper motor 700 to move the position of the pedal 110 on the radially-adjustable coupling 124.

The stepper motor 700 includes a barrel and pin that are inserted through a hole in a motor mount 702. A shaft coupler 704 and a bearing 706 include through holes that receive an end of a first end leadscrew 708. The leadscrew 708 is disposed in a lower cavity of a pedal arm 712. The pin of the electric motor 122 may be inserted in the through holes of the shaft coupler 704 and the bearing 704 to secure to the first end of the leadscrew 708. The motor mount 702 may be secured to a frame of the pedal arm 712. Another bearing 706 may be disposed on another end of the leadscrew 708. An electric slip ring 710 may be disposed on the pedal arm 712.

A linear rail 714 is disposed in and secured to an upper cavity of the pedal arm 712. The linear rail 714 may be used to move the pedal to different positions as described further below. A number of linear bearing blocks 716 are disposed onto a top rib and a bottom rib of the linear rail 714 such that the bearing blocks 716 can slide on the ribs. A spindle carriage 718 is secured to each of the bearing blocks 716. A support bearing 720 is used to provide support. The lead screw may be inserted in through hole 722 of the spindle carriage 718. A lead screw unit 724 may be secured at an end of the through hole 722 to house an end of the lead screw 708. A spindle 724 is attached to a hole of the spindle carriage 718. The end of the spindle 724 protrudes through a hole of a pedal arm cover 726 when the pedal arm assembly 600 is assembled. When the stepper motor 700 turns on, the lead screw 708 can be rotated, thereby causing the spindle carriage 718 to move radially along the linear rail 714. As a result, the spindle 724 may radially traverse the opening of the pedal arm cover 726 as desired.

Figure 8:
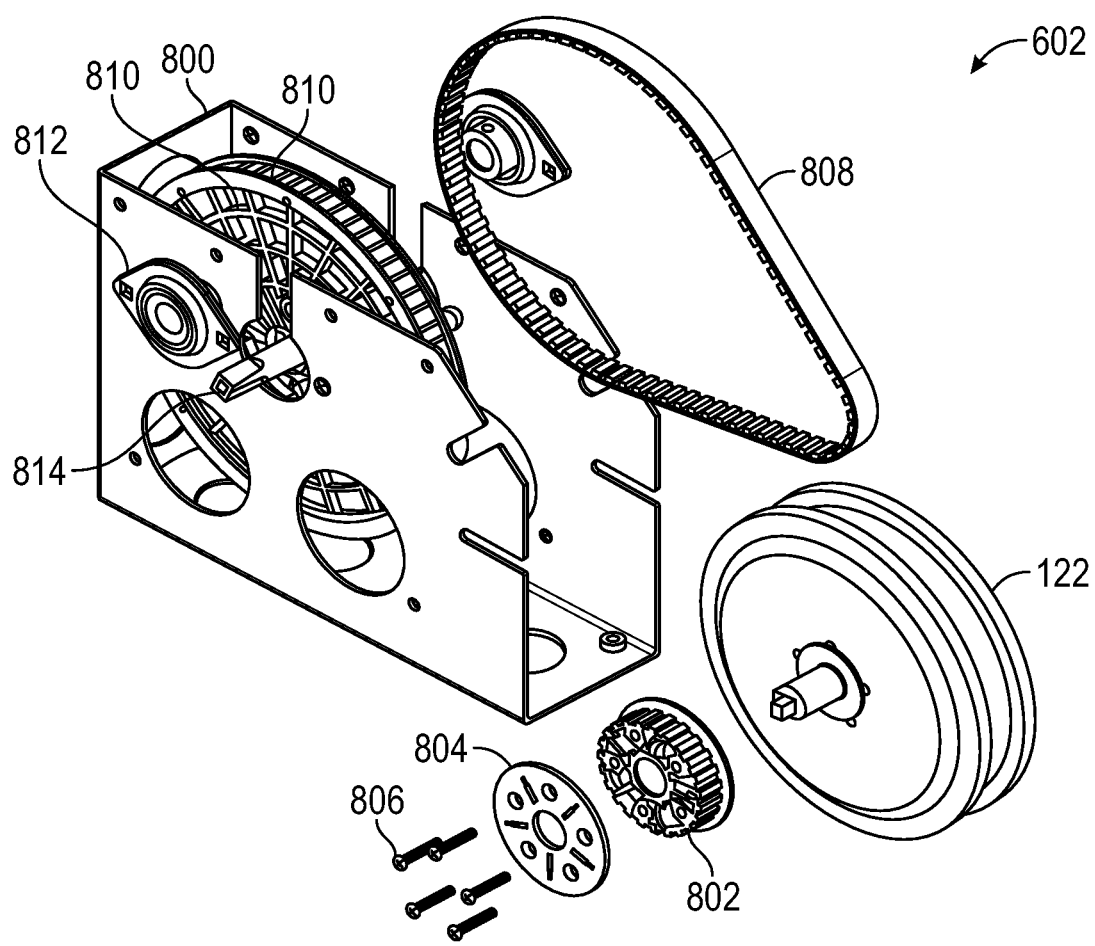
FIG. 8 generally illustrates an exploded view of a motor drive assembly according to principles of the present disclosure.

FIG. 8 generally illustrates an exploded view of a drive sub-assembly 602 according to principles of the present disclosure. The drive sub-assembly 602 includes an electric motor 122. The electric motor 122 is partially disposed in a crank bracket housing 800. A side of the electric motor 122 includes a small molded pulley 802 secured to it via a small pulley plate 804 by screws 806. Also disposed within the crank bracket housing 800 is a timing belt 808 and a large molded pulley 810. The timing belt 808 may include teeth on an interior side that engage with teeth on the small molded pulley 802 and the large molded pulley 810 to cause the large molded pulley 810 to rotate when the electric motor 122 operates. The crank bracket housing 800 includes mounted bearing 814 on both sides through which cranks 814 of the large molded pulley 810 protrude. The cranks 814 may be operatively coupled to the pedal assemblies.

Figure 9:
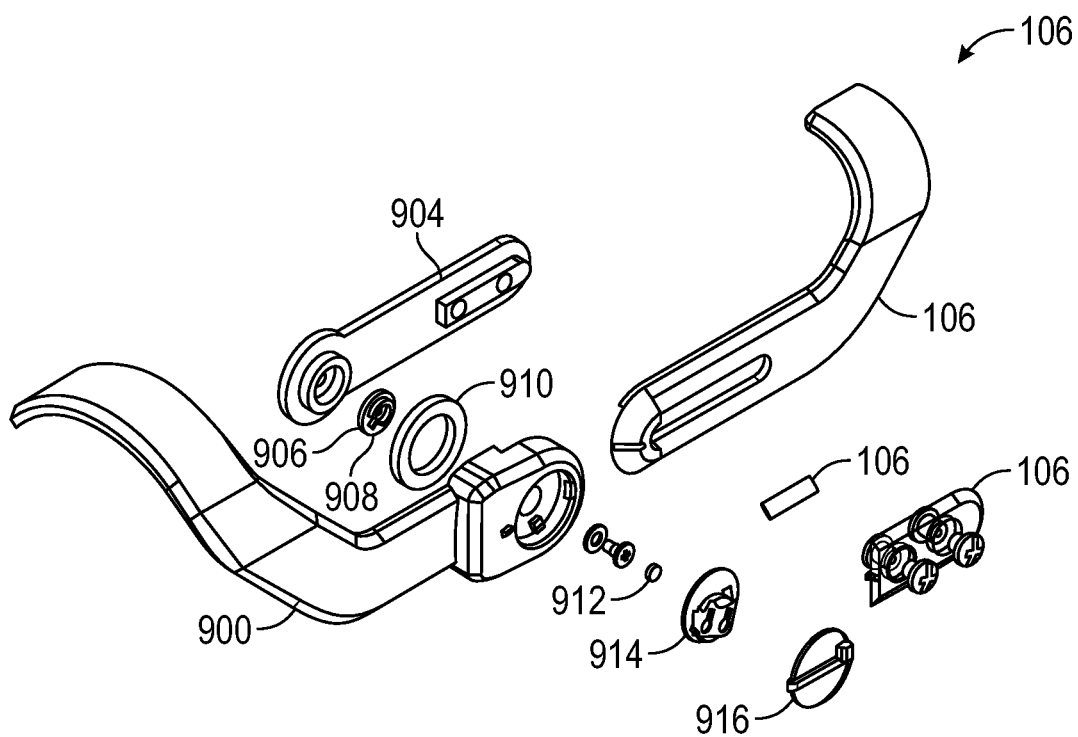
FIG. 9 generally illustrates an exploded view of a portion of a goniometer according to principles of the present disclosure.

FIG. 9 generally illustrates an exploded view of a portion of a goniometer 106 according to principles of the present disclosure. The goniometer 106 includes an upper section 900 and a lower section 902. The upper section 900 and the lower section 902 are rotatably coupled via a lower leg side brace 904. A bottom cap 906 is inserted into a protruded cavity of the lower leg side brace 904. In some embodiments the bottom cap 906 includes a microcontroller 908. A thrust roller bearing 910 fits over the protruded cavity of the lower leg side brace, which is inserted into a cavity of the upper section 900 and secured to the upper section 900 via a screw. Another cavity is located of the upper section 900 is on a side of the upper section 900 opposite to the side having the cavity with the inserted protruded cavity. A radial magnet 912 and a microcontroller (e.g., printed control board) 914 are disposed in another cavity and a top cap 916 is placed on top to cover the other cavity. The microcontroller 908 and/or the microcontroller 914 may include a network interface card or a radio configured to communicate via a short range wireless protocol (e.g., Bluetooth), a processing device, and a memory device. Further, either or both of the microcontrollers 908 and 914 may include a magnetic sensing encoder chip that senses the position of the radial magnet 912. The position of the radial magnet 912 may be used to determine an angle of bend or extension of the goniometer 106 by the processing device(s) of the microcontrollers 908 and/or 914. The angles of bend/extension may be transmitted via the radio to the computing device 102.

Figure 10:
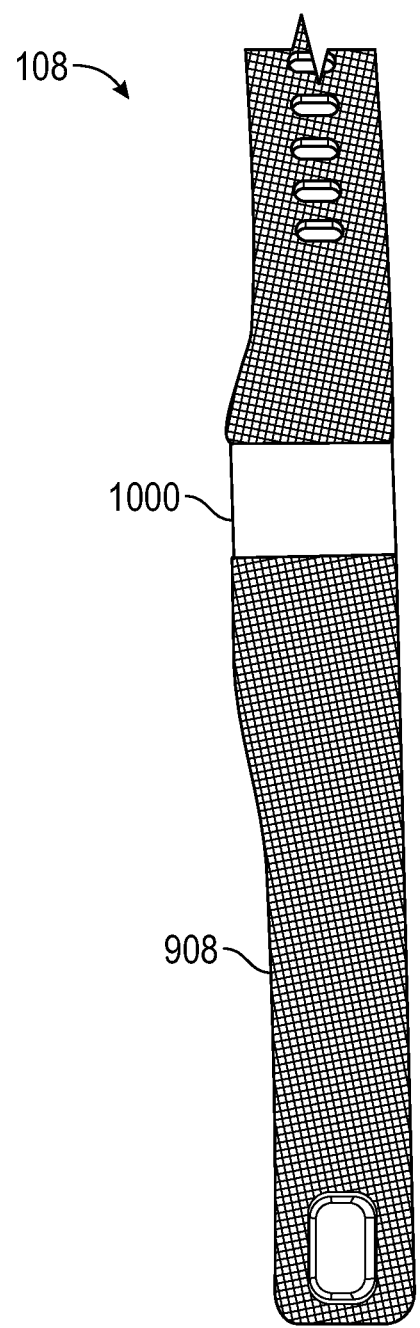
FIG. 10 generally illustrates a top view of a wristband according to principles of the present disclosure.

FIG. 10 generally illustrates a top view of a wristband 108 according to principles of the present disclosure. The wristband 108 includes a strap with a clasp to secure the strap to a wrist of a person. The wristband 108 may include one or more processing devices, memory devices, network interface cards, and so forth. The wristband 108 may include a display 1000 configured to present information measured by the wristband 108. The wristband 108 may include an accelerometer, gyroscope, and/or an altimeter, as discussed above. The wristband 108 may also include a light sensor to detect a heartrate of the user wearing the wristband 108. In some embodiments, the wristband 108 may include a pulse oximeter to measure an amount of oxygen (oxygen saturation) in the blood by sending infrared light into capillaries and measuring how much light is reflected off the gases. The wristband 108 may transmit the measurement data to the computing device 102.

Figure 11:
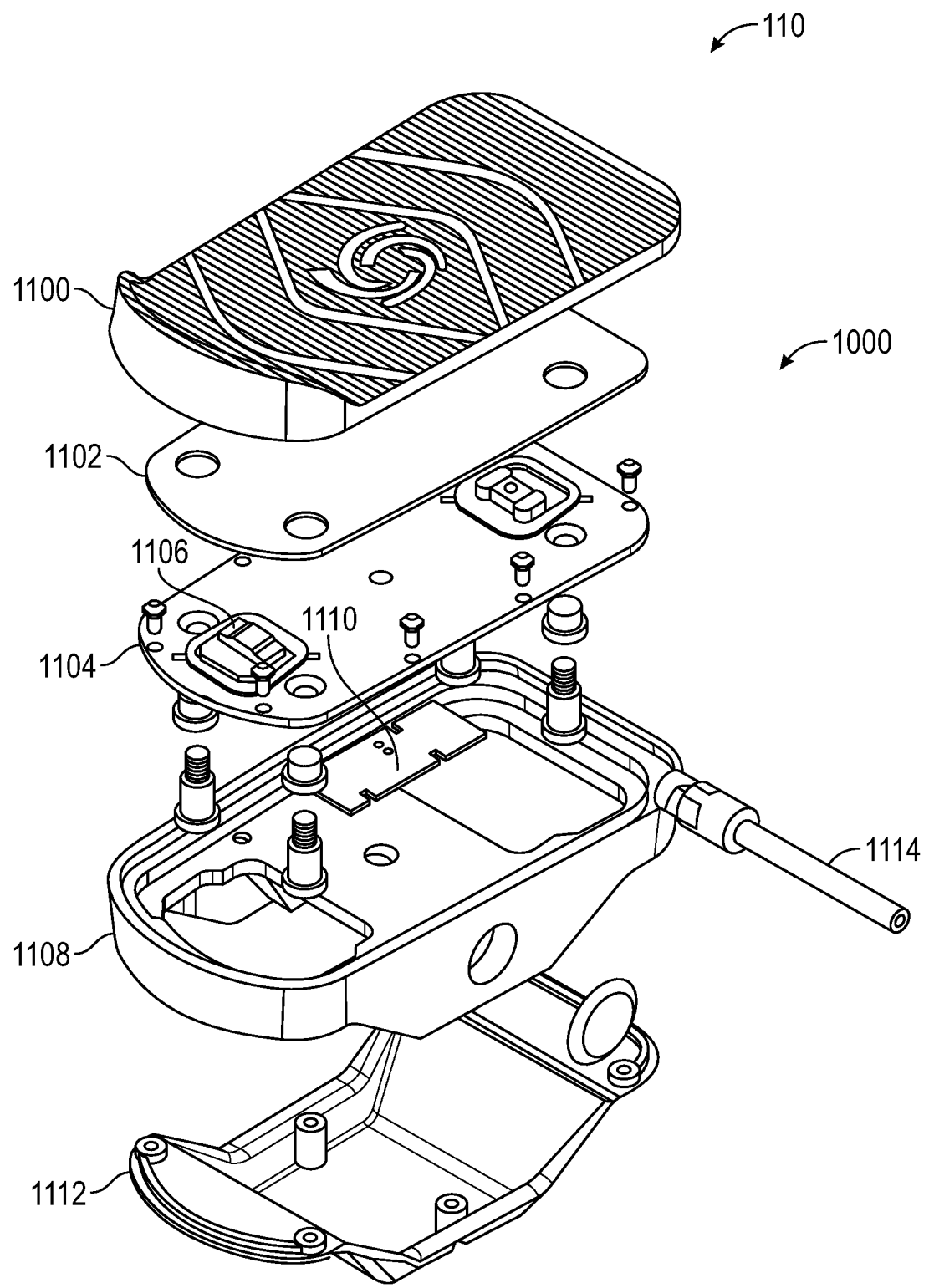
FIG. 11 generally illustrates an exploded view of a pedal according to principles of the present disclosure.

FIG. 11 generally illustrates an exploded view of a pedal 110 according to principles of the present disclosure. The pedal 110 includes a molded pedal top 1100 disposed on top of a molded pedal top support plate 1102. The molded pedal top 1100 and the molded pedal top support plate 1102 are secured to a molded pedal base plate 1104 via screws, for example. The molded pedal base plate 1104 includes a strain gauge 1106 configured to measure force exerted on the pedal 110. The pedal 110 also includes a molded pedal bottom 1108 where a microcontroller 1110 is disposed. The microcontroller 1110 may include processing devices, memory devices, and/or a network interface card or radio configured to communicate via a short range communication protocol, such as Bluetooth. The strain gauge 1106 is operatively coupled to the microcontroller 1110 and the strain gauge 1106 transmits the measured force to the microcontroller 1110. The microcontroller 1110 transmits the measured force to the computing device 102 and/or the motor controller 120 of the electromechanical device 104. The molded pedal top 1100, the molded pedal top support plate 1102, the molded pedal base plate 1104 are secured to the molded pedal bottom 1108, which is further secured to a molded pedal bottom cover 1112. The pedal 110 also includes a spindle 1114 that couples with the pedal arm assembly.

Figure 12:
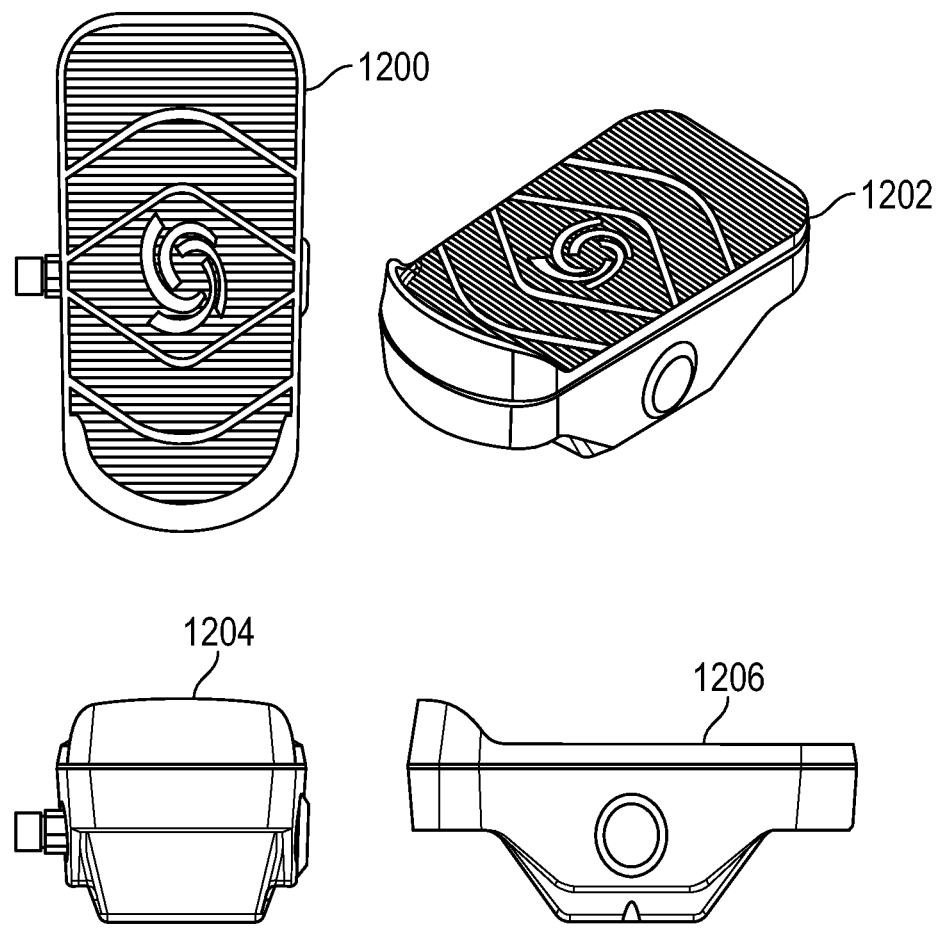
FIG. 12 generally illustrates additional views of the pedal according to principles of the present disclosure.

FIG. 12 generally illustrates additional views of the pedal according to principles of the present disclosure. A top view 1200 of the pedal is depicted, a perspective view 1202 of the pedal is depicted, a front view 1204 of the pedal is depicted, and a side view 1206 of the pedal is depicted.

FIGS. 13-29 generally illustrate different user interfaces of the user portal 118. A user may use the computing device 102, such as a tablet, to execute the user portal 118. In some embodiments, the user may hold the tablet in their hands and view the user portal 118 as they perform a pedaling session. Various user interfaces of the user portal 118 may provide prompts for the user to affirm that they are wearing the goniometer 106 and the wristband 108, and that their feet are on the pedals 110.

Figure 13:
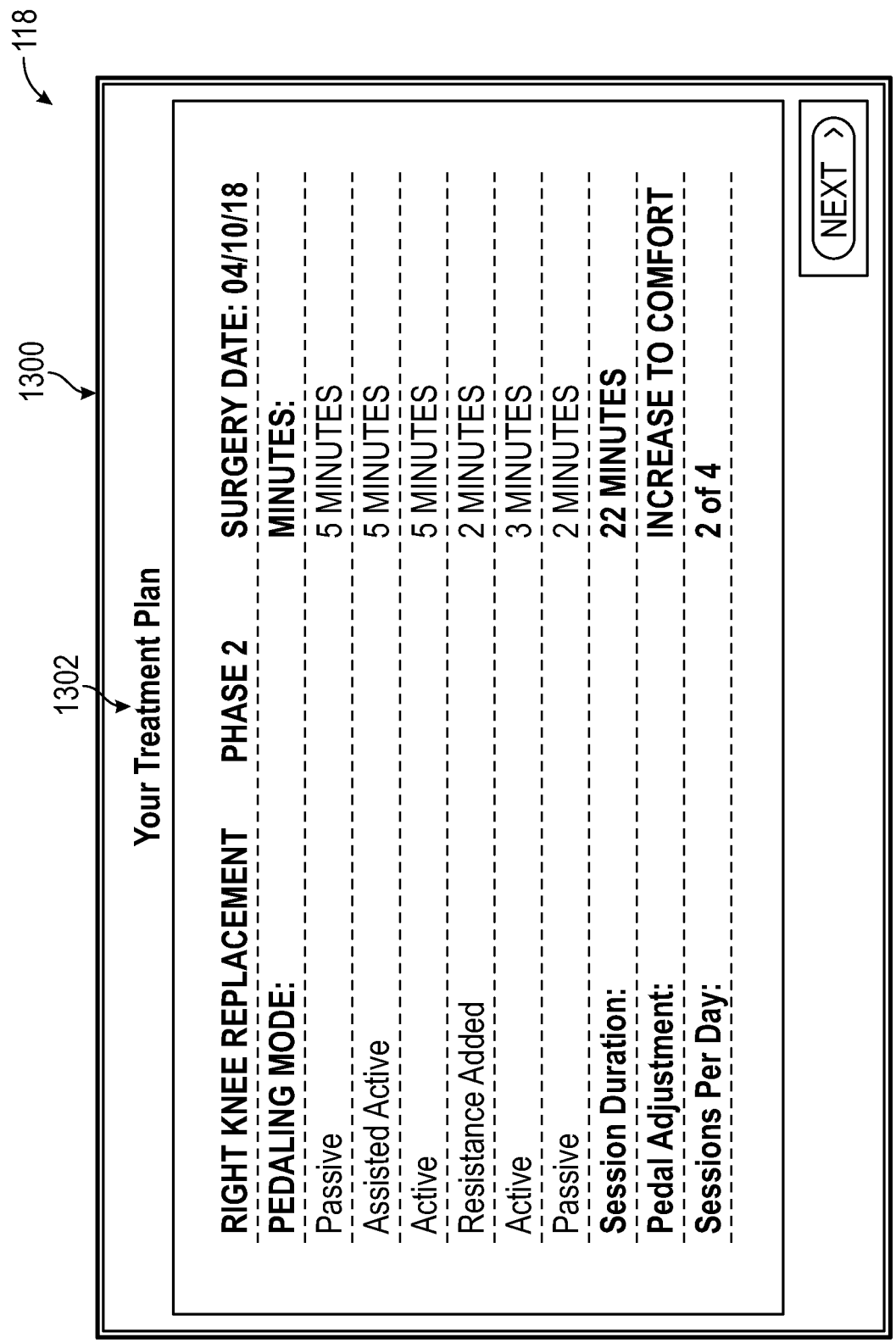
FIG. 13 generally illustrates an example user interface of the user portal, the user interface presenting a treatment plan for a user according to principles of the present disclosure.

FIG. 13 generally illustrates an example user interface 1300 of the user portal 118, the user interface 1300 presenting a treatment plan 1302 for a user according to principles of the present disclosure. The treatment plan 1302 may be received from the computing device 114 executing the clinical portal 126 and/or downloaded from the cloud-based computing system 116. The physician may have generated the treatment plan 1302 using the clinical portal 126 or the trained machine learning model(s) 132 may have generated the treatment plan 1302 for the user. As depicted, the treatment plan 1302 presents the type of procedure ("right knee replacement") that the patient underwent. Further, the treatment plan 1302 presents a pedaling session including a combination of the modes in which to operate the electromechanical device 104, as well as a respective set period of time for operating each of the modes. For example, the treatment plan 1302 indicates operating the electromechanical device 104 in a passive mode for 5 minutes, an active-assisted mode for 5 minutes, an active mode for 5 minutes, a resistive mode for 2 minutes, an active mode for 3 minutes, and a passive mode for 2 minutes. The total duration of the pedaling session is 22 minutes and the treatment plan 1302 also specifies that the position of the pedal may be set according to a comfort level of the patient. The user interface 1300 may be displayed as an introductory user interface prior to the user beginning the pedaling session.

Figure 14:
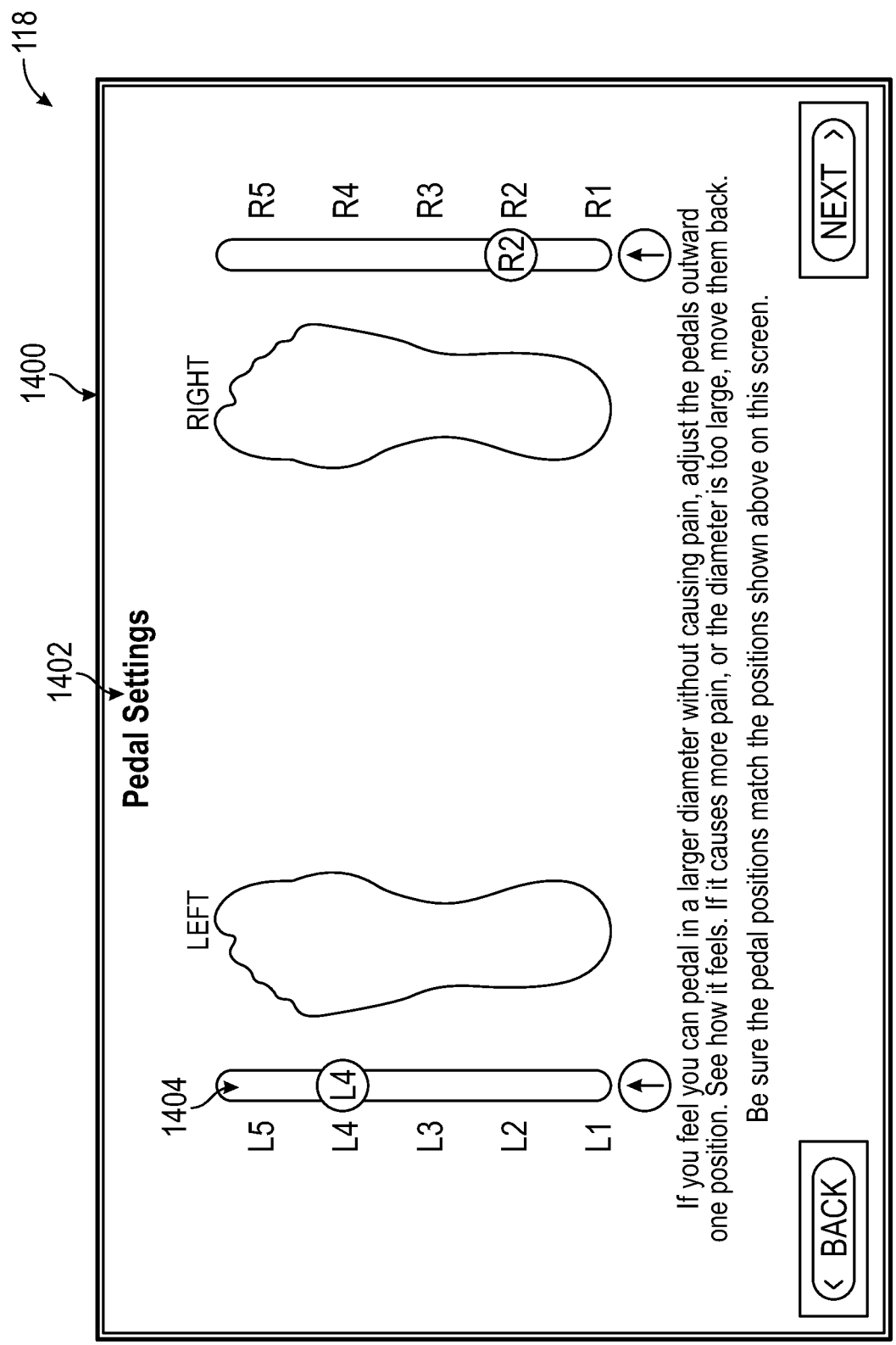
FIG. 14 generally illustrates an example user interface of the user portal, the user interface presenting pedal settings for a user according to principles of the present disclosure.

FIG. 14 generally illustrates an example user interface 1400 of the user portal 118, the user interface 1400 presenting pedal settings 1402 for a user according to principles of the present disclosure. As depicted graphical representation of feet are presented on the user interface 1400 and two sliders including positions corresponding to portions of the feet. For example, a left slider includes positions L1, L2, L3, L4, and L5. A right slider includes positions R1, R2, R3, R4, and R5. A button 1404 may be slid up or down on the sliders to automatically adjust the pedal position on the radially-adjustable coupling via the pedal arm assembly. The pedal positions may be automatically populated according to the treatment plan but the user has the option to modify them based on comfort level. The changed positions may be stored locally on the computing device 102, sent to the computing device 114 executing the clinical portal 126, and/or sent to the cloud-based computing system 116.

Figure 15:
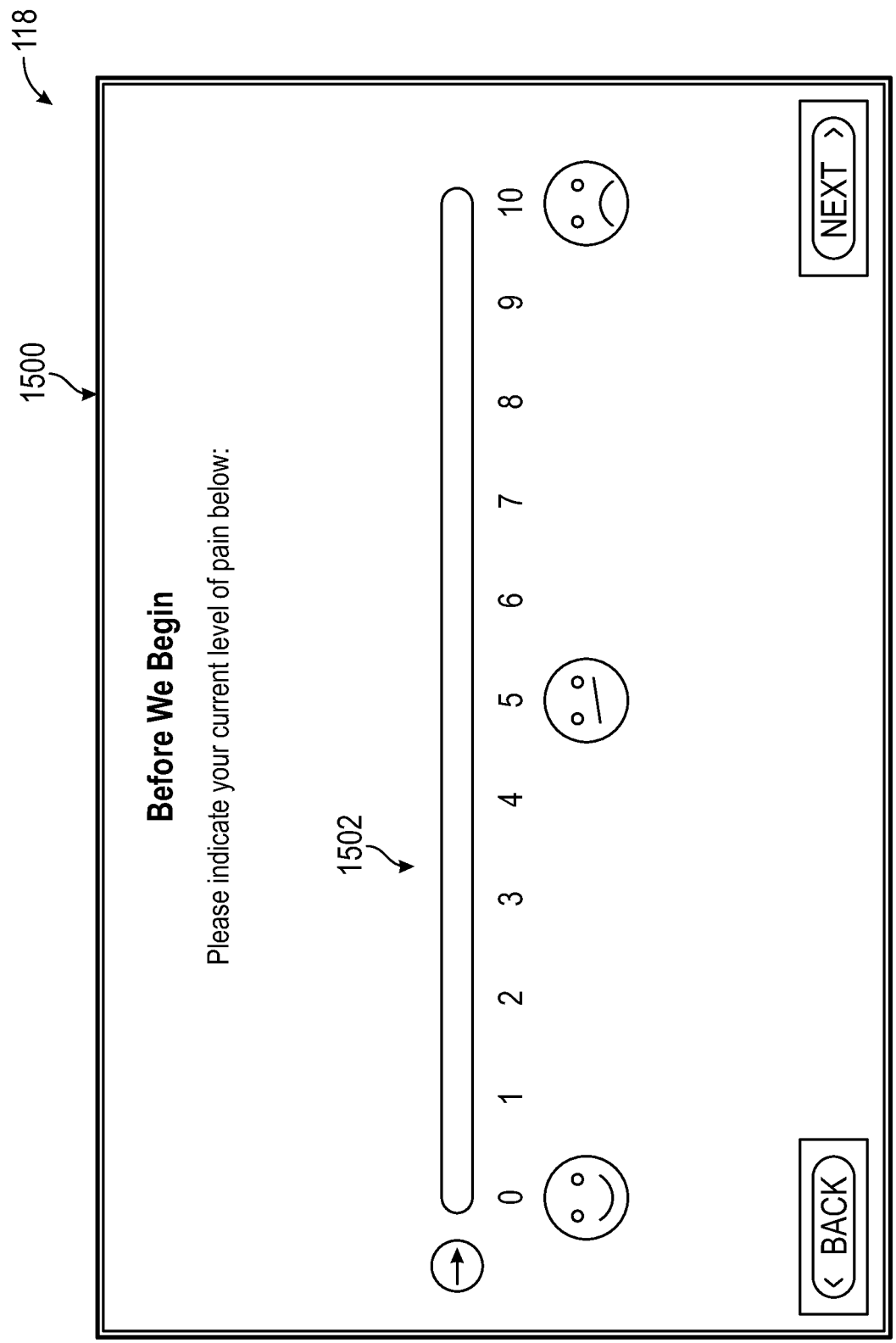
FIG. 15 generally illustrates an example user interface of the user portal, the user interface presenting a scale for measuring pain of the user at a beginning of a pedaling session according to principles of the present disclosure.

FIG. 15 generally illustrates an example user interface 1500 of the user portal 118, the user interface 1500 presenting a scale 1502 for measuring discomfort of the user at a beginning of a pedaling session according to principles of the present disclosure. The scale 1502 may provide options ranging for no discomfort (e.g., smiley face), mild discomfort, to high discomfort. This discomfort information may be stored locally on the computing device 102, sent to the computing device 114 executing the clinical portal 126, and/or sent to the cloud-based computing system 116.

Figure 16:
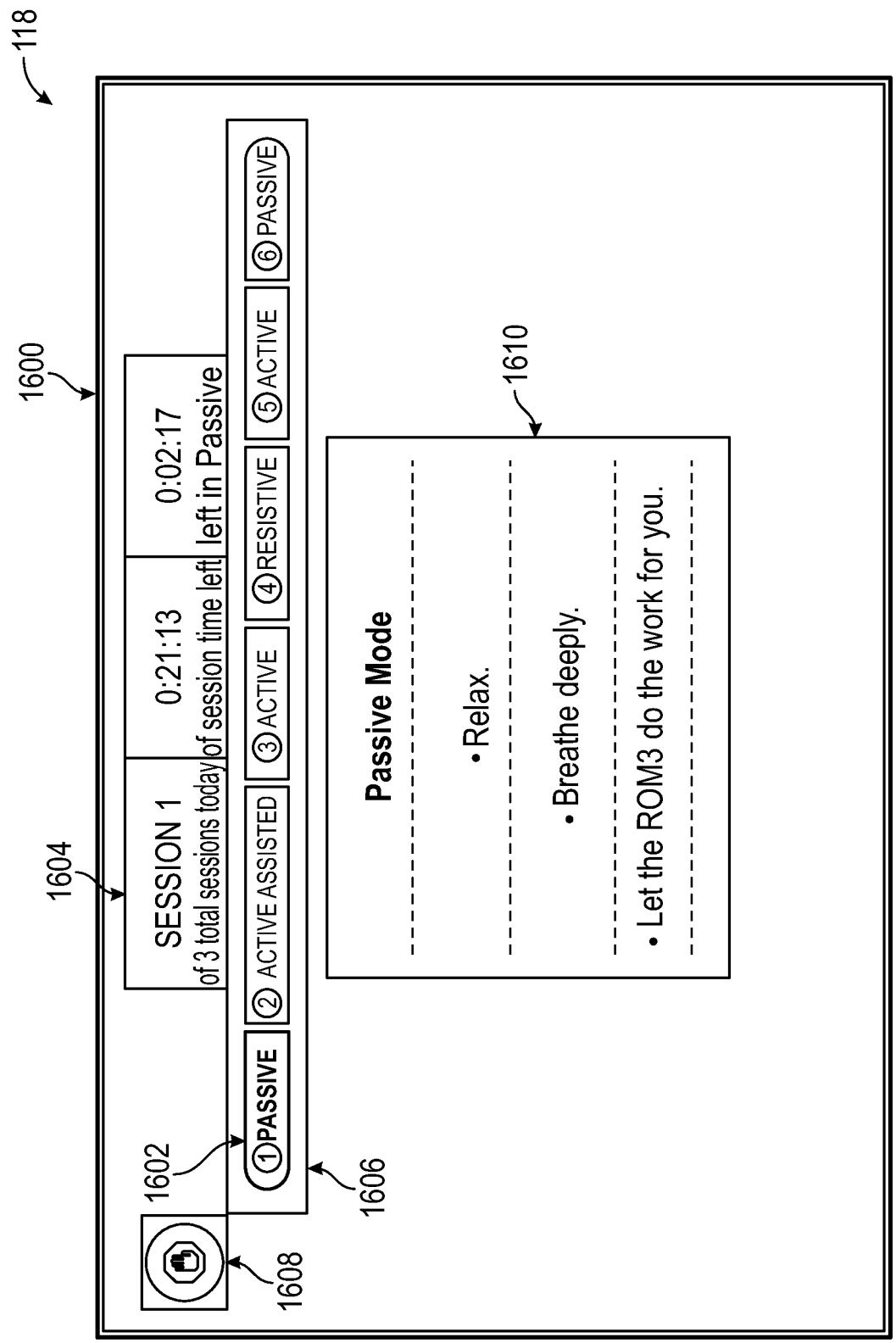
FIG. 16 generally illustrates an example user interface of the user portal, the user interface presenting that the electromechanical device is operating in a passive mode according to principles of the present disclosure.

FIG. 16 generally illustrates an example user interface 1600 of the user portal 118, the user interface 118 presenting that the electromechanical device 104 is operating in a passive mode 1602 according to principles of the present disclosure. The user interface 1600 presents which pedaling session 1604 (session 1) is being performed and how many other pedaling sessions are scheduled for the day. The user interface 1600 also presents an amount of time left in the pedaling session 1604 and an amount of time left in the current mode (passive mode). The full lineup of modes in the pedaling session 1604 are displayed in box 1606. While in the passive mode, the computing device 102 controls the electric motor 122 to independently drive the radially-adjustable couplings so the user does not have to exert any force on the pedals but their affected body part and/or muscles are stretched and warmed up. At any time, if the user so desires, the user may select a stop button 1608, which causes the electric motor 122 to lock and stop the rotation of the radially-adjustable couplings 124 instantaneously or over a set period of time. A descriptive box 1610 may provide instructions related to the current mode to the user.

FIGS. 17A-17D generally illustrate an example user interface 1700 of the user portal 118, the user interface 1700 presenting that the electromechanical device 104 is operating in active-assisted mode 1702 and the user is applying various amounts of force to the pedals 110 according to principles of the present disclosure. Graphical representations 1702 of feet are presented on the user interface 1700 and the graphical representations may fill up based on the amount of force measured at the pedals 110. The force sensors (e.g., strain gauge) in the pedal 110 may measure the forces exerted by the user and the microcontroller of the pedal 110 may transmit the force measurements to the computing device 102. Notifications may be presented when the amount of force is outside of a threshold target force (e.g., either below a range of threshold target force or above the range of threshold target force). For example, in FIG. 17A, the right foot includes a notification to apply more force with the right foot because the current force measured at the pedal 110 is below the threshold target force.

A virtual tachometer 1706 is also presented that measures the revolutions per minute of the radially-adjustable couplings 124 and displays the current speed that the user is pedaling. The tachometer 1706 includes areas 1708 (between 0 and 10 revolutions per minute and between 20 and 30 revolutions per minute) that the user should avoid according to their treatment plan. In the depicted example, the treatment plan specifies the user should keep the speed between 10 and 20 revolutions per minute. The electromechanical device 104 transmits the speed to the computing device 102 and the needle 1710 moves in real-time as the user operates the pedals 110. Notifications are presented near the tachometer 1706 that may indicate that the user should keep the speed above a certain threshold revolutions per minute (e.g., 10 RPM). If the computing device 102 receives a speed from the device 104 and the speed is below the threshold revolutions per minute, the computing device 102 may control the electric motor 122 to drive the radially-adjustable couplings 124 to maintain the threshold revolutions per minute.

Figure 17A:
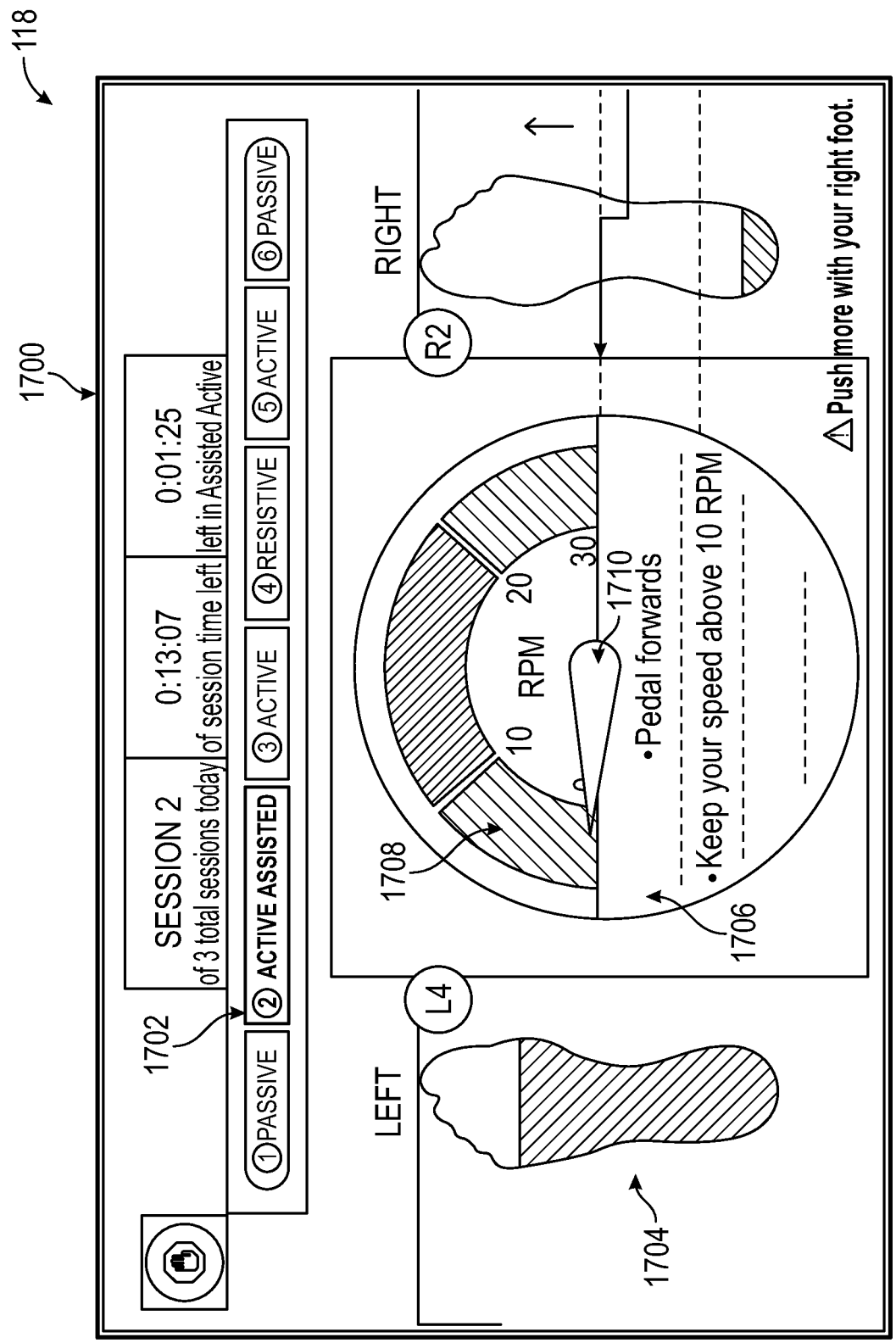
FIGS. 17A-17D generally illustrate an example user interface of the user portal, the user interface presenting that the electromechanical device is operating in active-assisted mode and the user is applying various amounts of force to the pedals according to principles of the present disclosure.
Figure 17B:
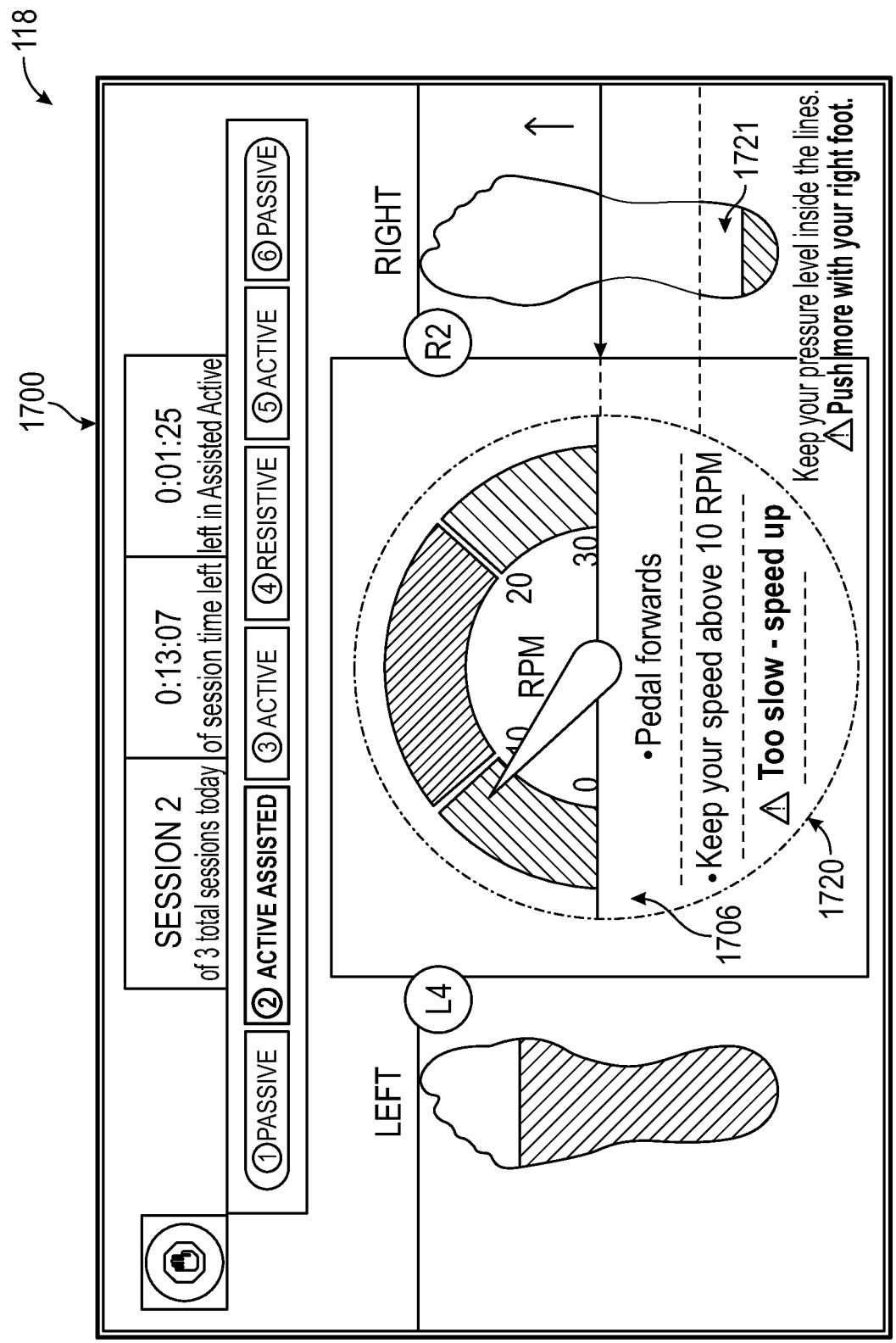
Figure 17C:
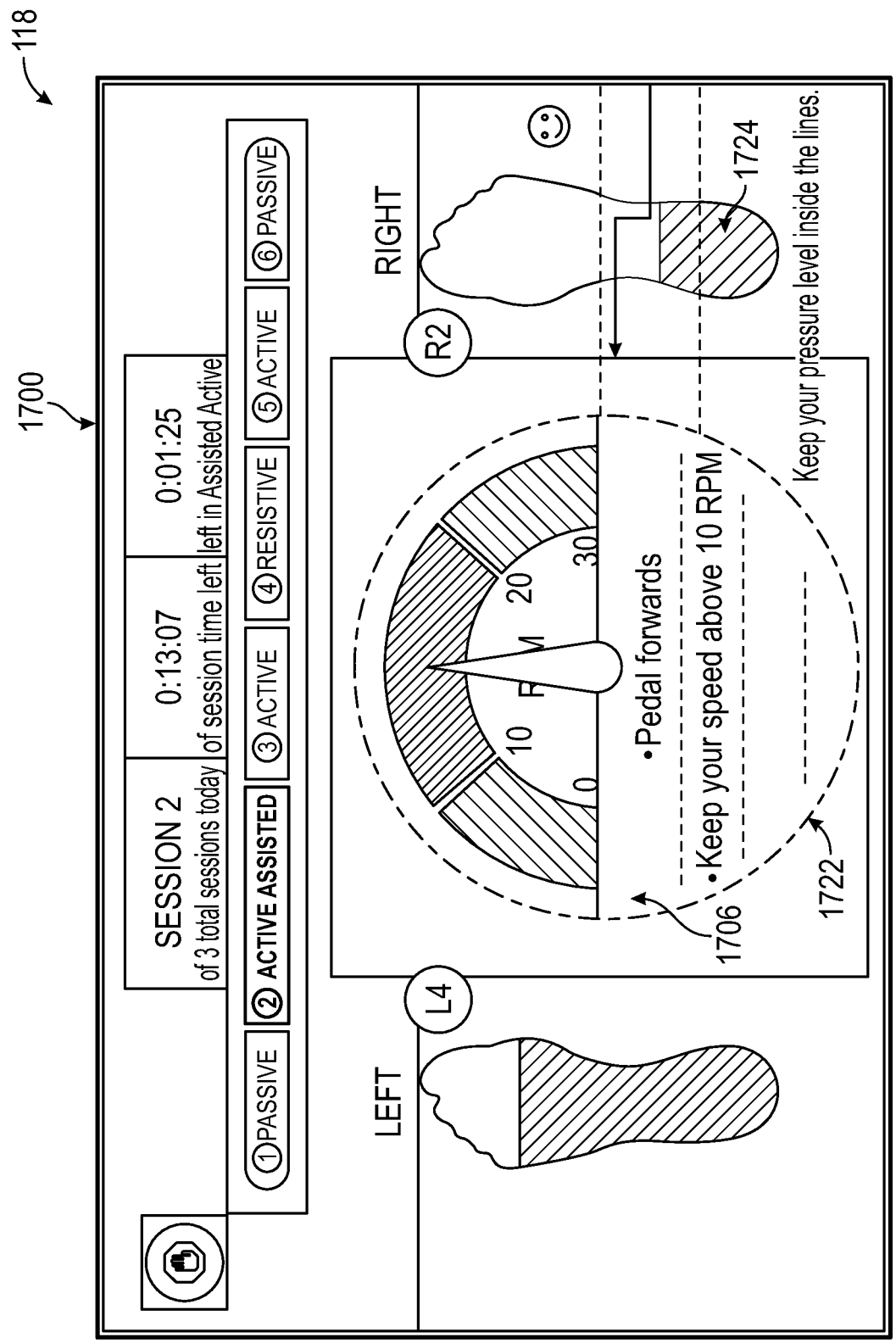
Figure 17D:
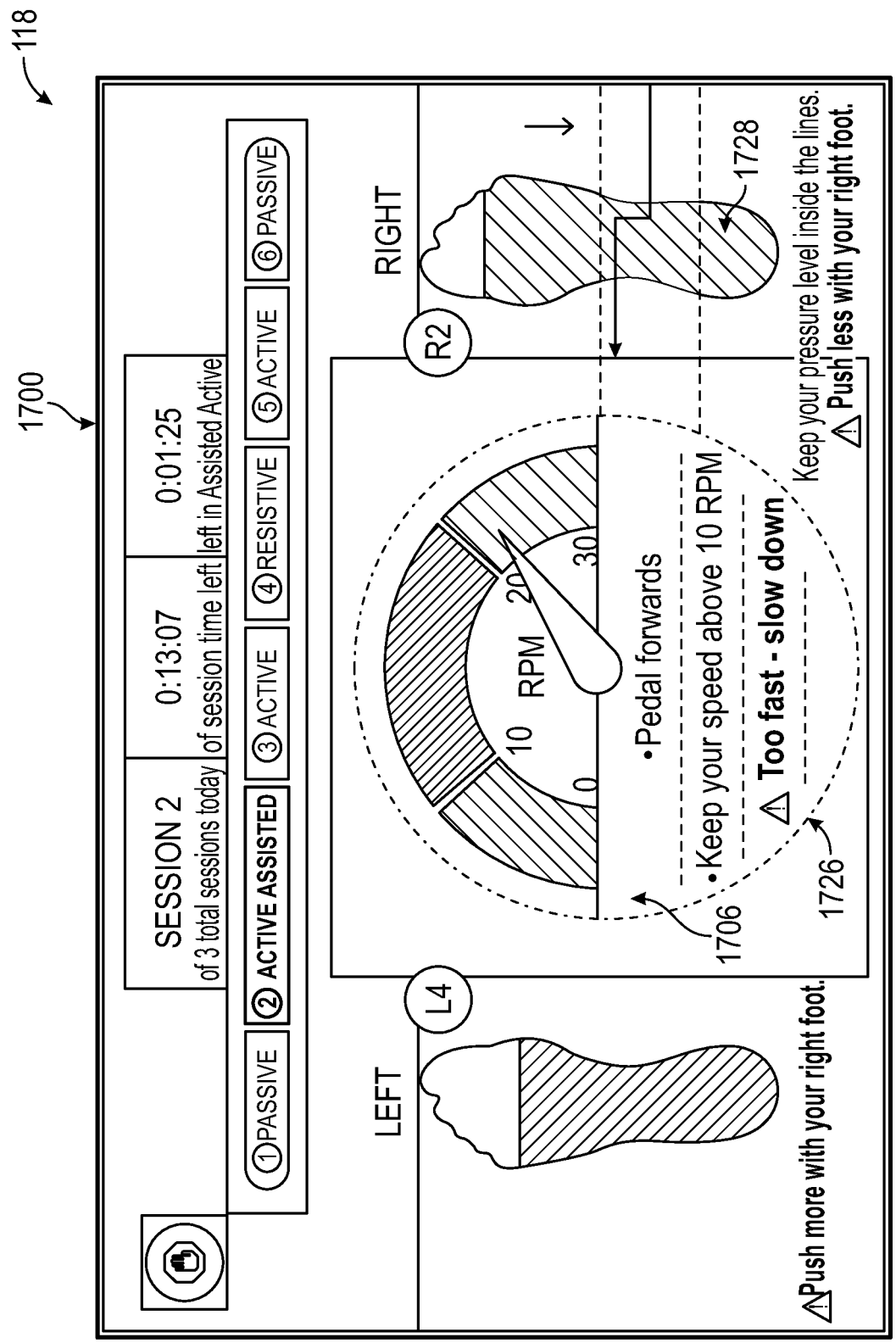

FIG. 17B depicts the example user interface 1700 presenting a graphic 1720 for the tachometer 1706 when the speed is below the threshold revolutions per minute. As depicted, a notification is presented that says "Too slow— speed up". Also, the user interface 1700 presents an example graphical representation 1721 of the right foot when the pressure exerted at the pedal is below the range of threshold target force. A notification may be presented that reads "Push more with your right foot." FIG. 17C depicts the example user interface 1700 presenting a graphic 1722 for the tachometer 1706 when the speed is within the desired target revolutions per minute. Also, the user interface 1700 presents an example graphical representation 1724 of the right foot when the pressure exerted at the pedal is within the range of threshold target force. FIG. 17D depicts the example user interface 1700 presenting a graphic 1726 for the tachometer 1706 when the speed is above the desired target revolutions per minute. As depicted, a notification is presented that reads "Too fast—slow down". Also, the user interface 1700 presents an example graphical representation 1728 of the right foot when the pressure exerted at the pedal is above the range of threshold target force. A notification may be presented that reads "Push less with your right foot."

Figure 18:
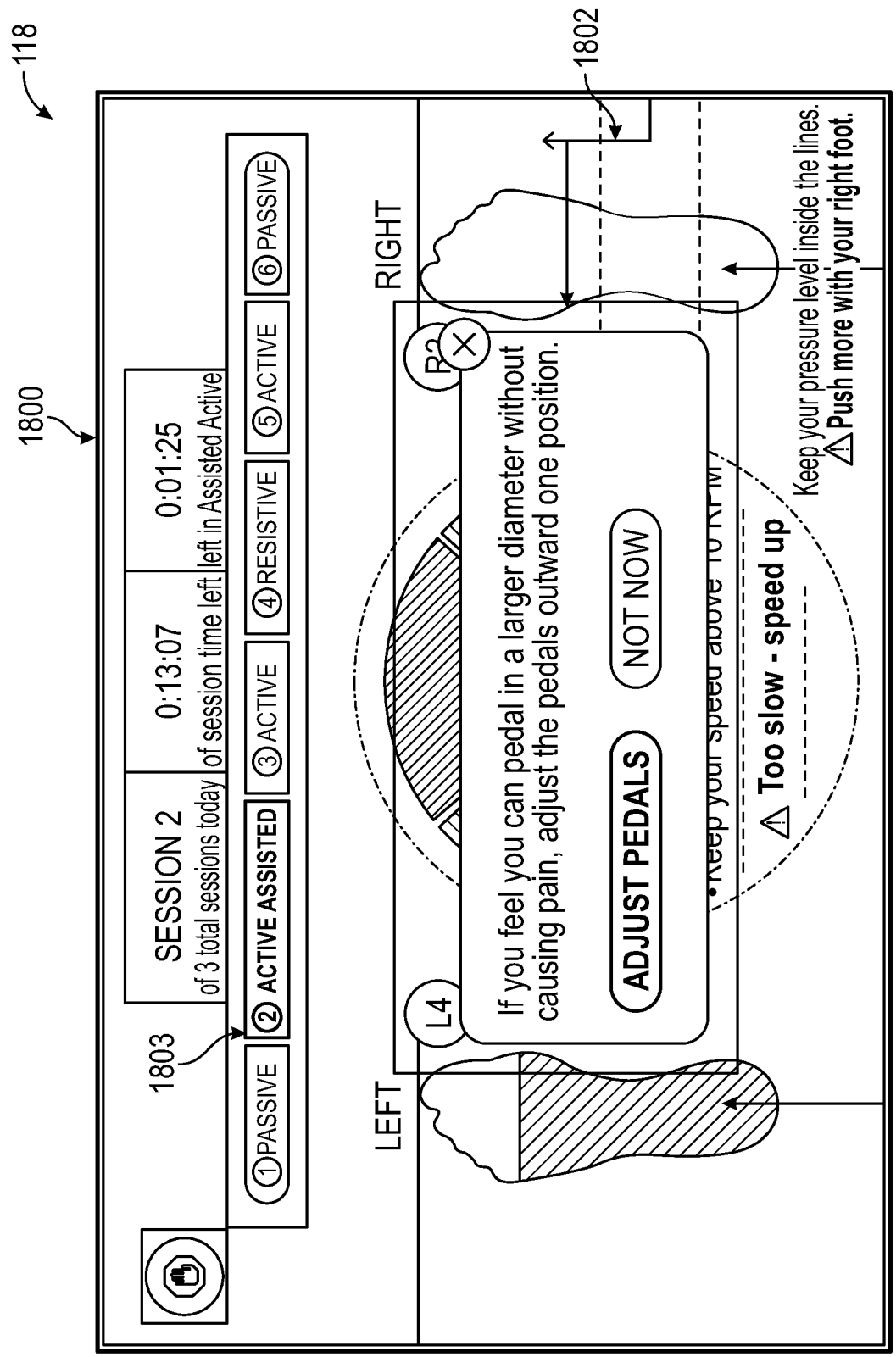
FIG. 18 generally illustrates an example user interface of the user portal, the user interface presenting a request to modify pedal position while the electromechanical device is operating in active-assisted mode according to principles of the present disclosure.

FIG. 18 generally illustrates an example user interface 1800 of the user portal 118, the user interface 1800 presenting a request 1802 to modify pedal position while the electromechanical device 104 is operating in active-assisted mode according to principles of the present disclosure. The request 1802 may pop up on a regular interval as specified in the treatment plan. If the user selects the "Adjust Pedals" button, the user portal 118 may present a screen that allows the user to modify the position of the pedals 110.

Figure 19:
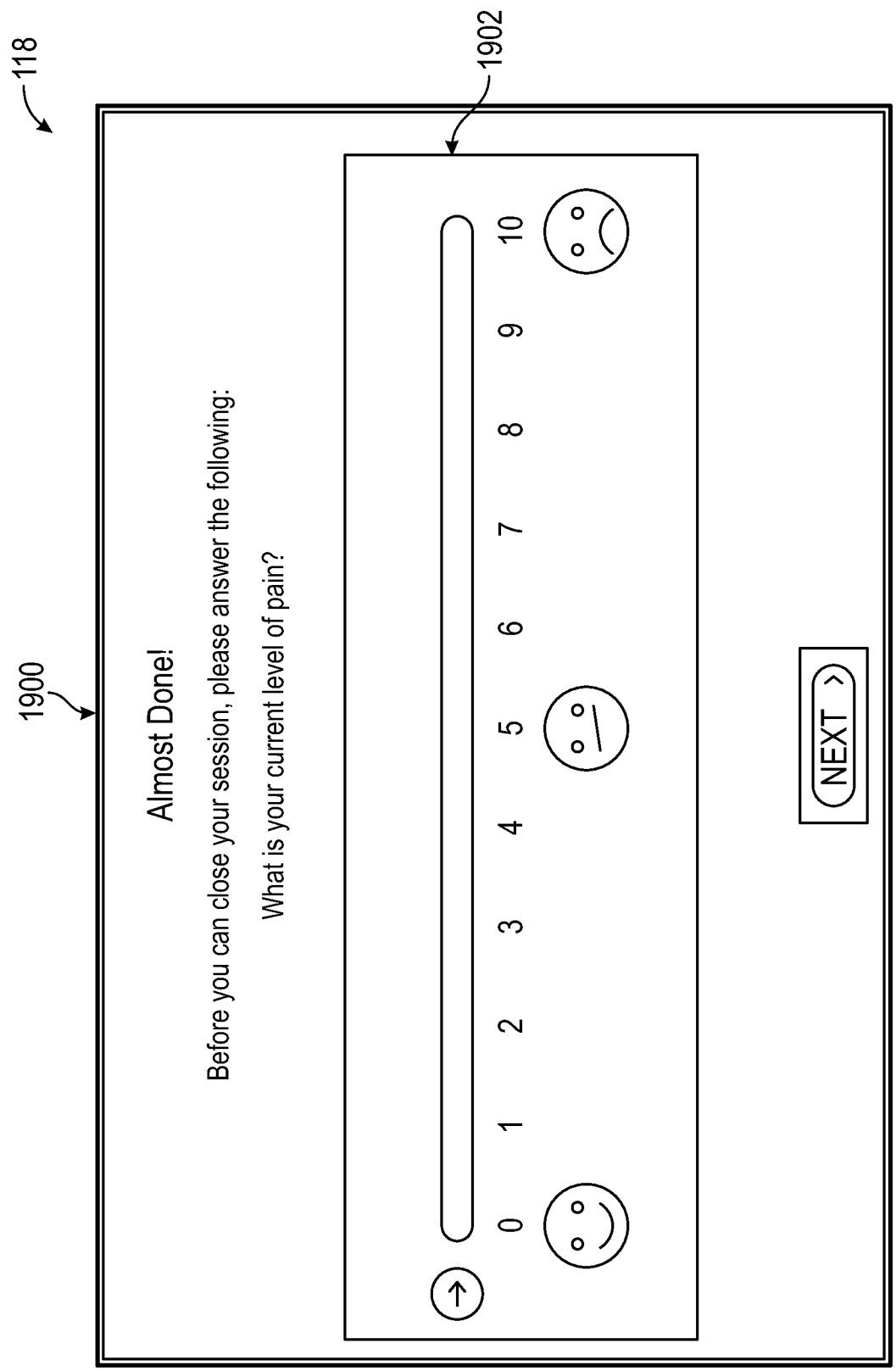
FIG. 19 generally illustrates an example user interface of the user portal, the user interface presenting a scale for measuring pain of the user at an end of a pedaling session according to principles of the present disclosure.

FIG. 19 generally illustrates an example user interface 1900 of the user portal 118, the user interface 1900 presenting a scale 1902 for measuring discomfort of the user at an end of a pedaling session according to principles of the present disclosure. The scale 1902 may provide options ranging for no discomfort (e.g., smiley face), mild discomfort, to high discomfort. This discomfort information may be stored locally on the computing device 102, sent to the computing device 114 executing the clinical portal 126, and/or sent to the cloud-based computing system 116.

Figure 20:
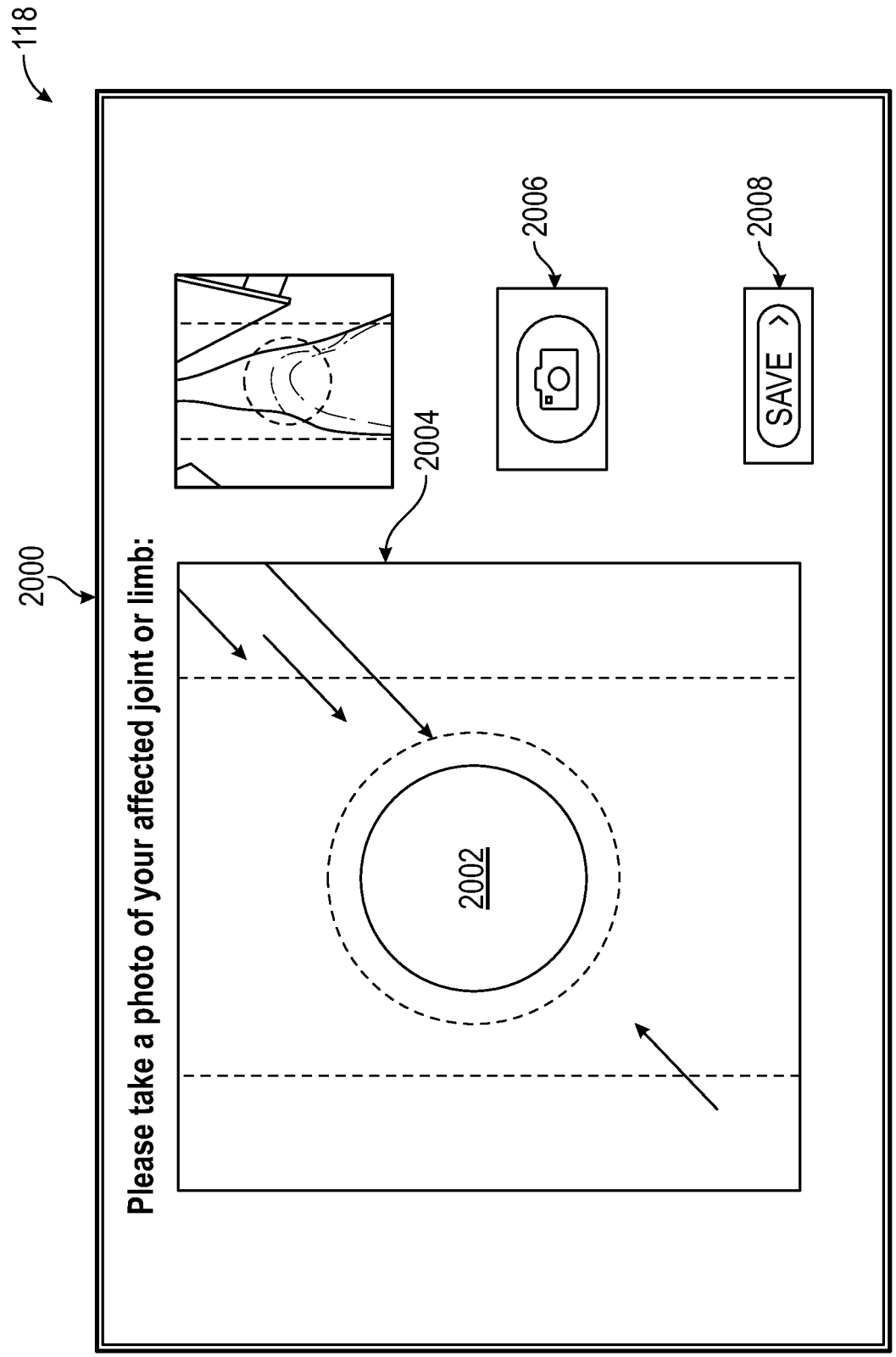
FIG. 20 generally illustrates an example user interface of the user portal, the user interface enabling the user to capture an image of the body part under prehabilitation according to principles of the present disclosure.

FIG. 20 generally illustrates an example user interface 2000 of the user portal 118, the user interface 2000 enabling the user to capture an image of the body part under prehabilitation according to principles of the present disclosure. For example, an image capture zone 2002 is presented on the user interface 2000 and the dotted lines 2004 will populate to show a rough outline of the leg, for example, with a circle to indicate where their kneecap (patella) should be in the image. This enables the patient to line up their leg/knee for the image. The user may select a camera icon 2006 to capture the image. If the user is satisfied with the image, the user can select a save button 2008 to store the image on the computing device 102 and/or in the cloud-based computing system 116. Also, the image may be transmitted to the computing device 114 executing the clinical portal 126.

Figure 21A:
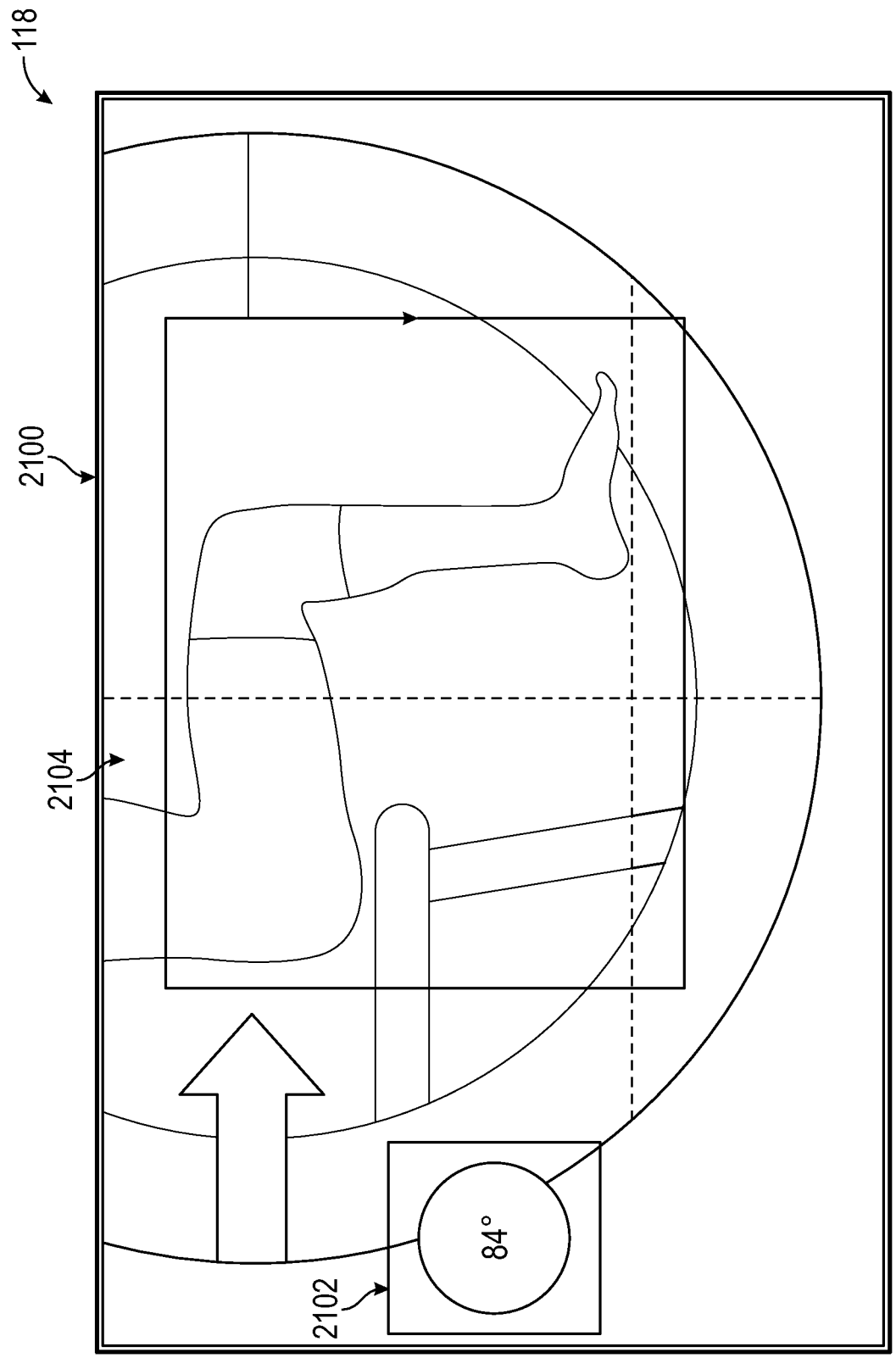
FIGS. 21A-21D generally illustrate an example user interface of the user portal, the user interface presenting angles of extension and bend of a lower leg relative to an upper leg according to principles of the present disclosure.

FIGS. 21A-D generally illustrate an example user interface 2100 of the user portal 118, the user interface 2100 presenting angles 2102 of extension and bend of a lower leg relative to an upper leg according to principles of the present disclosure. As depicted in FIG. 21A, the user interface 2100 presents a graphical animation 2104 of the user's leg extending in real-time. The knee angle in the graphical animation 2104 may match the angle 2102 presented on the user interface 2100. The computing device 102 may receive the angles 210 of extension from the goniometer 106 that is worn by the user during an extension session and/or a pedaling session. To that end, although the graphical animation 2104 depicts the user extending their leg during an extension session, it should be understood that the user portal 118 may be configured to display the angles 2102 in real-time as the user operates the pedals 110 of the electromechanical device 104 in real-time.

Figure 21B:
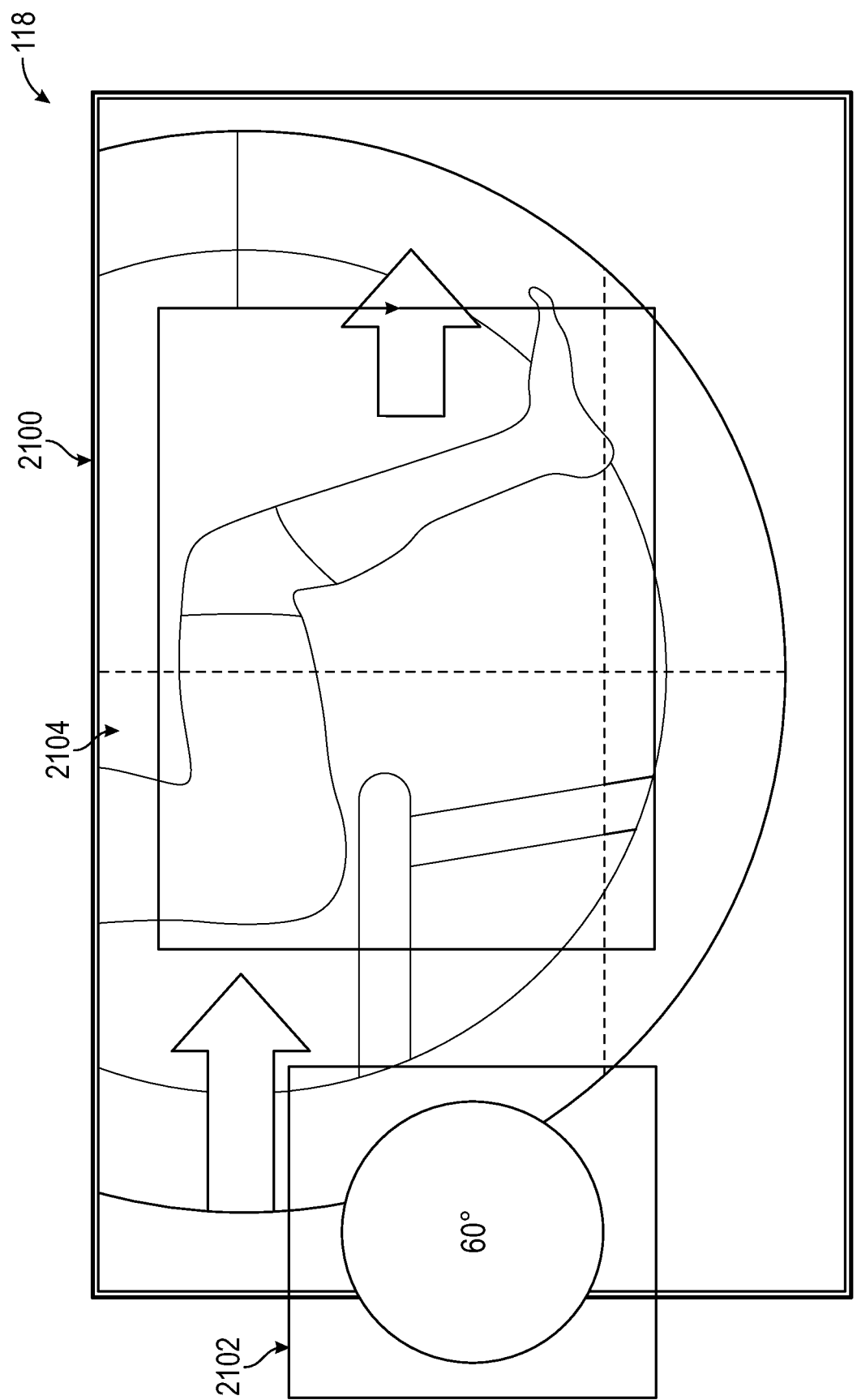
Figure 21C:
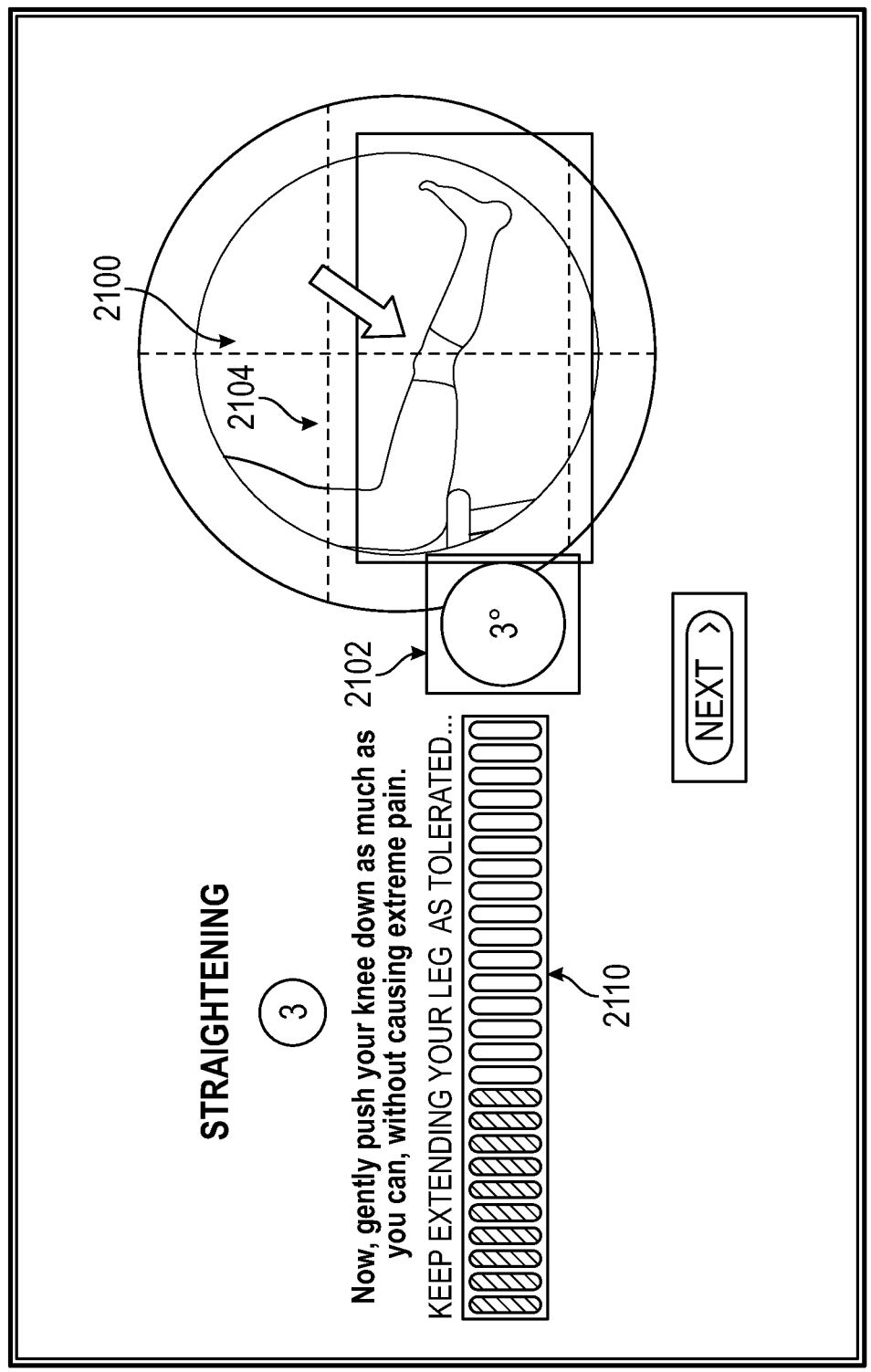
Figure 21D:
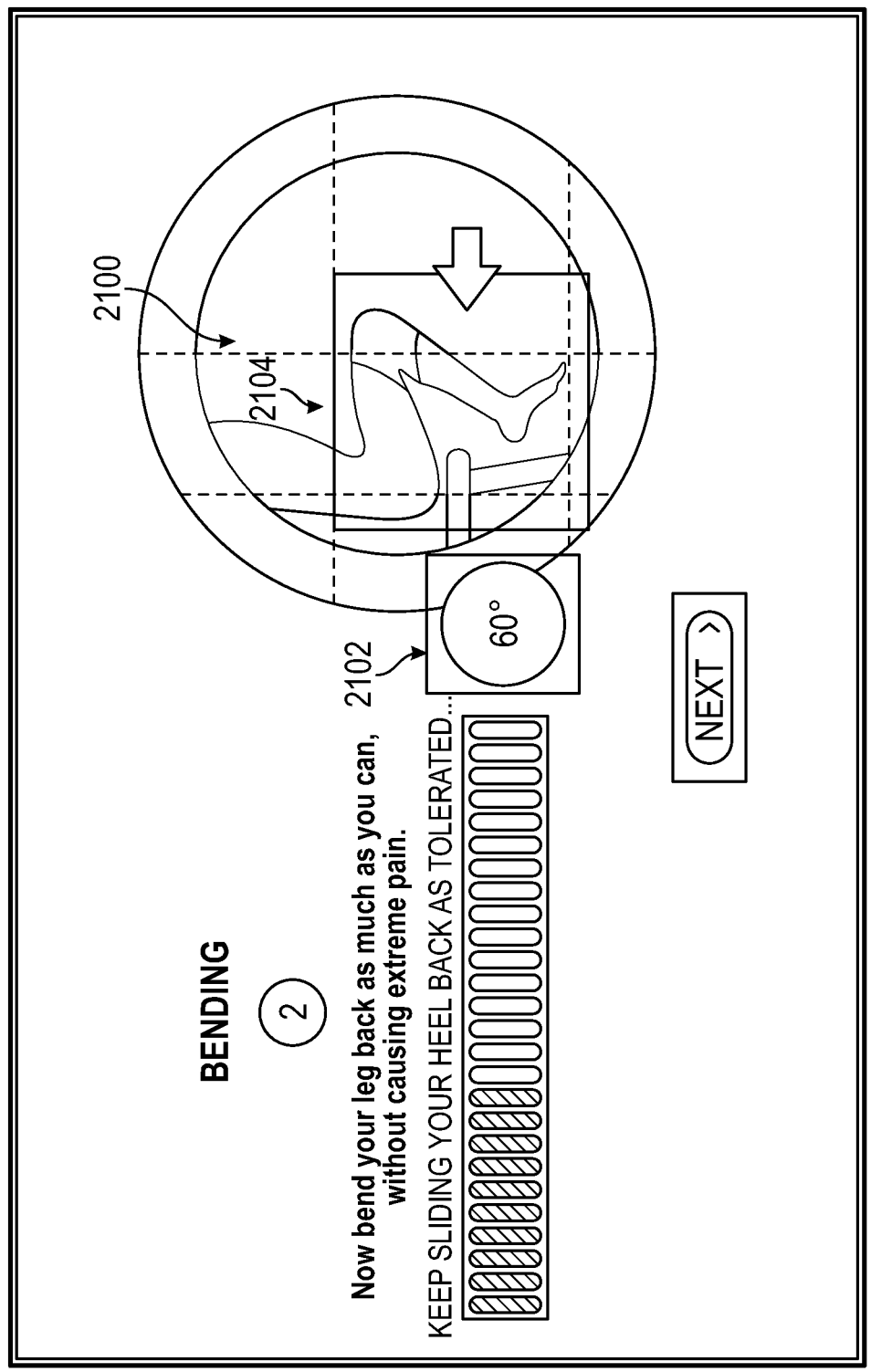

FIG. 21B illustrates the user interface 2100 with the graphical animation 2104 as the lower leg is extended farther away from the upper leg, and the angle 2102 changed from 84 degrees to 60 degrees of extension. FIG. 21C illustrates the user interface 2100 with the graphical animation 2104 as the lower leg is extended even farther away from the upper leg. The computing device 102 may record the lowest angle that the user is able to extend their leg as measured by the goniometer 106. That angle 2102 may be sent to the computing device 114 and that lowest angle may be presented on the clinical portal 126 as an extension statistic for that extension session. Further, a bar 2110 is presented and the bar may fill from left to right over a set amount of time. A notification may indicate that the patient should push down on their knee over the set amount of time. The user interface 2100 in FIG. 21D is similar to FIG. 21C but it presents the angle 2102 of bend, measured by the goniometer 106, as the user retracts their lower leg closer to their upper leg. As depicted, the graphical animation 2104 depicts the angle of the knee matching the angle 2102 presented on the user interface 2100 in real-time. The computing device 102 may record the highest angle that the user is able to bend their leg as measured by the goniometer 106. That angle 2102 may be sent to the computing device 114 and that highest angle may be presented on the clinical portal 126 as a bend statistic for that bend session.

Figure 22:
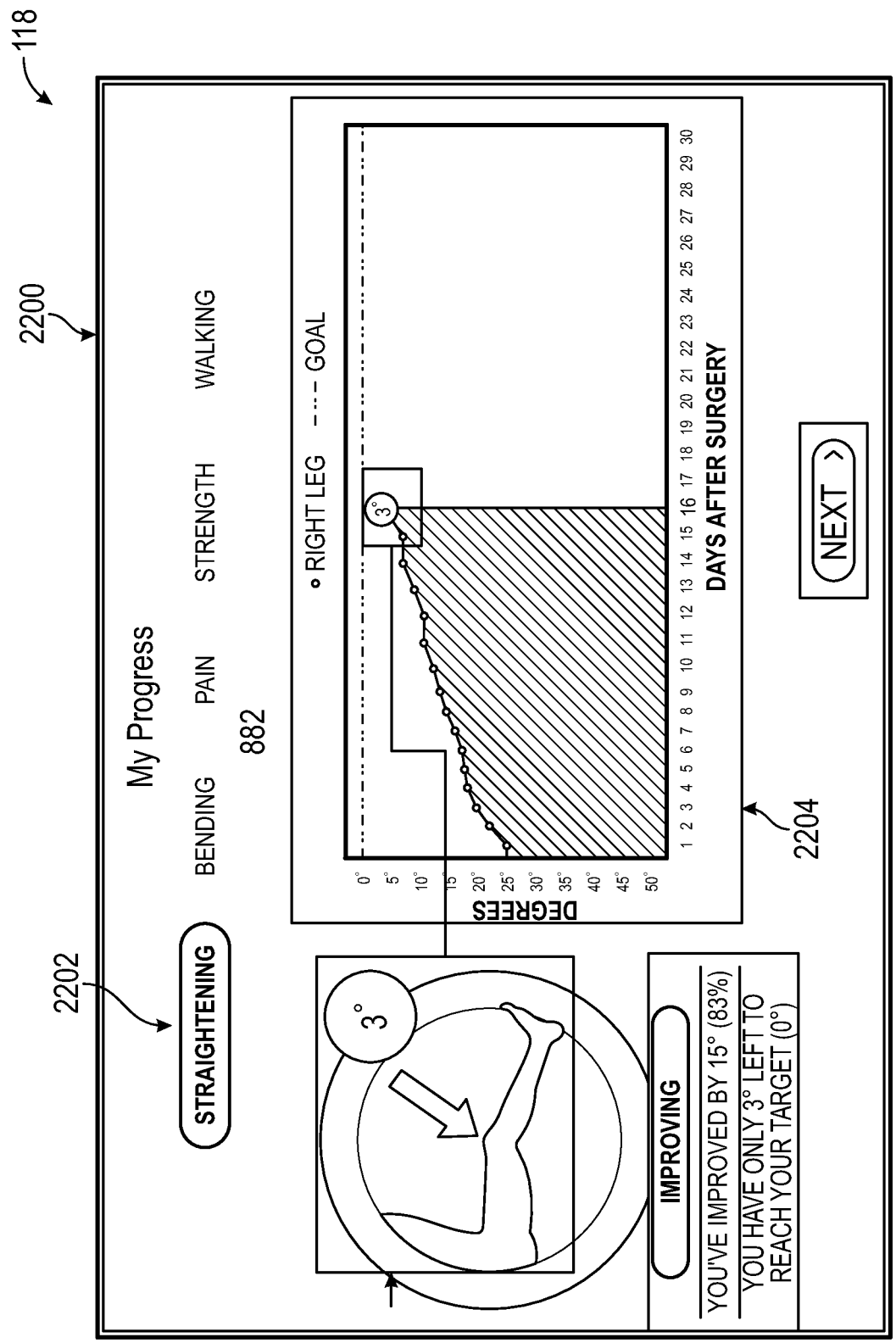
FIG. 22 generally illustrates an example user interface of the user portal, the user interface presenting a progress screen for a user extending the lower leg away from the upper leg according to principles of the present disclosure.

FIG. 22 generally illustrates an example user interface 2200 of the user portal 118, the user interface 2200 presenting a progress report 2202 for a user extending the lower leg away from the upper leg according to principles of the present disclosure. The user interface 2200 presents a graph 2204 with the degrees of extension on a y-axis and the days after surgery on the x-axis. The angles depicted in the graph 2204 are the lowest angles achieved each day. The user interface 2202 also depicts the lowest angle the user has achieved for extension and indicates an amount of improvement (83%) in extension since beginning the treatment plan. The user interface 2200 also indicates how many degrees are left before reaching a target extension angle.

Figure 23:
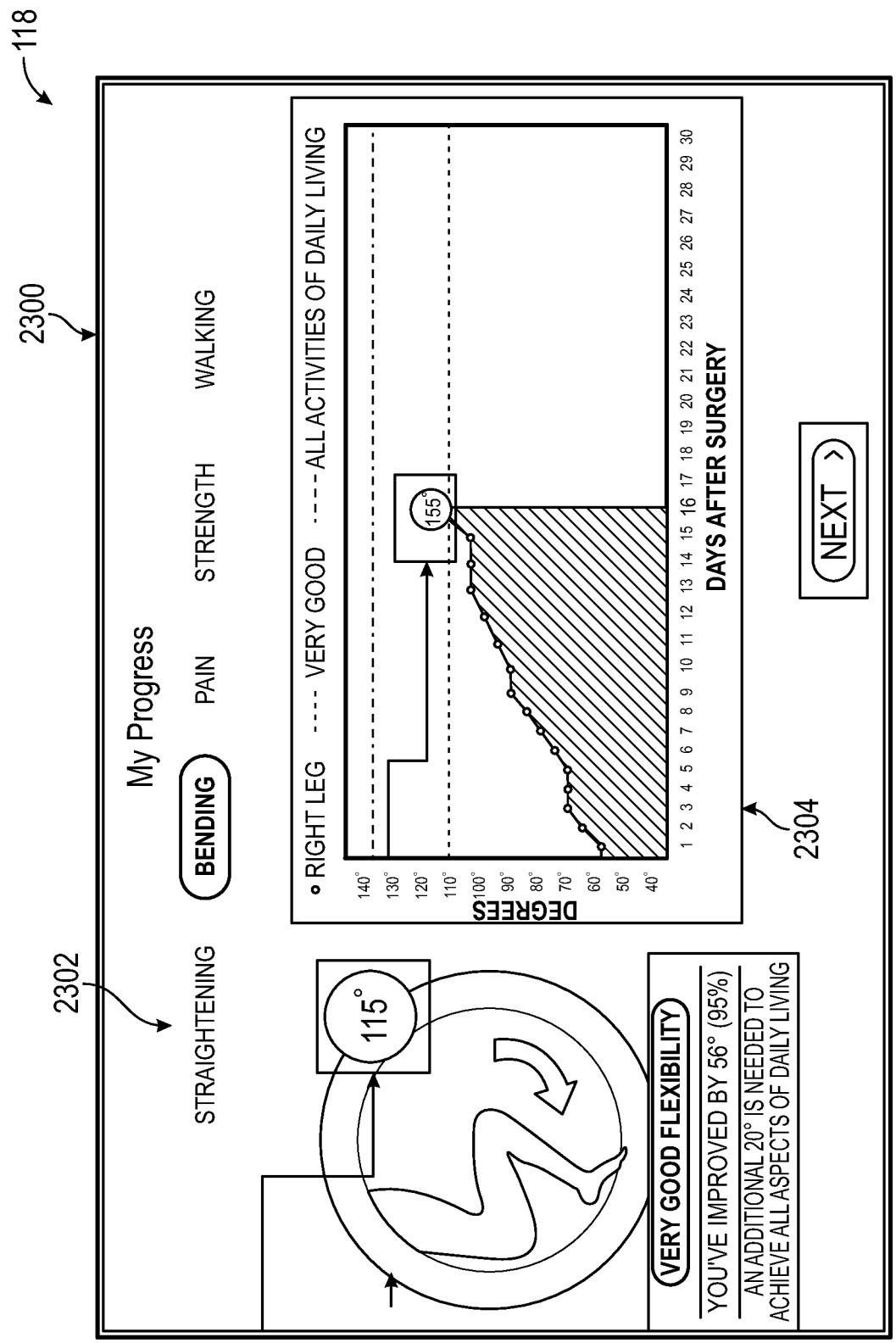
FIG. 23 generally illustrates an example user interface of the user portal, the user interface presenting a progress screen for a user bending the lower leg toward the upper leg according to principles of the present disclosure.

FIG. 23 generally illustrates an example user interface 2300 of the user portal 118, the user interface 2300 presenting a progress screen 2302 for a user bending the lower leg toward the upper leg according to principles of the present disclosure. The user interface 2300 presents a graph 2304 with the degrees of bend on a y-axis and the days after surgery on the x-axis. The angles depicted in the graph 2304 are the highest angles of bend achieved each day. The user interface 2202 also depicts the lowest angle the user has achieved for bending and indicates an amount of improvement (95%) in extension since beginning the treatment plan. The user interface 2200 also indicates how many degrees are left before reaching a target bend angle.

Figure 24:
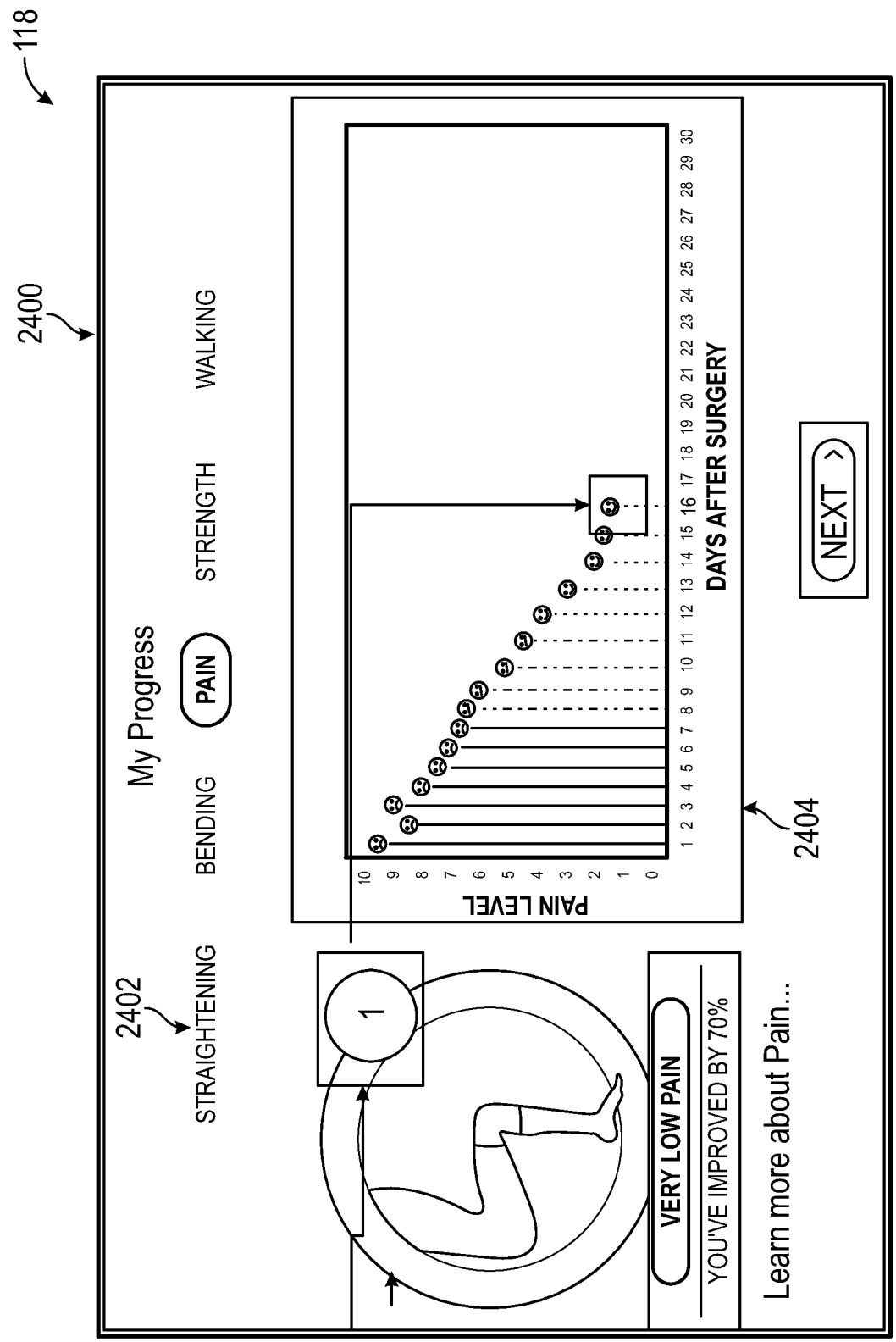
FIG. 24 generally illustrates an example user interface of the user portal, the user interface presenting a progress screen for a pain level of the user according to principles of the present disclosure.

FIG. 24 generally illustrates an example user interface 2400 of the user portal 118, the user interface 2400 presenting a progress screen 2402 for a discomfort level of the user according to principles of the present disclosure. The user interface 2400 presents a graph 2404 with the discomfort level on a y-axis and the days after surgery on the x-axis. The user interface 2400 also depicts the lowest discomfort level the user has reported and a notification indicating the amount of discomfort level the user has improved throughout the treatment plan.

Figure 25:
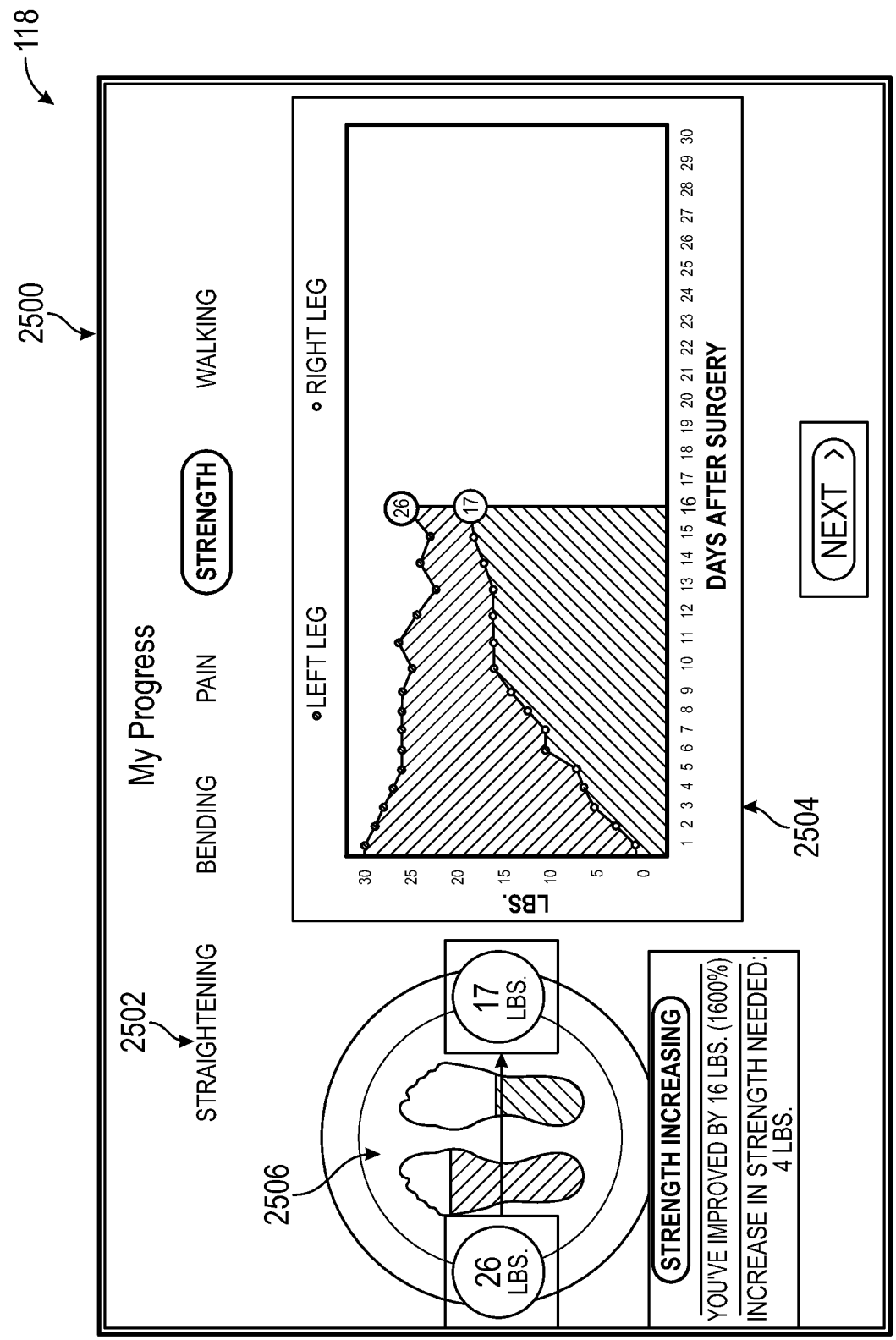
FIG. 25 generally illustrates an example user interface of the user portal, the user interface presenting a progress screen for a strength of a body part according to principles of the present disclosure.

FIG. 25 generally illustrates an example user interface 2500 of the user portal 118, the user interface 118 presenting a progress screen 2502 for a strength of a body part according to principles of the present disclosure. The user interface 2500 presents a graph 2504 with the pounds of force exerted by the patient for both the left leg and the right leg on a y-axis and the days after surgery on the x-axis. The graph 2504 may show an average for left and right leg for a current session. For the number of sessions a user does each day, the average pounds of force for those sessions may be displayed for prior days as well. The user interface 2500 also depicts graphical representations 2506 of the left and right feet and a maximum pound of force the user has exerted for the left and right leg. The maximum pounds of force depicted may be derived from when the electromechanical device 104 is operating in the active mode. The user may select to see statistics for prior days and the average level of active sessions for that day may be presented as well. The user interface 2500 indicates the amount of improvement in strength in the legs and the amount of strength improvement needed to satisfy a target strength goal.

Figure 26:
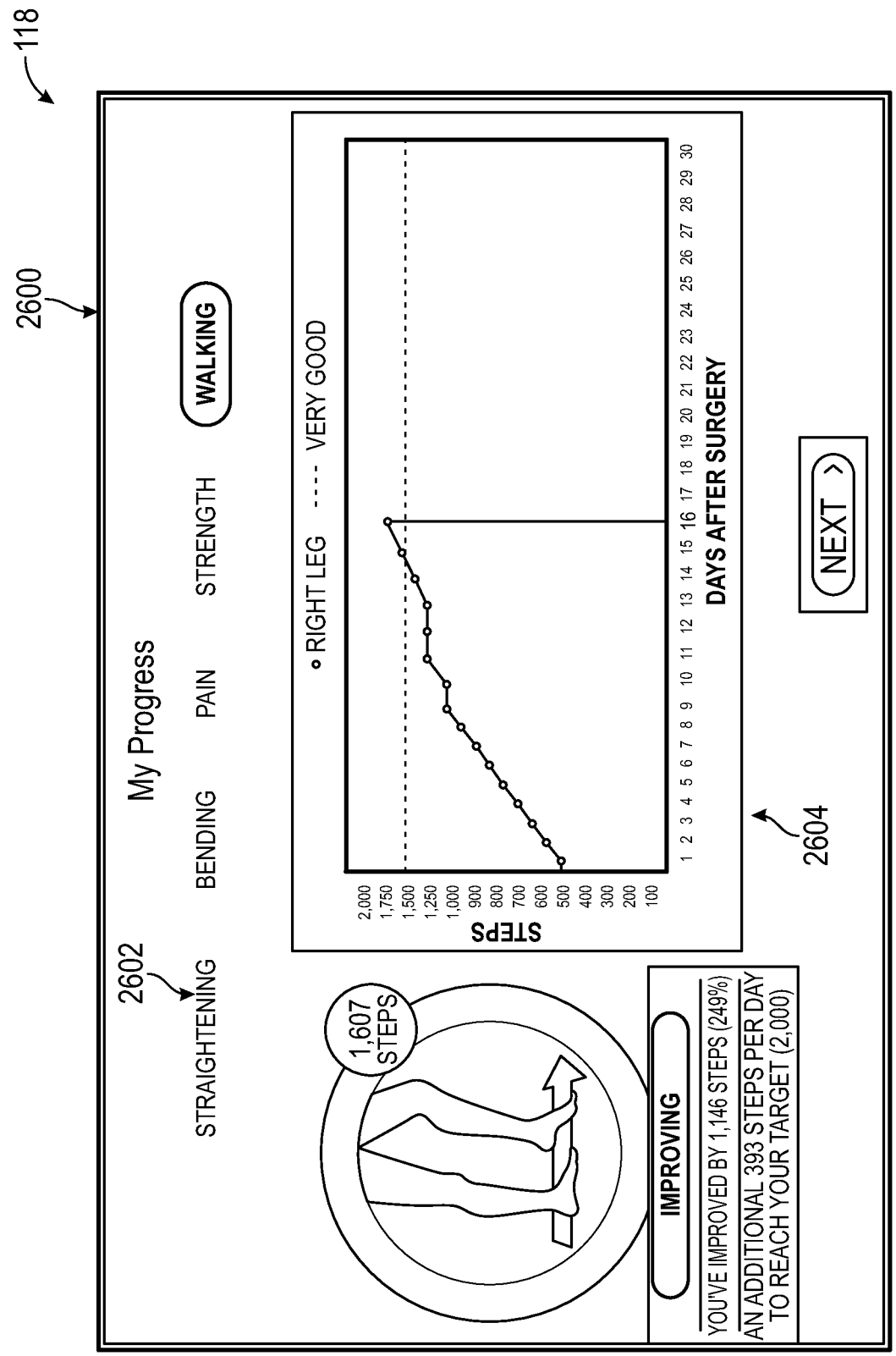
FIG. 26 generally illustrates an example user interface of the user portal, the user interface presenting a progress screen for an amount of steps of the user according to principles of the present disclosure.

FIG. 26 generally illustrates an example user interface 2600 of the user portal 118, the user interface 118 presenting a progress screen 2602 for an amount of steps of the user according to principles of the present disclosure. The user interface 2600 presents a graph 2604 with the number of steps taken by the user on a y-axis and the days after surgery on the x-axis. The user interface 2500 also depicts the highest number of steps the user has taken for amongst all of the days in the treatment plan, the amount the user has improved in steps per day since starting the treatment plan, and the amount of additional steps needed to meet a target step goal. The user may select to view prior days to see their total number of steps they have taken per day.

Figure 27:
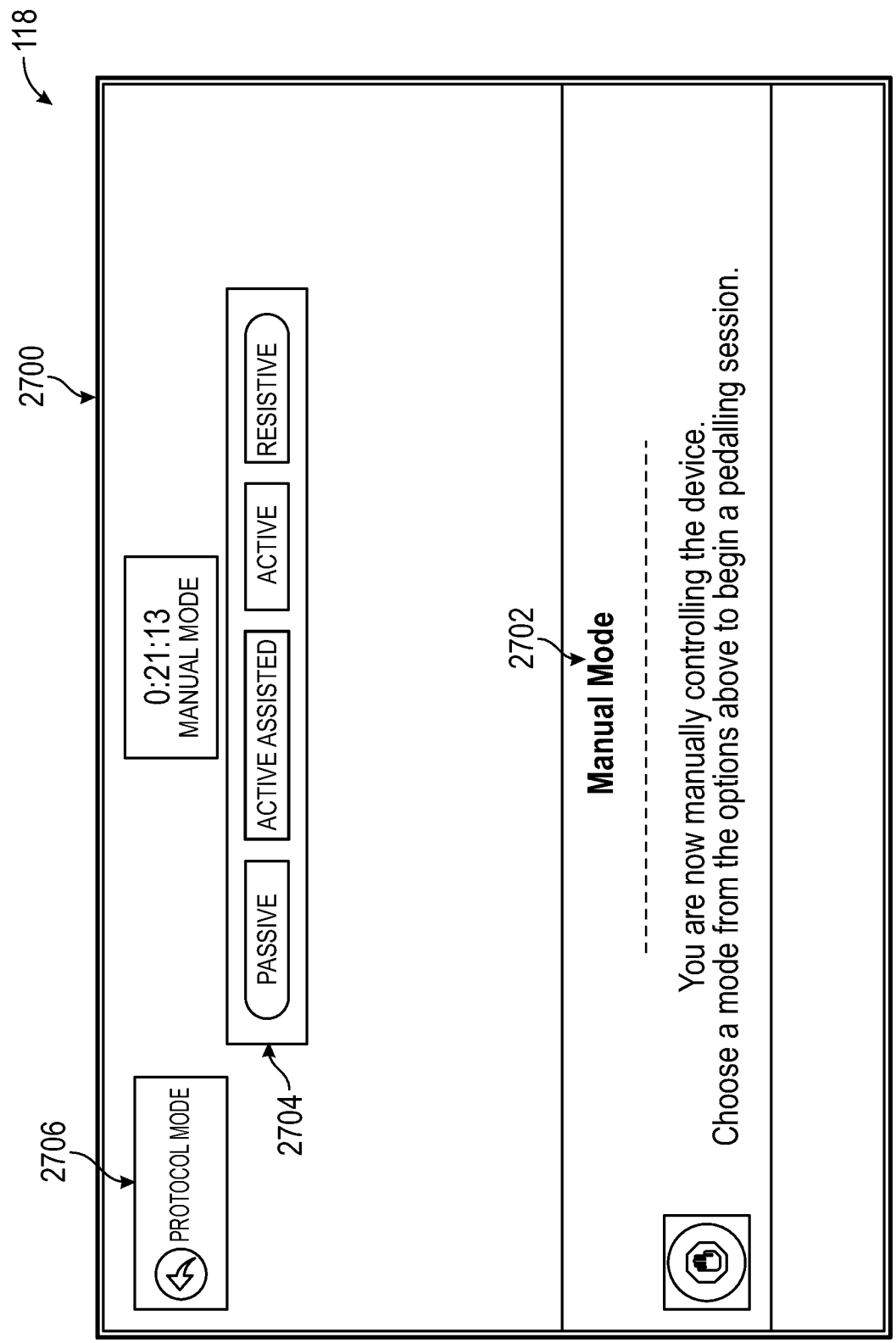
FIG. 27 generally illustrates an example user interface of the user portal, the user interface presenting that the electromechanical device is operating in a manual mode according to principles of the present disclosure.

FIG. 27 generally illustrates an example user interface 2700 of the user portal 118, the user interface 2700 presenting that the electromechanical device 104 is operating in a manual mode 2702 according to principles of the present disclosure. During the manual mode 2702, the user may set the speed, resistance, time to exercise, position of pedals 110, etc. That is, essentially the control system for the electromechanical device 104 may provide no assistance to operation of the electromechanical device 104. When the user selects any of the modes in the box 2704, a pedaling session may begin. Further, when the user selects button 2706, the user portal 118 may return to the user interface 1300 depicted in FIG. 13.

Figure 28:
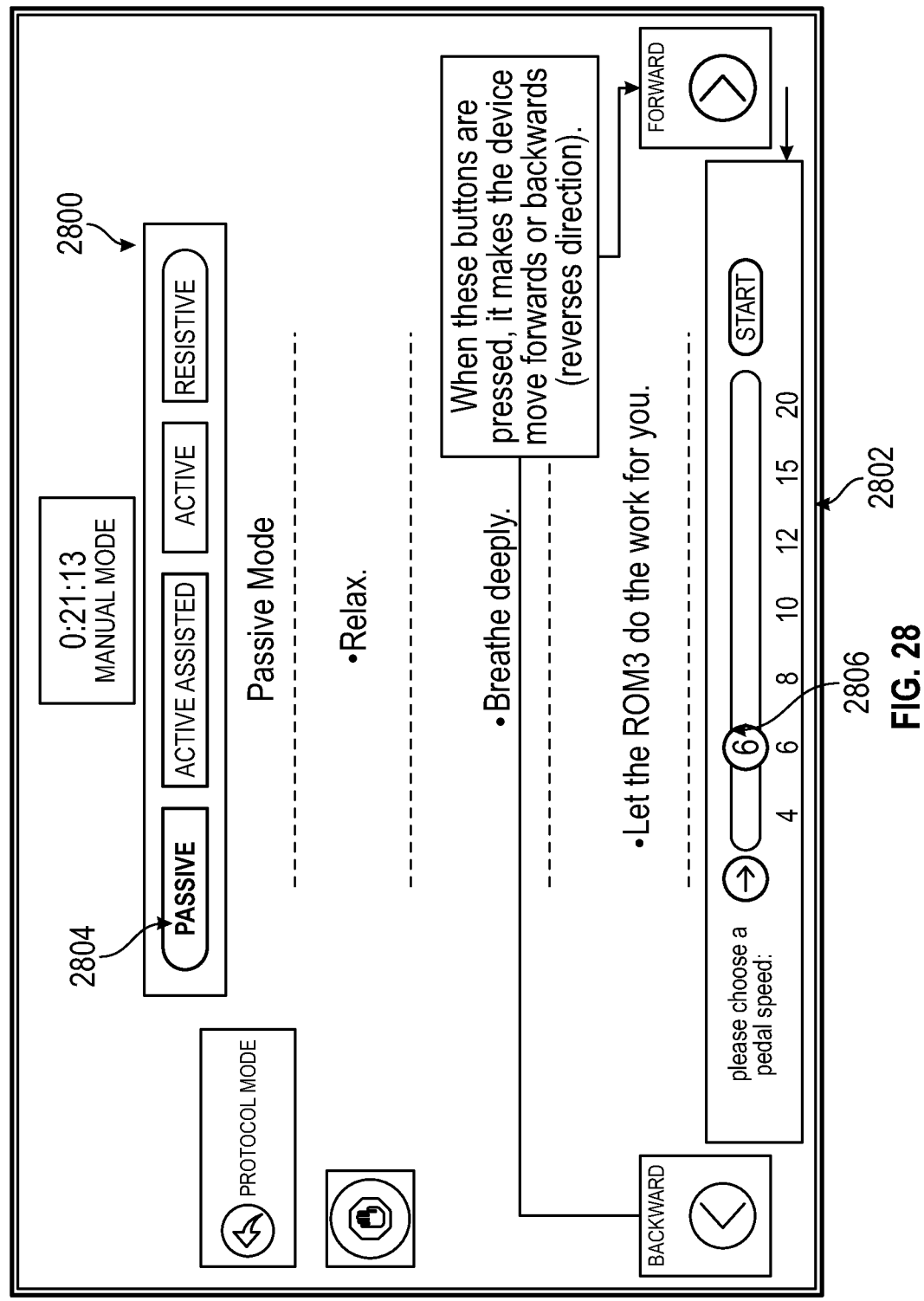
FIG. 28 generally illustrates an example user interface of the user portal, the user interface presenting an option to modify a speed of the electromechanical device operating in the passive mode according to principles of the present disclosure.

FIG. 28 generally illustrates an example user interface 2800 of the user portal 118, the user interface 2800 presenting an option 2802 to modify a speed of the electromechanical device 104 operating in the passive mode 2802 according to principles of the present disclosure. The user may slide button 2806 to adjust the speed as desired during the passive mode where the electric motor 122 is providing the driving force of the radially-adjustable couplings 124.

Figure 29:
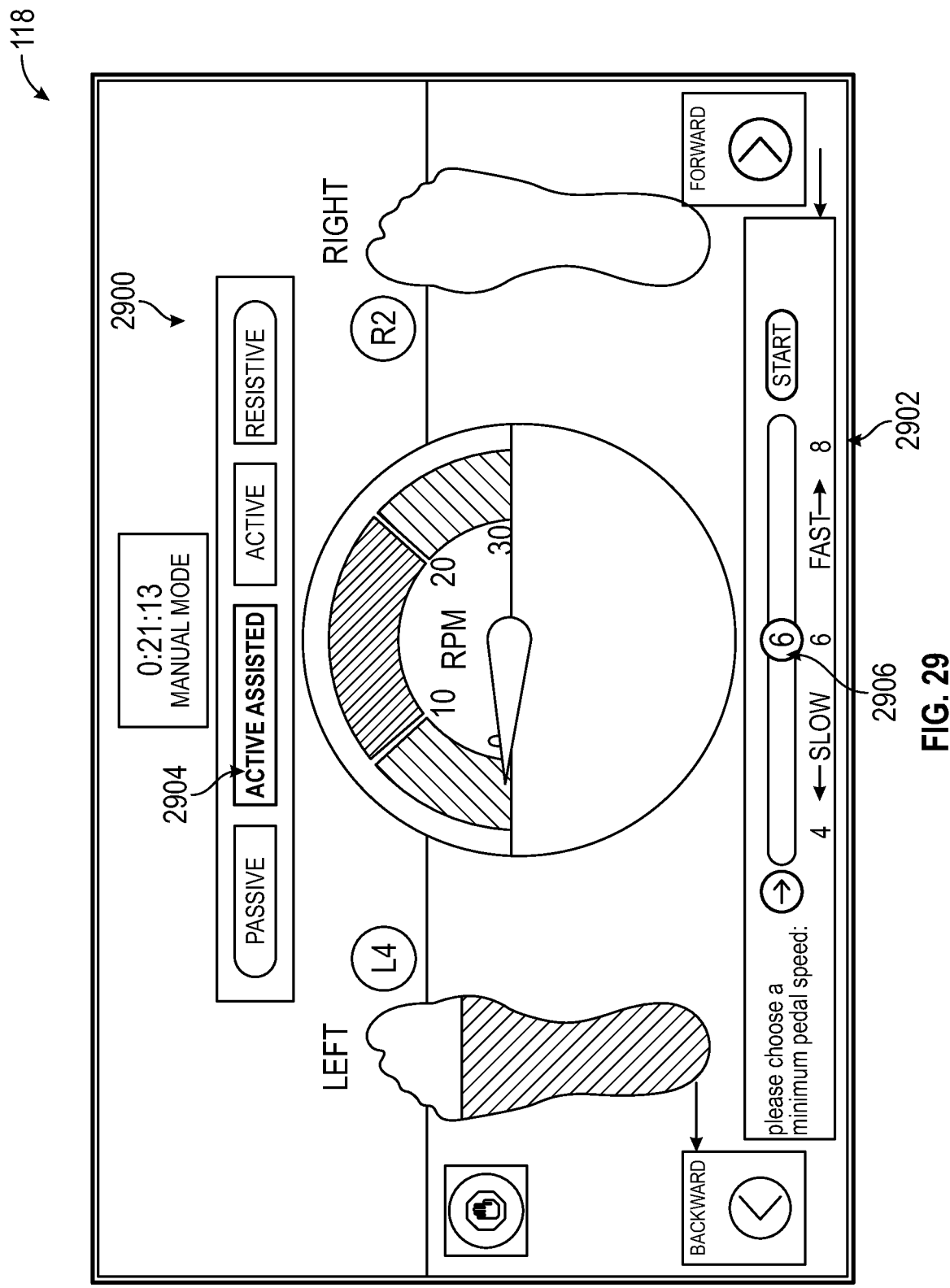
FIG. 29 generally illustrates an example user interface of the user portal, the user interface presenting an option to modify a minimum speed of the electromechanical device operating in the active-assisted mode according to principles of the present disclosure.

FIG. 29 generally illustrates an example user interface 2900 of the user portal 118, the user interface 2900 presenting an option 2902 to modify a minimum speed of the electromechanical device 104 operating in the active-assisted mode 2904 according to principles of the present disclosure. The user may slide button 2906 to adjust the minimum speed that the user should maintain before the electric motor 122 begins providing driving force.

Figure 30:
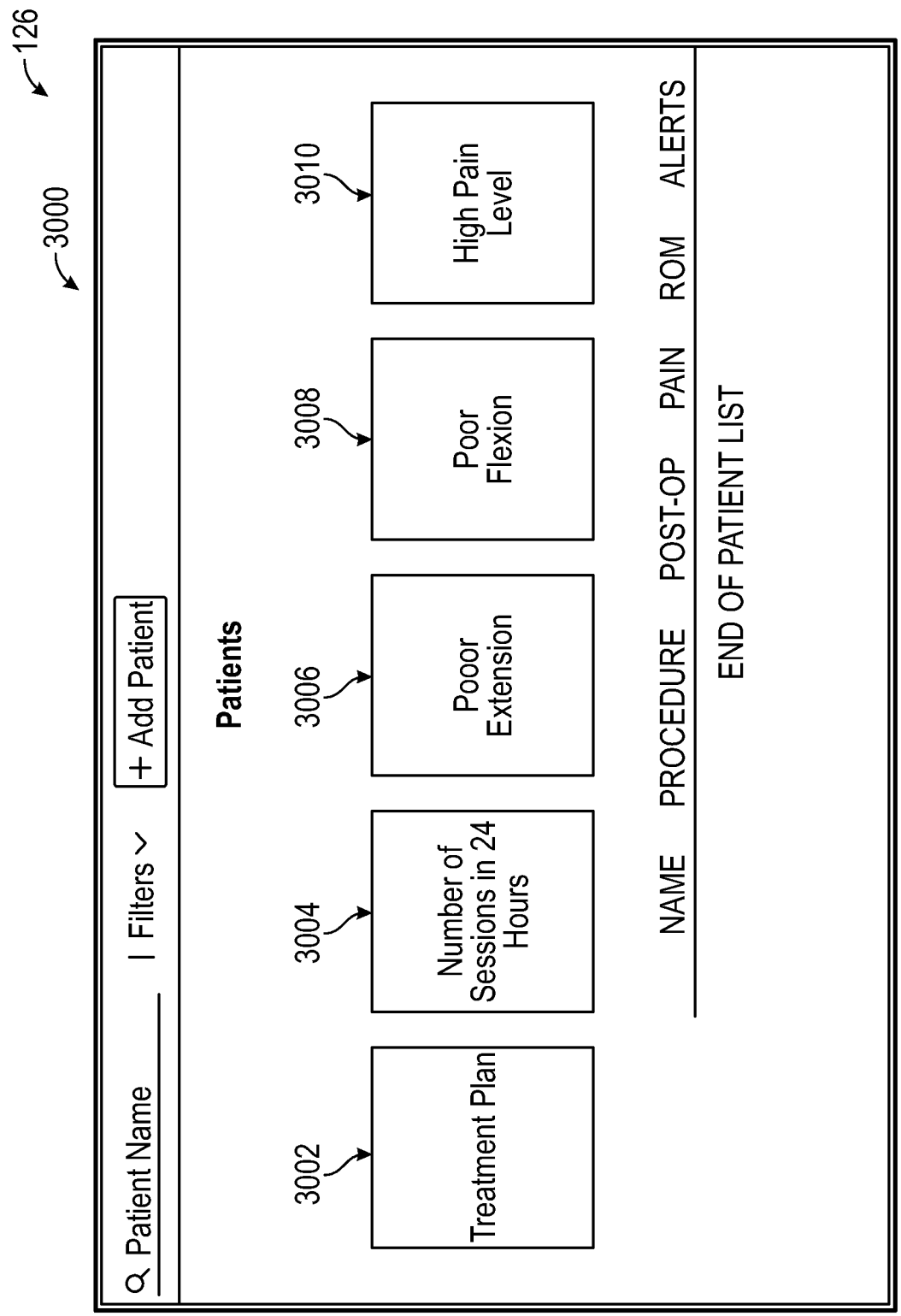
FIG. 30 generally illustrates an example user interface of the clinical portal, the user interface presenting various options available to the clinician according to principles of the present disclosure.

FIG. 30 generally illustrates an example user interface 3000 of the clinical portal 126, the user interface 3000 presenting various options available to the clinician/physician according to principles of the present disclosure. The clinical portal 126 may retrieve a list of patients for a particular physician who logs into the clinical portal 126. The list of patients may be stored on the computing device 114 or retrieved from the cloud-based computing system 116. A first option 3002 may enable the clinician to generate treatment plans for one or more of the patients, as described above. A second option 3004 may enable the clinician to view the number of sessions that each of the patients have completed in 24 hours. This may enable the clinician to determine whether the patients are keeping up with the treatment plan and send notifications to those patients that are not completing the sessions. A third option 3006 may enable the clinician to view the patients who have poor extension (e.g., angle of extension above a target extension for a particular stage in the treatment plan). A fourth option 3008 may enable the clinician to view the patients who have poor flexion (e.g., angle of bend below a target bend for a particular stage in the treatment plan). A fifth option 3010 may enable the clinician to view the patients reporting high pain levels. Regarding any of the options, the clinician can contact the user and inquire as to the status of their lack of participation, extension, flexion, pain level etc. The clinical portal 126 provides the benefit of direct monitoring of the patients progress by the clinician, which may enable faster and more effective recoveries.

Further, the clinical portal 126 may include an option to control aspects of operating the electromechanical device 104. For example, the clinician may use the clinical portal 126 to adjust a position of a pedal based on angles of extension/bend received from the computing device 102 and/or the goniometer 106 in real-time while the user is engaged in a pedaling session or when the user is not engaged in the pedaling session. The clinical portal 126 may enable the clinician to adjust the amount of resistance provided by the electric motor 122 in response to determining an amount of force exerted by the user exceeds a target force threshold. The clinical portal 126 may enable the clinician to adjust the speed of the electric motor 122, and so forth.

Figure 31:
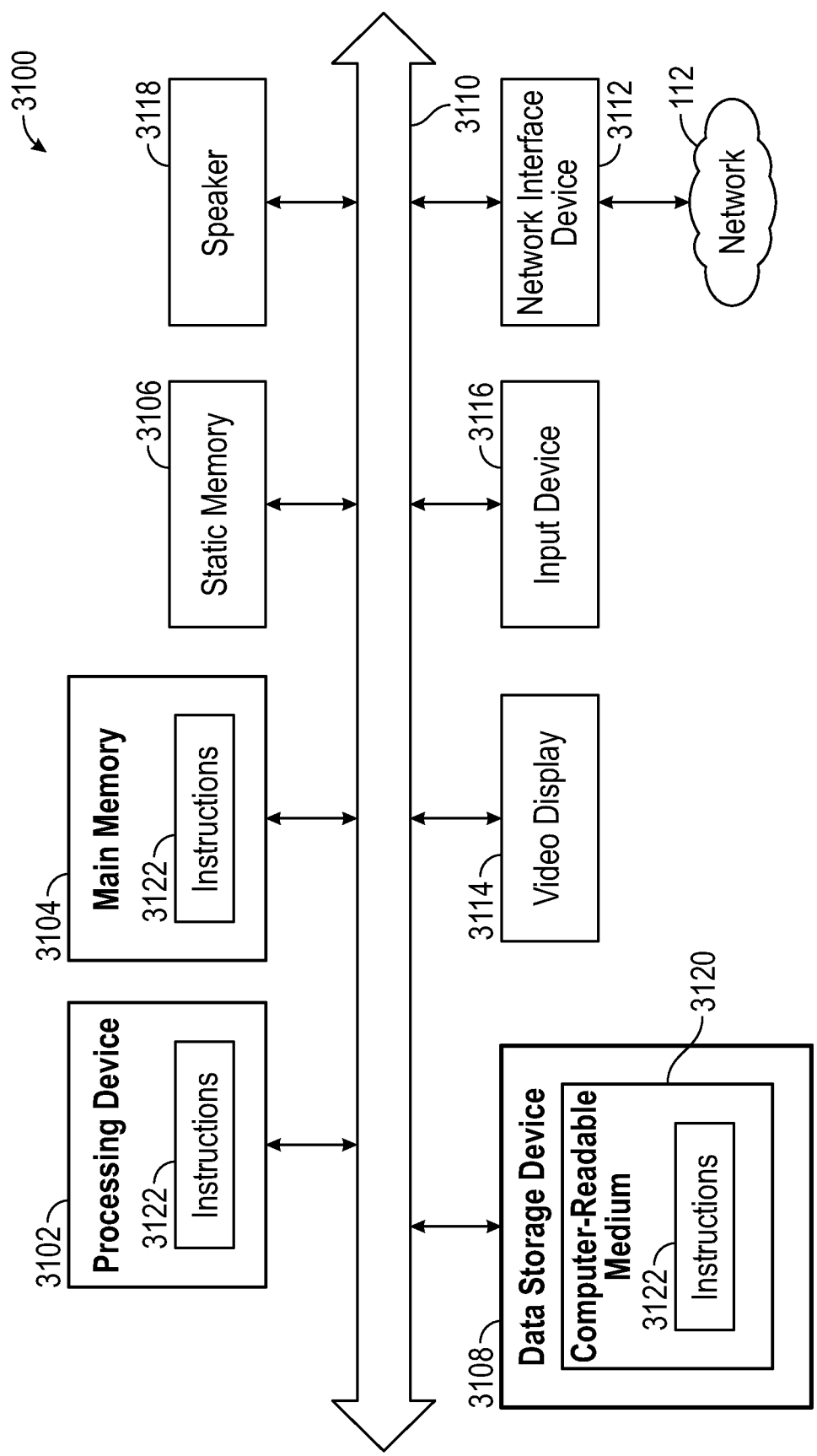
FIG. 31 generally illustrates an example computer system according to principles of the present disclosure.

FIG. 31 generally illustrates example computer system 3100 which can perform any one or more of the methods described herein, in accordance with one or more aspects of the present disclosure. In one example, computer system 3100 may correspond to the computing device 102 (e.g., user computing device), the computing device 114 (e.g., clinician computing device), one or more servers 128 of the cloud-based computing system 116, the training engine 130, the servers 128, the motor controller 120, the pedals 110, the goniometer 106, and/or the wristband 108 of FIG. 1. The computer system 3100 may be capable of executing user portal 118 and/or clinical portal 126 of FIG. 1. The computer system may be connected (e.g., networked) to other computer systems in a LAN, an intranet, an extranet, or the Internet. The computer system may operate in the capacity of a server in a client-server network environment. The computer system may be a personal computer (PC), a tablet computer, the motor controller 120, the goniometer 106, a wearable (e.g., wristband 108), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 3100 includes a processing device 3102, a main memory 3104 (e.g., read-only memory (ROM), flash memory, dynamic random access memory (DRAM) such as synchronous DRAM (SDRAM)), a static memory 3106 (e.g., flash memory, static random access memory (SRAM)), and a data storage device 3108, which communicate with each other via a bus 3110.

Processing device 3102 represents one or more general-purpose processing devices such as a microprocessor, central processing unit, or the like. More particularly, the processing device 3102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 3102 may also be one or more special-purpose processing devices such as an application specific integrated circuit (ASIC), a field programmable gate array (FPGA), a digital signal processor (DSP), network processor, or the like. The processing device 3102 is configured to execute instructions for performing any of the operations and steps discussed herein.

The computer system 3100 may further include a network interface device 3112. The computer system 3100 also may include a video display 3114 (e.g., a liquid crystal display (LCD) or a cathode ray tube (CRT)), one or more input devices 3116 (e.g., a keyboard and/or a mouse), and one or more speakers 3118 (e.g., a speaker). In one illustrative example, the video display 3114 and the input device(s) 3116 may be combined into a single component or device (e.g., an LCD touch screen).

The data storage device 3116 may include a computer-readable medium 3120 on which the instructions 3122 (e.g., implementing control system, user portal 118, clinical portal 126, and/or any functions performed by any device and/or component depicted in the FIGs. and described herein) embodying any one or more of the methodologies or functions described herein is stored. The instructions 3122 may also reside, completely or at least partially, within the main memory 3104 and/or within the processing device 3102 during execution thereof by the computer system 3100. As such, the main memory 3104 and the processing device 3102 also constitute computer-readable media. The instructions 3122 may further be transmitted or received over a network via the network interface device 3112.

While the computer-readable storage medium 3120 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

FIGS. 32A-32G generally illustrate an example prehabilitation system 3200 that utilizes machine learning to generate, monitor, and/or optimize a treatment plan, such as a prehabilitation plan of a patient. As will be described, the prehabilitation plan may be generated using a machine learning model trained on historical data, such as treatment data relating to a set of treatment plans of patients who have undergone (or that are undergoing) prehabilitation, rehabilitation, and/or any other type of health-related program that may be analyzed using machine learning to derive useful insights for generating an optimized prehabilitation plan for the patient. Nothing in this specification shall be construed to prevent the prehabilitation system 3200 being configured for purposes approved by veterinary healthcare professionals with respect to veterinary applications, and any veterinary application possible in hereby contemplated and any pronouns referring herein to humans may also be construed to apply to non-human animals.

A treatment plan, as used herein, may refer to a plan for a patient who is receiving treatment relating to a past, present, or future illness, condition, or ailment; an exercise plan, strength training plan, or endurance-increasing plan for an individual trying to improve his or her fitness; and/or any other plan capable of affecting the health of the patient. A treatment plan may, for example, include a prehabilitation plan for an individual who is to undergo surgery or who may have to undergo surgery at a later time period, a rehabilitation plan for a patient who has undergone surgery or who has a particular illness, condition, or ailment, and/or the like.

In some embodiments, the physician may prescribe a treatment plan that includes operating one or more electrical, mechanical, optic, electro-optical and/or electromechanical devices 104 (e.g., pedaling devices for arms or legs) for a period of time to exercise the affected area in an attempt to improve one or more characteristics of the affected body part and to attempt to regain as much normal operability of that affected body part as possible. For example, a treatment plan may include a set of pedaling sessions comprising use of the electromechanical device 104, a set of joint extension sessions, a set of flex sessions, a set of walking sessions, a set of heartrates achieved per pedaling session and/or walking session, and the like. Additionally, or alternatively, the treatment plan may include a medical procedure to perform on the patient, a treatment protocol for the patient using the electromechanical device 104, a diet regimen for the patient, a medical regimen for the patient, a sleep regimen for the patient, and/or the like.

Additionally, while one or more embodiments in FIGS. 32A-32G refer to a prehabilitation plan, it is to be understood that this is provided by way of example, and that in practice, the health management server 3202 may generate and recommend any type of treatment plan or health-related plan for any type of patient or user. Additional information regarding treatment plans is provided elsewhere herein. Furthermore, while one or more embodiments in FIGS. 32A-32G refer to preparation for surgery as a reason for a patient undergoing prehabilitation, it is to be understood that this is provided by way of example. In practice, any number of different health-related events may affect the health of a patient, such that there is a reason for the patient to undergo prehabilitation, rehabilitation, and/or any other health-related process. For example, one or more embodiments described herein may be applied to a patient who has an iatrogenic medical condition or side effects (e.g., de novo or exacerbated), whether pharmacologically, diagnostically, intentionally or omissively caused. The intensity of that iatrogenic medical condition may be of greater or lesser severity, and that degree of severity have an effect, likely concomitant, correlative or related in some manner, on a patient undergoing prehabilitation and/or rehabilitation.

The prehabilitation system 3200 may include a health management server 3202, the computing device 102, the electromechanical device 104, the goniometer 106, the wristband 108, and the computing device 114. The health management server 3202 may be part of the cloud-based computing system 116, and may include the one or more servers 128, the training engine 130, and one or more machine learning models (e.g., the one or more machine learning models 132).

Figure 32A:
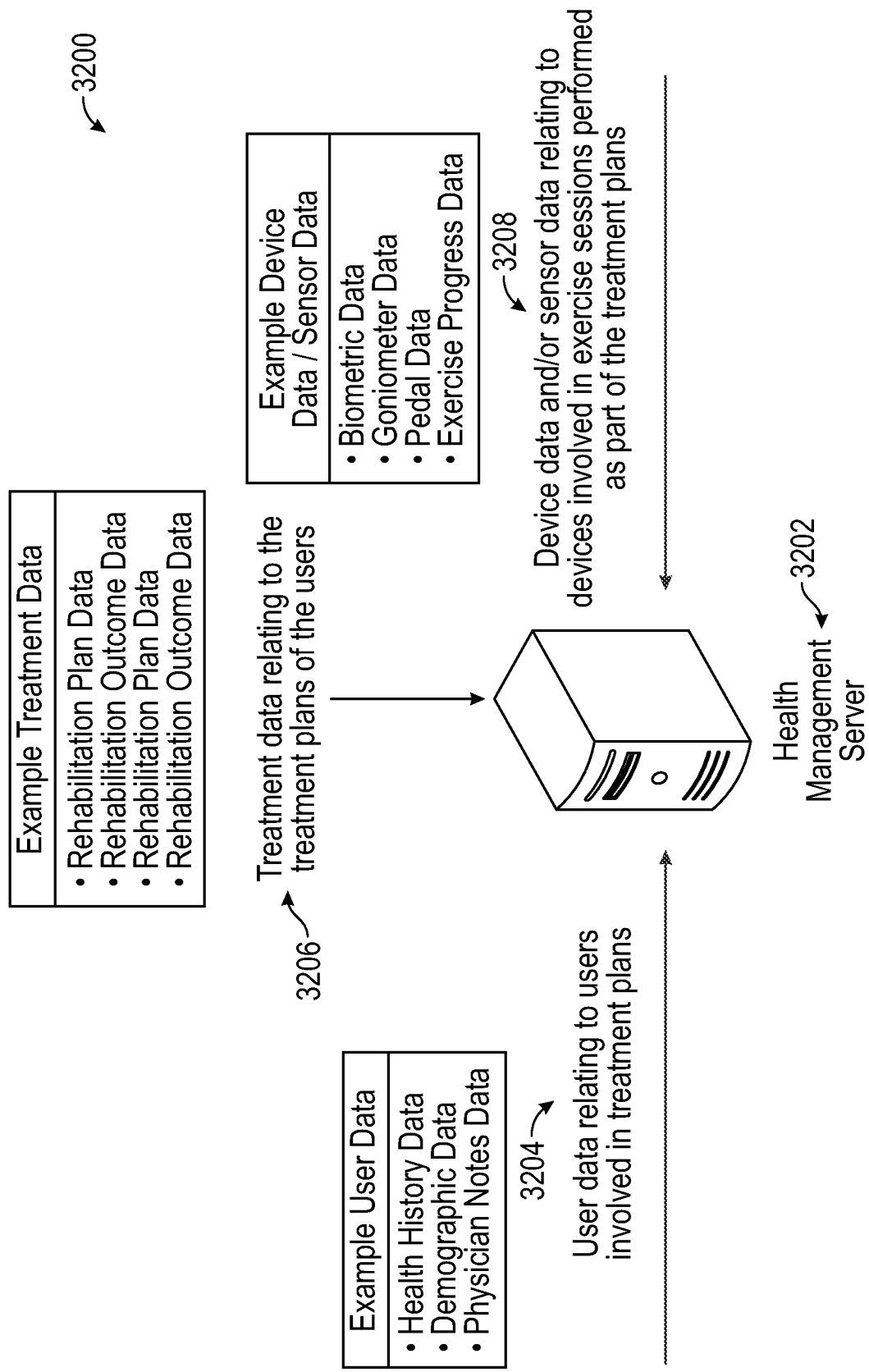

FIG. 32A generally illustrates the health management server 3202 receiving training data for training a machine learning model to generate prehabilitation plans for users (e.g., patients undergoing prehabilitation). For example, the health management server 3202 may receive training data from one or more data storage devices. The training data may be received via an application programming interface (API) and/or another type of communication interface. The training data may include user data for a group of users who received treatment relating to past, present, or future illnesses, conditions, or ailments, treatment data relating to a set of treatment plans and/or outcomes, device data and/or sensor data for devices (e.g., electromechanical devices 104) used for exercises performed as part of the treatment plans, and/or the like. The treatment data may include rehabilitation plan data relating to rehabilitation plans of a first group of users who have undergone rehabilitation for a condition, injury, or ailment; prehabilitation plan data relating to prehabilitation plans of a second group of users who are to undergo surgery or who may have to undergo surgery at a later time period; and/or the like.

As shown by reference number 3204, the health management server 3202 may receive user data relating to users involved in treatment plans. For example, the health management server 3202 may receive user data for the first group of users using or who have used various electromechanical devices 104 while undergoing rehabilitation for various conditions, injuries, and/or ailments. Additionally, or alternatively, the health management server 3202 may receive user data for the second group of users using or who have used various electromechanical devices 104 while undergoing prehabilitation. A user may undergo prehabilitation for any purpose approved of and/or prescribed by a healthcare professional, including, but not limited to, the following purposes: because of an upcoming health-related event (e.g., a surgery, etc.), to reduce the likelihood of experiencing a health-related event (e.g., an injury, such as a recurring injury) at a later time period, to improve one or more health indicators of the user, and/or for any other purpose contemplated by a healthcare professional and/or user. A treatment plan may have been completed by a user or the user may be in the process of completing the treatment plan.

User data for a user may include demographic data relating to one or more demographics of the user, health history data relating to one or more health indicators of the user, and/or the like. The demographic data may specify an age of the user, a race of the user, a sex of the user, an income of the user, and/or the like. The health history data may include data relating to a medical history of the user, data relating to a medical history of one or more family members of the user, data relating to a medical history of one or more individuals with whom the user has been in physical or otherwise proximate contact, data relating to a medical history of one or more physical locations (e.g., hospitals, outpatient clients, doctors' offices, etc.) where the user has physically been, and/or the like. For example, the health history data may include data that specifies one or more medical conditions of the user, allergies, vital signs recorded over one or more visits with a healthcare professional, notes taken by the healthcare professional, and/or any other information relating to the user's medical history. The health history data may include information collected before, during, and/or after undergoing prehabilitation and/or rehabilitation. The notes data may include data relating to a prognosis made by a physician, data relating to a patient description of the condition, injury, or ailment (e.g., symptoms, duration of symptoms, etc.), data relating to a pre-existing condition, injury, or ailment, and/or the like.

As shown by reference number 3206, the health management server 3202 may receive treatment data relating to treatment plans of the users. For example, the health management server 3202 may receive a first dataset of treatment data relating to rehabilitation plans of a first group of users undergoing or who have undergone rehabilitation for a condition, injury, or ailment. Additionally, or alternatively, the health management server 3202 may receive a second dataset of treatment data relating to prehabilitation plans of a second group of users who are to undergo surgery or who may have to undergo surgery at a later time period.

The treatment data may include treatment plan data relating to the treatment plans of the users and/or treatment outcome data relating to outcomes of the treatment plans. For example, the treatment data may include treatment plan data relating to a prehabilitation plan of a user who has completed (or is presently undergoing) prehabilitation, treatment outcome data relating to outcomes of the treatment plans, and/or the like. An outcome of a treatment plan may relate to a result of treatment, a health indicator or health status of a user after a treatment plan has been completed, feedback relating to the treatment plan (e.g., provided by the user, a healthcare professional, etc.), and/or the like.

A treatment plan (e.g., a prehabilitation plan, a rehabilitation plan, etc.) may include one or more exercise sessions that may be performed, using an electromechanical device 104, by the user. An exercise session may include one or more exercises the user can complete to strengthen, make more pliable, reduce inflammation and/or swelling in, and/or increase endurance in an area of the body, tasks the user can complete, a start date and end date for a treatment plan, goals relating to a treatment plan (e.g., dietary goals, sleep goals, exercise goals, etc.), description and/or identifier of a medical procedure that was performed (or that is to be performed) on the user, and/or the like. The one or more exercises may, for example, include a set of pedaling sessions to be performed using an electromechanical device 104, a set of joint extension sessions, a set of flex sessions, a set of walking sessions, a set of heartrates per pedaling session and/or walking session, and/or the like. For example, a patient undergoing prehabilitation may perform a pedaling session as part of a prehabilitation plan created to assist a patient in strengthening or improving a condition of one or more body parts which may be affected by an upcoming surgery, to strengthen or improve a condition of one or more body parts to reduce the chance of an injury at a later time period, and/or the like.

As shown by reference number 3208, the health management server 3202 may receive device data and/or sensor data relating to devices involved in exercise sessions performed as part of the treatment plans. For example, the health management server 3202 may receive device data from an electromechanical device 104. The device data may include data relating to a selected exercise session, data relating to a device configuration that corresponds to the selected exercise session, data relating to one or more user-selected preferences, and/or the like.

Additionally, or alternatively, the health management server 3202 may receive sensor data from one or more monitoring devices (e.g., the electromechanical device 104, the wristband 108, the goniometer 108, a pad, and/or the like). The one or more monitoring devices may be implemented while a patient is exercising to track patient progress, monitor one or more patient health indicators, and/or the like. The sensor data may include vital signs data, goniometer data, component data for one or more components of an electromechanical device 104, and/or the like. For example, a sensor of the electromechanical device 104 may measure a force exerted by a patient on the pedals 110 during an exercise session. Additionally, or alternatively, a sensor of the electromechanical device 104 may measure a distance traveled by the user during an exercise session (e.g., based on the number of pedal revolutions completed over an interval).

Additionally, or alternatively, a wristband 108 may capture a number of steps taken by a patient over an interval, may measure vital signs of the patient (e.g., heartrate, blood pressure, oxygen level, etc.), and/or the like. Additionally, or alternatively, a goniometer 106 may measure a range of motion (e.g., angles of extension and/or bend) of a body part to which the goniometer 106 is attached. Sensor data captured by the one or more monitoring devices may be provided to the health management server 3202.

In some embodiments, the health management server 3202 may receive one or more other types of training data. For example, the health management server 3202 may receive classification data relating to medical classifications of conditions, injuries, or ailments. The classification data may, for example, include a set of International Classification of Diseases and Related Health Problems (ICD) codes, such as ICD-10 codes, or Diagnosis-Related Group (DRGs) codes. Additionally, or alternatively, the health management server 3202 may receive feedback data relating to patient feedback of treatment plans, healthcare professional feedback relating to treatment plans, and/or the like.

Additionally, or alternatively, the health management server 3202 may receive safety data relating to a set of constraints approved by one or more healthcare professionals. For example, one or more of the treatment plans may have been configured to comply with a set of constraints, such as a first constraint relating to one or more maximum permissible ranges of motion on the electromechanical device 104, a second constraint relating to one or more maximum permissible resistances that can be applied to one or more components of the electromechanical device 104, a third constraint relating to one or more minimum measures of force permissible to apply to the one or more components of the electromechanical device 104, and/or the like.

In some embodiments, the training data may have been stored using one or more cloud storage devices. In some embodiments, the training data may be provided to the health management server 3202 in real-time or near real-time (e.g., provided periodically over a data collection time period). In some embodiments, the health management server 3202 may receive the training data from one or more cloud storage devices (e.g., rather than needing to be provided the training data in real-time throughout a data collection time period).

In some embodiments, the health management server 3202 may perform one or more pre-processing operations to standardize the training data. For example, to use the training data to train a machine learning model, the health management server 3202 may have to perform one or more pre-processing operations to standardize the training data to a uniform format (n.b. a "uniform format" may be referred to as a "canonical format" or a "canonical form," and the terms as meant as equivalents). As an example, the health management server 3202 may receive training data in multiple formats, multiple file types, and/or the like, and the health management server 3202 may convert one or more types of training data to a uniform format.

The health management server 3202 thus receives the training data that is to be used to train the machine learning model 132 to generate prehabilitation plans for users.

FIG. 32B generally illustrates the health management server 3202 training a machine learning model to generate prehabilitation plans for users. While one or more embodiments describe the machine learning model as being trained by the health management server 3202, it is to be understood that this is provided by way of example. In practice, another server or device may train the machine learning model (e.g., a desktop computer of a software developer, etc.) and may provide the trained machine learning model to the health management server 3202 or to another host device that allows the trained machine learning model to be accessed by the health management server 3202 (e.g., using an API or another type of communication interface).

As shown by reference number 3210, the health management server 3202 may train the machine learning model to generate prehabilitation plans for users. For example, the health management server 3202 may train the machine learning model to generate prehabilitation plans optimized for each user, that reduce the likelihood of the user experiencing a health-related event, that reduce the effect of the health-related event, that improve one or more health indicators of the user (e.g., ROM, strength, endurance, etc.), and/or the like.

In some embodiments, a prehabilitation plan for the user may be an optimal prehabilitation plan based on a likelihood that one or more exercise sessions of the prehabilitation plan, if performed by the user, will improve a health indicator (e.g., ROM, strength, endurance, etc.) of the user. Additionally, or alternatively, a prehabilitation plan for a user may be an optimal prehabilitation plan based on a likelihood that one or more exercise sessions, if performed by the user, will reduce a likelihood of the user experiencing an adverse health-related event (e.g., an injury, ailment, etc.) and/or will reduce an effect of the adverse health-related event were the adverse health-related event to occur. It is to be understood that these are provided by way of example. In practice, any number of different values may be implemented to define an optimal prehabilitation plan.

A machine learning model, as used herein, may refer to a framework able to apply one or more machine learning techniques to analyze input values and to generate output values that are to be used to generate prehabilitation plans and/or modifications to prehabilitation plans that are optimal for users. In some embodiments, a machine learning model may be supported by a data structure such as a data model. For example, a data model may be a structural framework that is organized according to one or more schemata. A machine learning model may use the data model by applying one or more machine learning techniques to the data model to generate output values or to identify specific data points. The one or more machine learning techniques may include one or more supervised machine learning techniques, one or more unsupervised machine learning techniques, one or more reinforcement-driven machine learning techniques, and/or the like. For example, the one or more machine learning techniques may include a classification technique, a regression technique, a clustering technique, and/or any other technique that may be used to train the machine learning model.

In some embodiments, the machine learning model may include a graphical machine learning model, such as a Markov decision process (MDP), a Hidden Markov Model (HMM), a Gaussian Mixture Model (GMM), a model based on a neural network, and/or the like. While one or more embodiments described below refer to the machine learning model as including an MDP, it is to be understood that this is provided by way of example. In practice, the machine learning model may include a neural network, any other type of model driven by machine learning, or any combination of models.

In some embodiments, to train the machine learning model to include an MDP, the health management server 3202 may be configured with (or may generate) a data structure that includes a set of decision states (referred to hereafter as states) and a set of state transitions. An example illustration is provided in FIG. 32B. The set of states may represent steps or features of prehabilitation plans, and may include an initial state, sets of intermediary states, and a set of final states. The initial state may include state parameters relating to characteristics of a user before, during, and/or after a health-related event occurs. In some embodiments, the initial state parameters may define characteristics of the user before, during, and/or after a trial exercise session is completed. The state parameters for the initial state may include user data, such as user data relating to demographic information, patient health history (e.g., pre-existing conditions, information impacting overall health, such as whether the user is an athlete, etc.), user vital signs (e.g., a heartrate, a blood pressure level, an oxygen level, and/or the like), physical capabilities of the user (e.g., a range of motion (ROM) of the user, a force the user applied to one or more pedals 110 while exercising on an electromechanical device 104, etc.), and/or the like.

In some embodiments, one or more sets of intermediary states may be used to define steps or features of a prehabilitation plan. For example, an intermediary state may include state parameters relating to characteristics of steps or features of the prehabilitation plan. For example, the intermediary state parameters may include a state parameter relating to a duration of an exercise session, a state parameter relating to a mode in which the electromechanical device 104 is to engage and/or a duration during which the electromechanical device 104 is to be engaged in that mode, a state parameter identifying a target heartrate for a patient while performing the exercise session, and/or the like. Additionally, or alternatively, the intermediary state parameters may include state parameters relating to instructions for aerobic exercises performed off the electromechanical device 104, such as instructions for a joint extension session, instructions for a flex session, and/or the like.

In some embodiments, the final states may include state parameters relating to specific prehabilitation plans that can be selected for or presented to a user. For example, the final states may include state parameters, such as exercise session identifiers, where such state parameters relate to a variety of different exercise sessions (and/or a variety of variations to an exercise session). The exercise sessions may, for example, vary based on the degree of progress the patient has made in the prehabilitation process, the physical fitness of the patient, whether the patient has had any injuries or recurring injuries, a severity of the injuries or recurring injuries, and/or the like.

To provide a specific example in the field of orthopedics, and without limiting applications in any other medical discipline performed by a healthcare professional, a user may have previously torn an ACL and may want to use prehabilitation to reduce the likelihood of a second ACL tear. In this case, the final states of the machine learning model may include prehabilitation plans with exercise sessions that relate to corresponding rehabilitation exercise sessions for patients recovering from an existing ACL tear, prehabilitation plans with exercise sessions that improve one or more health indicators of the user (e.g., such as by strengthening one or more muscles or tendons around the knee), and/or the like. A prehabilitation exercise session may be said to relate to a corresponding rehabilitation exercise session based on the prehabilitation exercise session's being identical to, modeled after, and/or sharing a threshold number of characteristics and/or features with the rehabilitation exercise session.

While one or more examples described herein refer to a patient who has recovered from an existing ACL tear and who is using prehabilitation to reduce the likelihood of reinjuring his or her ACL, it is to be understood that this is provided only by way of example. In practice, a patient may undergo prehabilitation for a variety of different reasons. For example, a patient may need surgery and may be using prehabilitation pre-operatively to reduce swelling, improve ROM, and/or the like.

In some embodiments, the one or more sets of intermediate states may be segmented into layers. For example, the layers may include a first layer with a subset of states that represent durations of prehabilitation plans and/or durations of different parts of the prehabilitation plans, a second layer with a subset of states that represent modes of the electromechanical device 104 and/or configuration values for one or more configurations that can be implemented during an exercise session, a third layer with a subset of states that each represent a target number of pedals 110 for the patient to make over an interval, a fourth layer with a subset of states that each represent a target heartrate of the patient over the interval, and/or the like. It is to be understood that this is provided by way of example, and that in practice, the set of states may be segmented into any number of finite layers or related using any number of different data types and/or logical schemes.

In some embodiments, the data structure (e.g., a data model) supporting the MDP may relate states to each other using a set or sets of state transitions. In some embodiments, a state transition may include a value that represents a probability that transitioning from a source state to a destination state will be an optimal transition (e.g., relative to one or more other transition values relating to the destination state). For example, a set of intermediary states may represent proposed durations of an exercise session. Each respective state may be initially configured with equal probability values. As will be described, certain input values may cause the probability values to change in order to recommend an optimal prehabilitation plan for a user. For example, if a user has a history of injuries, exercising for long time periods may increase a likelihood of injury or re-injury. In this example, the health management server 3202 may train the machine learning model such that lower probability values are assigned to states with longer exercise session durations (e.g., based on the longer exercise session durations being linked to increased risk of injury or re-injury).

One or more embodiments herein refer to probabilities or probability values. It is to be understood that this is provided by way of example, and that in practice, the state transitions of the MDP may be implemented using one or more nonparametric (i.e., ranked) means. Further, the probabilities or probability values may, in one or more embodiments herein, represent Bayesian probabilities.

In some embodiments, the health management server 3202 may train the machine learning model to generate prehabilitation plans for users. For example, the health management server 3202 may process the training data using one or more machine learning techniques, such that the machine learning model is configured to receive training data values and, based on the training data values, to assign state transition probabilities to state transitions. The health management server 3202 may select a combination of states associated with highest state transition probabilities, where selected states collectively represent a prehabilitation plan generated for a user. Additionally, the health management server 3202 may compare state data for the selected states with outcome data for known outcomes in order to indicate whether certain prehabilitation plans were successful, to indicate a degree to which said plans were successful, to indicate a degree to which said plans were optimal for a particular user or characteristic of a user, and/or the like. Based on comparing the state data with the outcome data, the health management server 3202 may update programming used to assign the state transition values. For example, the health management server 3202 may update programming by adjusting threshold values used to assign the state transition values. The state transition values may relate to or may be used to generate a set of machine learning scores, as described below.

A machine learning score may relate to, without limitation, a risk value (e.g., a risk score), a configuration value (e.g., a configuration score, such as a score for a configuration of the electromechanical device 104), and/or any other score or value capable of being used to generate a machine learning score. The risk value and/or the configuration value may be represented as a probability value, a confidence interval, a non-probabilistic value, a numerical value, a summation, an expected value, and/or the like. For example, a machine learning score may relate to a risk score that represents a probability of a change to a health indicator of the user. To provide a specific example, if a device configuration is implemented on the electromechanical device 104 while the user performs the exercise session, a risk score may represent a probability that the user will experience a health-related event, such as an injury, while performing the exercise session (or at a time period after the exercise session has been performed).

Additionally, or alternatively, and provided as another example, a configuration score may represent a probability that an implemented device configuration (e.g., implemented on an electromechanical device 104) is an optimal device configuration for a user. Additionally, or alternatively, a configuration score may represent a probability that a modification to the implemented device configuration is an optimal modification. A device configuration may be optimal (or a modification may be optimal) based on a likelihood of the device configuration or modification improving and/or maximizing, given a particular context, a health indicator of a user. For example, depending on the context, a device configuration may be optimal if the device configuration improves or maximizes a recovery time and/or life expectancy of the user, improves or maximizes a ROM of the user, and/or that improves or maximizes any other value or metric capable of measuring a health indicator of the user. Context that can affect optimality may include demographic information, medical history, accessibility to medical care, user work ethic, and/or the like.

In some embodiments, the health management server 3202 may train the machine learning model such that the machine learning model is configured to generate real-time modifications to a prehabilitation plan. For example, the health management server 3202 may receive training data that includes sensor data related to progress users have made in prehabilitation plans. In this example, the health management server 3202 may use one or more machine learning techniques to process the sensor data and to generate, based on processing the sensor data, one or more configuration scores. The one or more configuration scores represent one or more probabilities that an implemented device configuration is an optimal device configuration for a user and/or that represent one or more probabilities that a modification to the implemented device configuration is an optimal modification.

In some embodiments, a first module of the machine learning model may be trained to generate a prehabilitation plan and a second module of the machine learning model may be trained to generate real-time or near real-time modifications to the prehabilitation plan. In some embodiments, a first machine learning model may be trained to generate the prehabilitation plan and a second machine learning model may be trained to generate the real-time or near real-time modifications to the prehabilitation plan. Generation or transmission of data may occur in real-time or near real-time. Real-time may refer to less than 2 seconds, or any other suitable amount of time. "Real-time" may also refer to near real-time, which may be less than 10 seconds or any reasonably proximate difference between two different times. Near real-time may refer to any interaction of a sufficiently short time to enable two individuals to engage in a dialogue via a user interface, and will generally be less than 10 seconds (or any suitably proximate difference between two different times) but greater than 2 seconds. For example, near real-time may include a range of 2-5 seconds, 2-10 seconds, or any other suitable amount of time.

In this way, the health management server 3202 trains the machine learning model to be able to generate prehabilitation plans for users and/or updates to prehabilitation plans for the users.

Figure 32C:
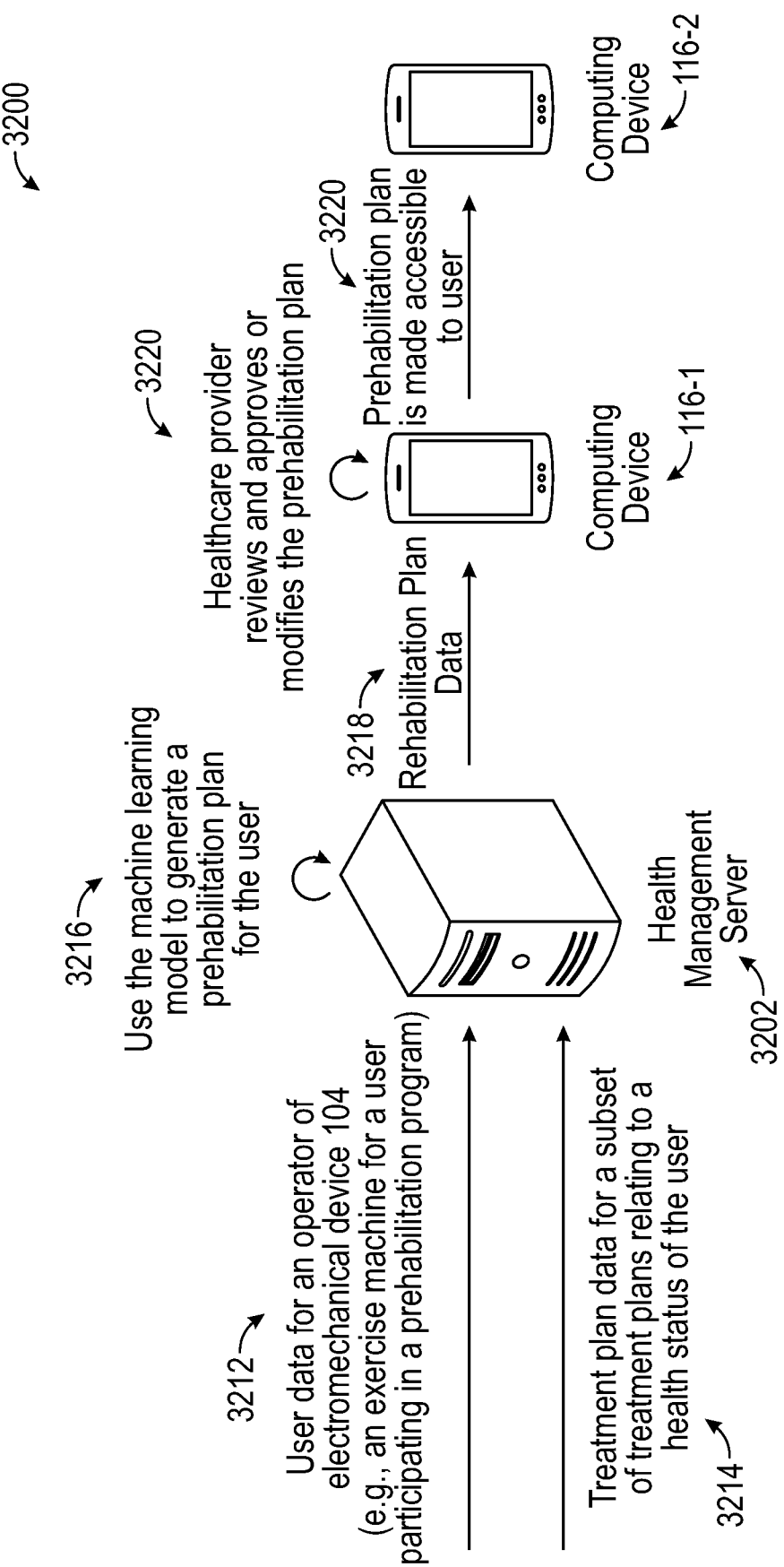

FIG. 32C generally illustrates the health management server 3202 using machine learning to determine a prehabilitation plan for a patient undergoing prehabilitation. As shown by reference number 3212, the health management server 3202 may receive user data relating to the patient. The patient (also referred to hereafter as a user) may be a user or an operator of the electromechanical device 104. For example, the user may have (or may have previously had) an injury and may want to reduce the risk of a recurring injury by taking part in a prehabilitation program. By having the user exercise on the electromechanical device 104, the prehabilitation program may reduce the risk of the recurring injury. The user data of the user may be provided to the health management server 3202 to allow the health management server 3202 to process the user data when generating the prehabilitation plan.

In some embodiments, the user may interact with the user portal 118 to consent to have the user data of the user provided to the health management server 3202. For example, the user may have access to a patient portal used to sign up for the prehabilitation program. The user portal 118 may request that the user consent to providing user data such that the user data may be processed and used to recommend an optimal prehabilitation plan. In some embodiments, a healthcare professional may interact with the clinical portal 126 to provide the health management server 3202 with the user data. For example, the user may have provided consent and a healthcare professional may interact with an interface of the clinical portal 126 to provide the health management server 3202 with the user data.

In some embodiments, the health management server 3202 may already store the user data (e.g., using a data structure) or may already have access to the user data via any suitable source. In this case, the health management server 3202 may reference the data structure or suitable source to identify or obtain the user data for further processing.

While one or more embodiments describe a prehabilitation plan for the user to reduce the likelihood of the user reinjuring a particular body part, it is to be understood that this is provided by way of example. In practice, the health management server 3202 may generate prehabilitation plans for any number of different health related reasons, such as to prevent an injury that may be at risk of occurring but which has in fact yet to occur, to improve a condition of the user, to improve an overall health status of the user, and/or the like. Furthermore, in some embodiments, the health management server 3202 may generate one or more other types of health improvement plans, such as rehabilitation plans, exercise plans, and/or the like.

As shown by reference number 3214, the health management server 3202 may receive (or obtain) treatment data for a subset of treatment plans relating to a health status or health indicator of the user. For example, a data structure may include a master set of treatment data that includes treatment data for treatment plans relating to a number of different conditions, injuries, and/or ailments. The data structure may associate treatment data relating to each treatment plan with one or more identifiers that relate to each respective condition, injury, or ailment that may be treated by a given treatment plan.

In some embodiments, to obtain a subset of treatment plans relating to a condition, injury, or ailment of the user, an authorized device may reference the data structure using an identifier relating to a condition, injury, or ailment of the user. The authorized device may be the health management server 3202, a computing device 116-1 (e.g., a device used by the healthcare professional), a computing device 116-2 (e.g., a device used by the user), and/or another device. For example, the health management server 3202 may receive the user data for the user, where the user data includes an injury identifier relating to the recurring injury of the user. In this case, the health management server 3202 may use the injury identifier to reference the data structure to identify a subset of treatment plans relating to the recurring injury of the user.

As shown by reference number 3216, the health management server 3202 may use the machine learning model to generate a prehabilitation plan for the user. For example, the health management server 3202 may provide the user data and the treatment data as inputs to the machine learning model to cause the machine learning model to generate a set of machine learning scores.

In some embodiments, the set of machine learning scores may relate to probabilities of a given device configuration (e.g., of the electromechanical device 104) being suitable for a given application or applications for the user. For example, a device configuration may be suitable for a given user application based on the device configuration corresponding to a threshold probability of improving performance of an area of the user's body that would be affected if the user's injury were recur. To provide another example, a device configuration may be suitable for a given user application based on the selected device configuration corresponding to a threshold probability of preventing a health-related event from occurring with respect to the user. Additionally, or alternatively, the set of machine learning scores may include one or more risk scores relating to probabilities of a change in one or more health indicators of the user, one or more configuration scores relating to different prehabilitation plans being an optimal prehabilitation plan for the user, and/or the like.

As an example, the health management server 3202 may receive health history data for the user that includes data relating to the user having a history of recurring knee problems, data relating to the user having above average physical strength and conditioning, data relating to the user having a history of participating in sports, and/or the like. Furthermore, the health management server 3202 may receive treatment data relating to a subset of treatment plans used to treat recurring knee injuries. In this example, the health management server 3202 may provide the user data and the treatment data as inputs to the machine learning model to cause the machine learning model to generate a set of machine learning scores. The set of machine learning scores may correspond to the subset of available prehabilitation plans (e.g., which may include device configurations for exercise sessions performed on the electromechanical device 104), where one of the machine learning scores represents a highest probability of a given prehabilitation plan being an optimal prehabilitation plan for the user.

As shown by reference number 3218, the health management server 3202 may provide prehabilitation plan data to the computing device 116-1. For example, the health management server 3202 may provide the computing device 116-1 with prehabilitation plan data relating to one or more prehabilitation plans that are part of the subset of prehabilitation plans. The computing device 116-1, as described above, may be a device accessible to a healthcare professional. The prehabilitation plan may be provided via a communication interface, such as an API or another type of communication interface. In some embodiments, the health management server 3202 may provide the computing device 116-1 with prehabilitation plan data relating to the prehabilitation plan that has the highest probability of being the optimal prehabilitation plan for the user. In some embodiments, the health management server 3202 may provide the computing device 116-1 with prehabilitation plan data relating to one or more prehabilitation plans that correspond to one or more machine learning scores that satisfy a threshold machine learning score.

As shown by reference number 3220, the healthcare professional may interact with the computing device 116-1 to review, modify, and/or approve the prehabilitation plan. In some embodiments, the healthcare professional may, during a telemedicine session or telehealth session, interact with the interface of the clinical portal 126. In some embodiments, the healthcare professional may interact with an interface of the clinical portal 126 to review and approve the prehabilitation. In this case, the interface may display the prehabilitation plan and the healthcare professional may review and submit the healthcare professional's approval of the prehabilitation plan.

In some embodiments, the healthcare professional may interact with the interface of the clinical portal 126 to modify and approve the prehabilitation plan. In this case, the interface may display the prehabilitation plan and the healthcare professional may interact with the interface by marking up the prehabilitation plan, by selecting one or more modifications from a drop-down menu, by inputting one or more modifications as free-form text, and/or the like.

In some embodiments, the healthcare professional may interact with the interface of the clinical portal 126 to reject the prehabilitation. In this case, the healthcare professional may interact with the interface to input one or more suggested changes for generating a new prehabilitation plan. When the healthcare professional finalizes the one or more suggested changes, data relating to the suggestions may be provided back to the health management server 3202. The health management server 3202 may then use the one or more suggestions to retrain the machine learning model such that programming used to generate outputs may be updated based on such suggestions.

As shown by reference number 3222, the computing device 116-1 may provide, to the computing device 116-2, prehabilitation plan data for the approved prehabilitation plan. The computing device 116-2 may, for example, be a device accessible to the user. In some embodiments, the computing device 116-1 may provide the approved prehabilitation plan to the user portal 118 accessible to the user. Additionally, or alternatively, the computing device 116-1 may provide the approved prehabilitation plan to the computing device 116-2 as an image in a short message service (SMS) message or a private messenger (e.g., Telegram, Signal, skype, Google Hangouts, Facebook Messenger, WickrPro, WickrMe, WhatsApp, snapchat, Instagram, etc.) message. Additionally, or alternatively, the approved prehabilitation plan may be provided to an e-mail account associated with the user and/or to one or more other accounts associated with the user.

In this way, the health management server 3202 generates the prehabilitation plan using machine learning and enables the prehabilitation plan to be provided to a reviewing healthcare professional and to the user. In other situations, the electromechanical device 104 may generate the prehabilitation plan. For example, a lightweight machine learning model may be hosted or supported by the electromechanical device 104 (e.g., rather than by the health management server 3202), such that the electromechanical device 104 may generate the prehabilitation plan. The prehabilitation plan may be generated based on the electromechanical device 104 receiving a request from a device of a healthcare professional, based on a user uploading user data and/or other related data about the user's health history, and/or via another type of trigger.

Figure 32D:
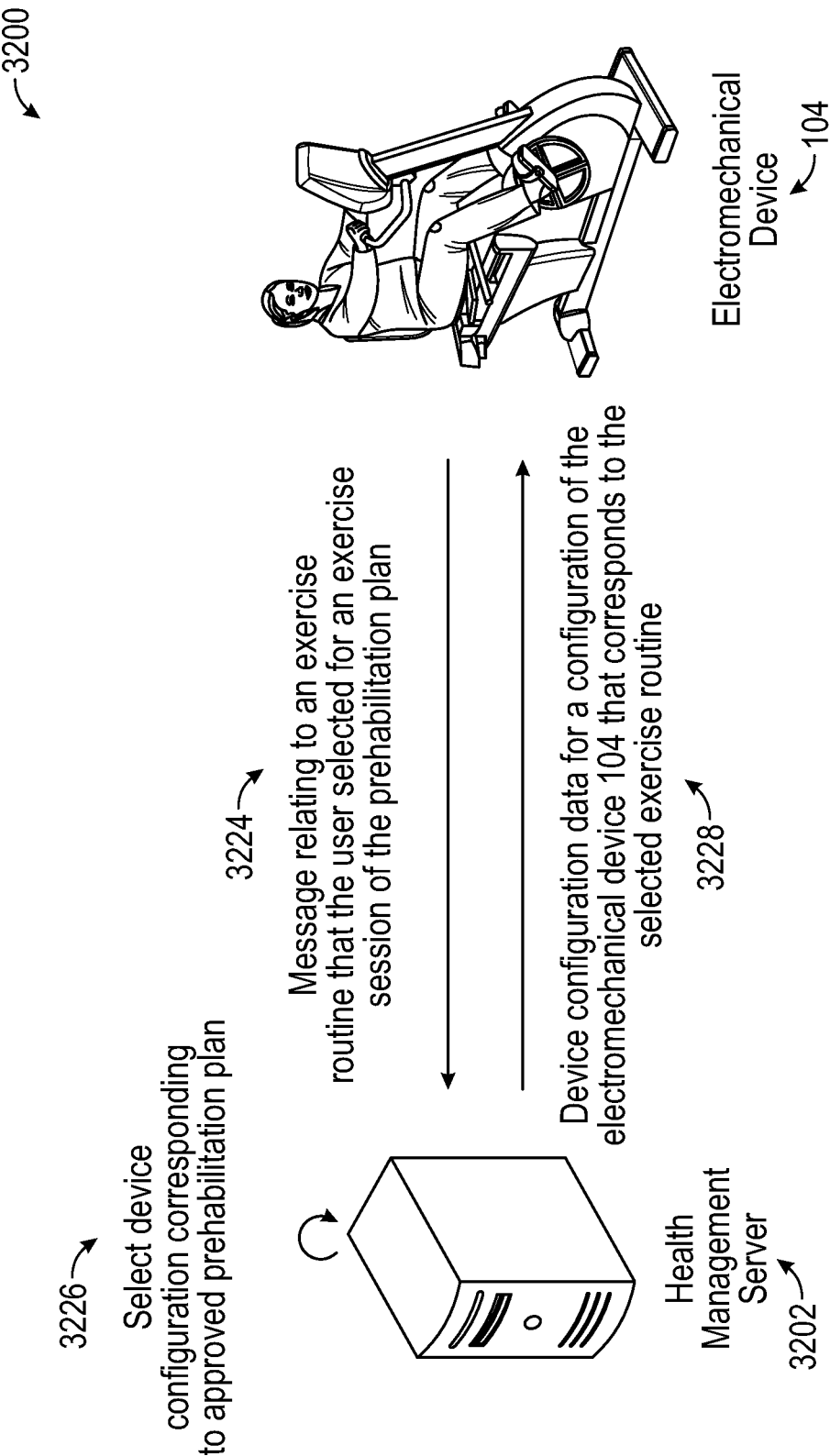

FIG. 32D generally illustrates the electromechanical device 104 implementing a device configuration corresponding to an exercise session of the approved prehabilitation plan. As shown by reference number 3224, the electromechanical device 104 may provide, to the health management server 3202, a message relating to an exercise session that the user selected for an exercise session of the prehabilitation plan. For example, the user may interact with an interface of the electromechanical device 104 that displays exercise sessions capable of being performed by the user. In this case, the user may select an exercise session specified in the prehabilitation plan, such that the message relating to the exercise session is provided to the health management server 3202.

As shown by reference number 3226, the health management server 3224 may select the device configuration corresponding to the exercise session of an exercise session of the prehabilitation plan. For example, the health management server 3202 may use an exercise session identifier to reference a data structure that associates the exercise session identifier with a corresponding device configuration.

The device configuration may include mode data related to one or more modes in which the electromechanical device 104 is capable of operating during the exercise session. The mode data may include a first component configuration including data related to one or more positions at which to configure one or more components of the electromechanical device 104, a second component configuration including data related to one or more forces to apply to the one or more components of the electromechanical device 104, a user interface configuration including data related to exercise instructions for the exercise session, wherein the exercise instructions are capable of being provided for display via an interface, and/or the like. The first component configuration may define a position at which to configure a seat of the electromechanical device 104, a position at which to configure one or more pedals 110 of the electromechanical device 104, and/or the like.

As shown by reference number 3228, the health management server 3226 may provide the device configuration corresponding to the exercise session of the prehabilitation plan to the electromechanical device 104. For example, the device configuration may be provided to the electromechanical device 104 to enable the electromechanical device 104 to implement the device configuration. In some embodiments, the electromechanical device 104 may receive the device configuration data from another device. For example, the computing device 116-1 may, upon the healthcare professional's approval of the prehabilitation plan, provide the electromechanical device 104 with device configuration data corresponding to the selected exercise session.

In some embodiments, the electromechanical device 104 may implement the device configuration. For example, the electromechanical device 104 may implement the device configuration to adjust a position of a seat, to adjust a position of one or more pedals 110, to adjust a position of one or more brake mechanisms, to power on one or more motors (e.g., an electric motor, a stepper motor, and/or the like), to power on one or more sensors, to display exercise instructions for the exercise session on an interface associated with the electromechanical device 104, and/or the like.

Additionally, or alternatively, the electromechanical device 104 may implement the device configuration such that an assisting force may be applied to the one or more pedals 110. For example, a motor or related component may be configured such that torque is applied to the one or more pedals 110 to assist the user in rotating the pedals 110. The assisting force may be applied based on a trigger condition being satisfied. For example, the assisting force may be applied while the user is performing the exercise session, while a position of a pedal is at a certain angle (e.g., such that the assisting force is applied for a portion of the total 360-degree rotation of the pedal), based on a user interacting with a user interface to request the assisting force, and/or the like.

Additionally, or alternatively, the electromechanical device 104 may implement the device configuration such that a resistive force may be applied to the one or more pedals 110. For example, one or more braking mechanisms may be configured such that a resistive force increases an amount of force needed by the user to rotate the one or more pedals 110. The resistive force may be applied based on a trigger condition being satisfied.

Additionally, or alternatively, the electromechanical device 104 may implement the device configuration such that the user, when performing one or more exercises of the exercise session, is enabled to repeat one or more motions associated with developing or improving muscle memory. For example, the electromechanical device 104 may implement a device configuration that enables the user to repeat motions that can be made to assist in preventing an ACL tear from ever occurring (e.g., such as by strengthening muscles and/or tendons around the knee). As another example, the electromechanical device 104 may implement a device configuration that enables the user to repeat motions that might be made after an ACL tear occurs (e.g., motions made as part of an exercise of a rehabilitation program). In this example, the user is enabled to develop or improve muscle memory of motions restricted so as to mirror or simulate, had the user torn an ACL, the user's ROM, strength, flexibility, etc.

Additionally, or alternatively, the electromechanical device 104 may implement the device configuration such that one or more sensors may be configured to monitor progress of the user while the user is performing the exercise session. For example, the one or more sensors may be configured to monitor and report vital signs of the user, angles of extension of bend of at least one body part of the user, force the user applies to the one or more pedals 110, and/or the like.

In this way, the electromechanical device 104 is enabled to implement the device configuration.

Figure 32E:
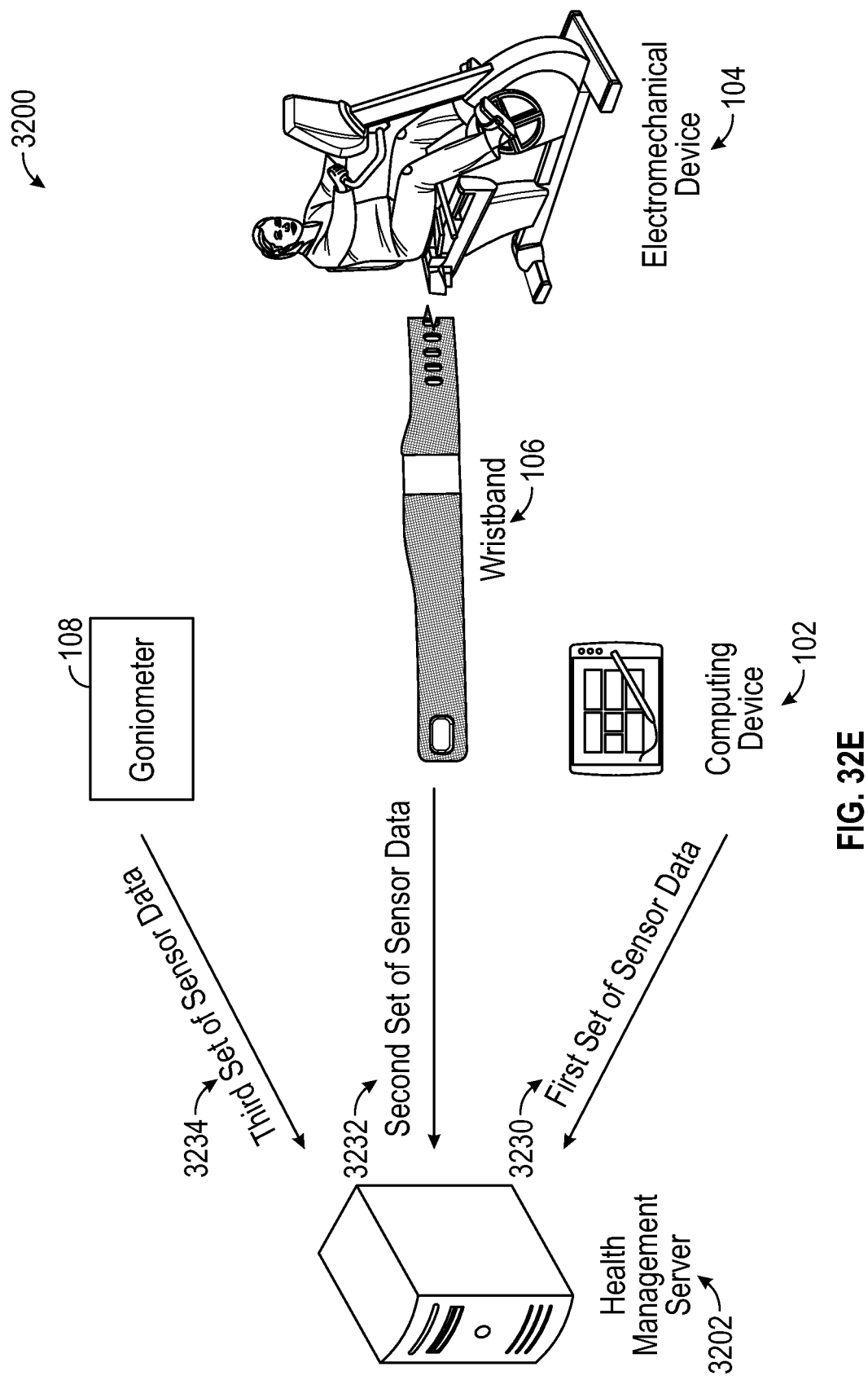

FIG. 32E generally illustrates one or more sensors capturing and providing sensor data to the health management server 3202. The sensor data may be related to determining the user's progress in the prehabilitation plan.

As shown by reference number 3230, the computing device 102 may provide a first set of sensor data to the health management server 3202. For example, one or more sensors, such as one or more strain gauges, may be configured to measure a force that the user applies to one or more pedals 110 of the electromechanical device 104. This allows the computing device 102 to provide the health management server 3202 with a first set of sensor data related to one or more measurements of force that the user applies to the one or more pedals 110.

As shown by reference number 3232, the wristband 108 may provide a second set of sensor data to the health management server 3202. For example, the wristband 108 may include sensors such as an accelerometer, a gyroscope, an altimeter, a light sensor, a pulse oximeter, and/or the like. The sensors of the wristband 108 may generate the second set of sensor data by monitoring the user throughout the exercise session and a processor of the wristband 108 may provide the second set of sensor data to the health management server 3202.

As an example, the wristband 108 may be configured to use the light sensor to detect a heart rate of the user. Additionally, or alternatively, and as provided in another example, the wristband 108 may be configured to use the pulse oximeter to measure an amount of oxygen in the blood of the user (e.g., by sending infrared light into capillaries and measuring how much light is reflected off the gases). Sensor data (e.g., vital signs data) relating to the heart rate of the user and to the amount of oxygen in the user's blood may be provided to the health management server 3202.

As shown by reference number 3234, the goniometer 108 may provide a third set of sensor data to the health management server 3202. For example, the goniometer 108 may include a radial magnet and one or more processors with a magnetic sensing encoder chip capable of sensing a position of the radial magnet. The position of the magnet may be measured periodically and used to determine one or more angles of extension or bend. A third set of sensor data relating to the one or more angles of extension or bend may be provided to the health management server 3202.

In this way, sensor data related to determining the user's progress in the prehabilitation plan may be provided to the health management server 3202.

Figure 32F:
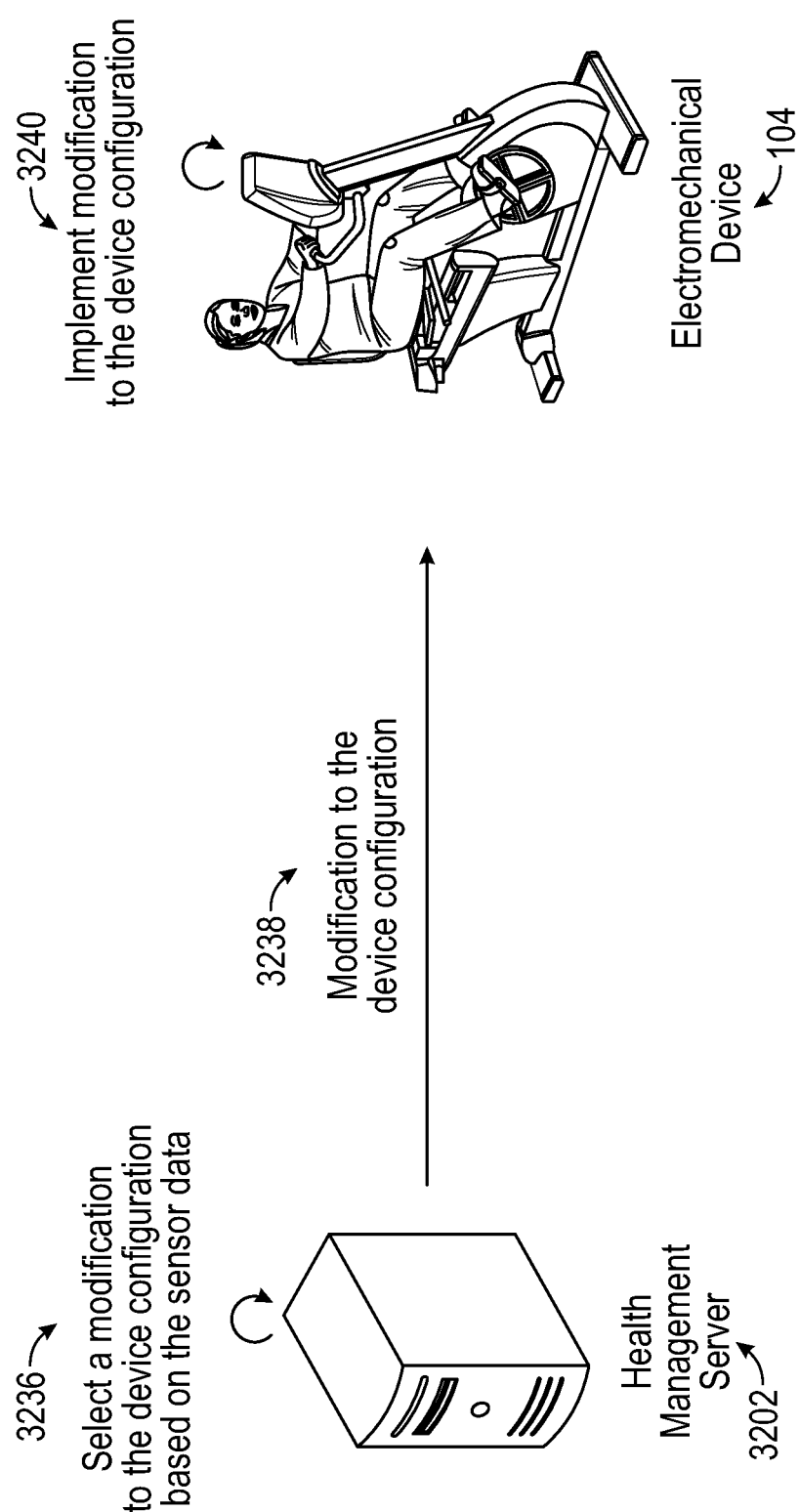

FIG. 32F generally illustrates the health management server 3202 performing one or more actions to optimize the exercise session of the user. Optimizing the exercise session may include modifying the device configuration to reduce a likelihood that the user is injured, to improve a rate at which the user strengthens an area of the body targeted for prehabilitation, and/or the like.

As shown by reference number 3236, the health management server 3202 may select a modification to the device configuration based on the sensor data. In some embodiments, the health management server 3202 may provide the sensor data as an input to the machine learning model such that the machine learning model is configured to output a set of machine learning scores. The set of machine learning scores may relate to (e.g., be stored in association with) a set of configuration values capable of being used to modify the device configuration. A machine learning score may represent a confidence that implementing a particular configuration value will optimize the exercise session for the user (relative to a current device configuration implementation, relative to implementing one or more other configuration values, etc.). For example, a scale of 1-100 may be implemented, where a value of one represents a low confidence that implementing a particular configuration value will optimize the exercise session for the user and a value of one hundred represents a high confidence that implementing the particular configuration value will optimize the exercise session for the user.

In some embodiments, the health management server 3202 may select, as the modification, a configuration value relating to a highest available machine learning score. In some embodiments, the health management server 3202 may select one or more configuration values based on one or more corresponding machine learning scores satisfying a threshold machine learning score. For example, the health management server 3202 may compare the set of machine learning scores and the threshold machine learning score and may determine that one or more machine learning scores satisfy the threshold machine learning score. In this case, the health management server 3202 may select, as the modification, one or more configuration values corresponding to the one or more machine learning scores.

As shown by reference number 3238, the health management server 3202 may provide the modification to the device configuration to the motor controller 120 of the electromechanical device 104. As shown by reference number 3240, the electromechanical device 104 may implement the modification to the device configuration. For example, the electromechanical device 104 may implement the modification by reading the one or more configuration values and adjusting the device configuration based on the one or more configuration values.

In this way, the health management server 3202 enables the electromechanical device 104 to implement the modification to the device configuration.

Figure 32G:
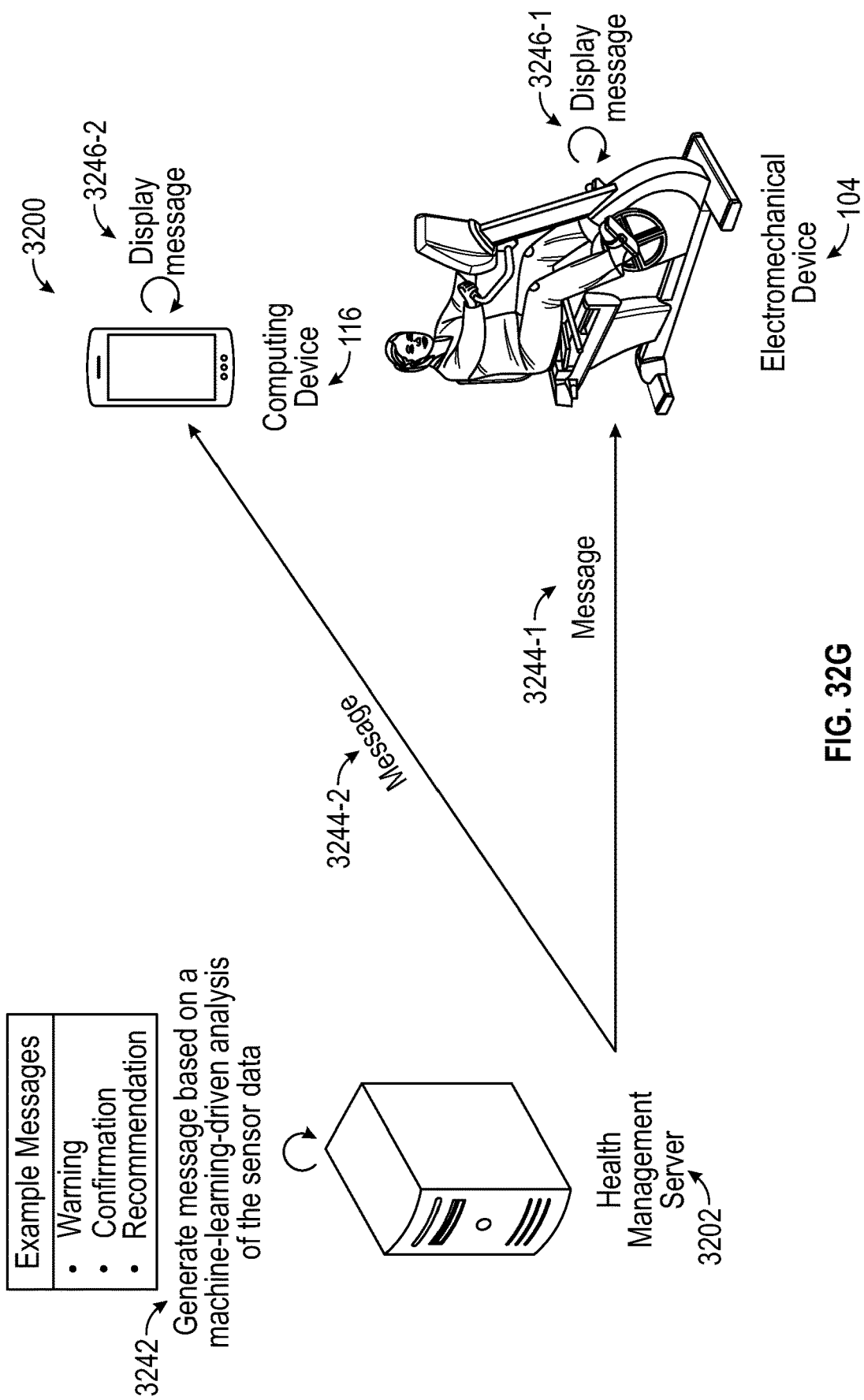

FIG. 32G generally illustrates the health management server 3202 generating and providing a message. As shown by reference number 3242, the health management server 3202 may generate a message (written, spoken, visually displayed, etc.) based on a machine-learning-driven analysis of the sensor data. For example, the health management server 3202 may provide the sensor data as an input to the machine learning model, such that the machine learning model is configured to output one or more risk scores that represent a probability of change to a health indicator of the user. The health management server 3202 may determine whether the one or more risk scores satisfy a threshold risk score and may generate the message for the user based on the one or more risk scores satisfying the threshold risk score.

The text of the message may include a warning message that the user is exercising in a manner that may increase a likelihood of injury or delaying the prehabilitation process, a confirmation message indicating that the user is exercising within an optimal ROM or at an optimal speed, a recommendation to modify the device configuration, a recommendation for the user to change form or posture while performing the exercise session, a recommendation for the user to change an amount of force exerted on one or more pedals 110 of the electromechanical device 104, and/or the like.

As shown by reference number 3244-1, the health management server 3202 may provide the message to the electromechanical device 104. For example, the health management server 3202 may provide the message for display via an interface associated with the electromechanical device 104. The interface may be an interface of the user portal 118, an interface of an exercise application running on the electromechanical device 104, and/or the like.

As shown by reference number 3244-2, the health management server 3202 may provide the message to one or more computing devices 116. For example, the health management server 3202 may provide the message to the computing device 116-1 that is accessible to the healthcare professional, to the computing device 116-2 that is accessible to the user, and/or the like.

As shown by reference number 3246-1, the electromechanical device 104 may display the message. For example, the message may be displayed such that the user is enabled to view the message while performing the exercise session. As shown by reference number 3246-2, the computing device 116 may display the message. For example, the message may be displayed on the computing device 116-1 associated with the healthcare professional and/or on the computing device 116-2 associated with the user.

One or more embodiments described herein may be implemented during a telemedicine or telehealth session with a healthcare professional. For example, the prehabilitation plans (and/or other prehabilitation plans not selected) may be presented, during a telemedicine or telehealth session, to a healthcare professional. The healthcare professional may select a particular prehabilitation plan for the user to cause that prehabilitation plan to be transmitted to the user and/or to control, based on the prehabilitation plan, the electromechanical device 104. In some embodiments, to facilitate telehealth or telemedicine applications, including remote diagnoses, determination of prehabilitation plans and rehabilitative and/or pharmacologic prescriptions, the health management server 3202 may receive and/or operate distally from the user and the electromechanical device 104. In such cases, the recommended prehabilitation plans and/or other health improvement plans may be presented simultaneously with a video of the user in real-time or near real-time during a telemedicine or telehealth session on a user interface of a computing device of a healthcare professional (e.g., computing device 116-1). The term "medical action(s)" may refer to any suitable action(s) performed by a healthcare professional, and such action or actions may include diagnoses, prescriptions for treatment plans, prescriptions for treatment devices, and the making, composing and/or executing of appointments, telemedicine sessions, prescriptions of medicines, telephone calls, emails, text messages, and the like.

By using machine learning to process received data, the health management server 3202 generates a prehabilitation plan that is optimal for the user. For example, the health management server 3202 may generate a prehabilitation plan that includes an exercise session, where the exercise session may be performed by the user when a device configuration is implemented on the electromechanical device 104. The device configuration allows the exercise session to be performed using an optimal ROM, performed at an optimal strength, performed at an optimal endurance, and/or the like. Additionally, by using machine learning to generate an optimal prehabilitation plan that accounts for a number of factors that influence optimality (e.g., user demographics, medical history, surgical results, and/or the like), the health management server 3202 reduces a likelihood of injury or re-injury and improves a speed at which the user can recover. This reduces a utilization of resources (e.g., power resources, processing resources, network resources, and/or the like) of the electromechanical device 104 and related devices relative to using an inferior plan more likely to injure or re-injure the user and that will require more time to recover.

Figure 33:
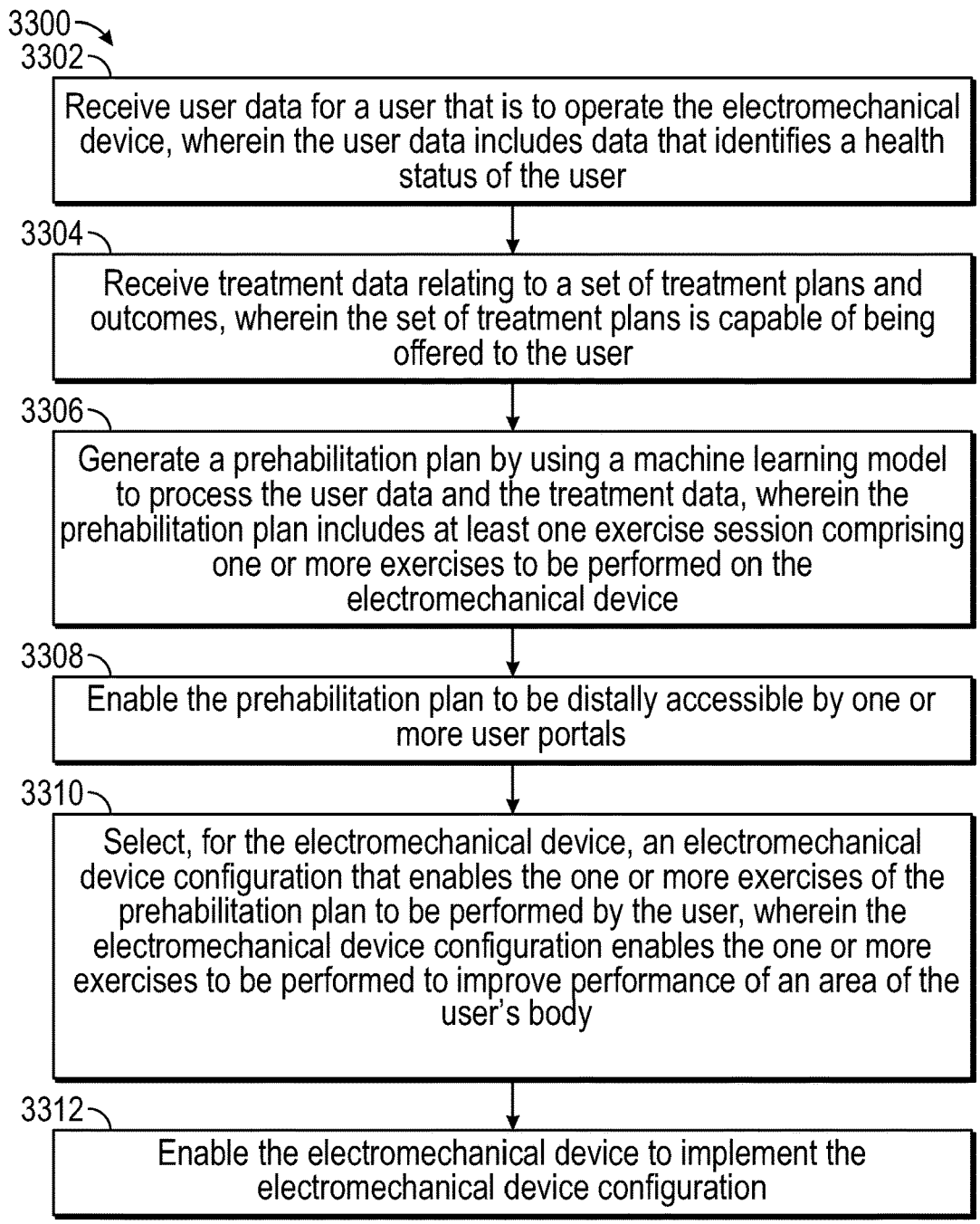
FIG. 33 generally illustrates a flowchart of an example method for using machine learning to generate a prehabilitation plan for a user and for enabling an electromechanical device to implement an electromechanical device configuration for an exercise session that is part of the prehabilitation plan.

FIG. 33 generally illustrates a flowchart of an example method 3300 for using machine learning to generate a prehabilitation plan for a user and for enabling the electromechanical device 104 to implement an electromechanical device configuration for an exercise session that is part of the prehabilitation plan. In some embodiments, the method 3300 is implemented on the health management server 3202 shown in FIGS. 32A-32G. In some embodiments, the health management server 3202 may be part of the cloud-based computing system 116. The method 3300 may include operations implemented in computer instructions stored in a memory and executed by a processor of the health management server 3202.

At block 3302, the method 3300 may include receiving user data for a user that is to operate the electromechanical device 104. For example, the health management server 3202 may receive user data that identifies a health status of a user that is to operate an electromechanical device 104.

At block 3304, the method 3300 may include receiving treatment data relating to a set of treatment plans and outcomes. For example, the health management server 3202 may receive treatment data relating to a set of treatment plans and outcomes that is capable of being offered to the user.

At block 3306, the method 3300 may include generating a prehabilitation plan by using a machine learning model to process the user data and the treatment data. For example, the health management server 3202 may generate a prehabilitation plan by using a machine learning model to process the user data and the treatment data, where the health improvement plan includes an exercise session to be performed on the electromechanical device 104.

At block 3308, the method 330 may include enabling the prehabilitation plan to be made distally accessible by one or more user portals. For example, the health management server 3202 may enable remote users to access the prehabilitation plan by providing the prehabilitation plan to one or more user portals, such as the user portal 118, the clinical portal 126, an administrative (admin) portal, a software developer portal, and/or the like.

At block 3310, the method 3300 may include selecting, for the electromechanical device 104, a device configuration that enables the one or more exercises of the prehabilitation plan to be performed by the user. For example, the health management server 3202 may select, for the electromechanical device 104, a device configuration that enables the one or more exercises of the prehabilitation plan to be performed by the user. This improves performance of an area of the user's body that would be affected if the health-related event occurs with respect to the user.

At block 3312, the method 3300 may include enabling the electromechanical device 104 to implement the electromechanical device configuration. For example, the health management server 3202 may enable the electromechanical device 104 to implement the electromechanical device 104 configuration by providing the electromechanical device configuration to the electromechanical device 104.

Figure 34:
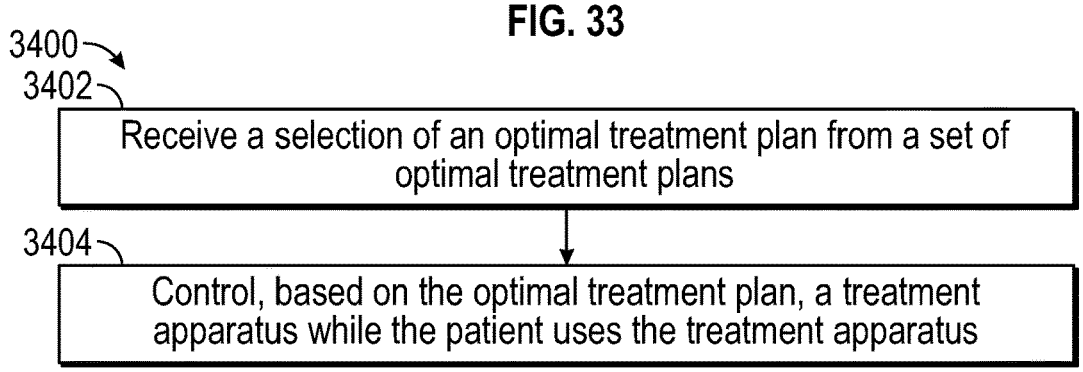
FIG. 34 shows an example embodiment of a method for receiving a selection of an optimal treatment plan and controlling, based on the optimal treatment plan, a treatment apparatus while the patient uses the treatment apparatus according to the present disclosure.

FIG. 34 shows an example embodiment of a method 3400 for receiving a selection of an optimal treatment plan and controlling, based on the optimal treatment plan, a treatment apparatus (e.g., the electromechanical device 104) while the patient uses the treatment apparatus according to the present disclosure. Method 3400 includes operations performed by processors of a computing device (e.g., any component of FIG. 1, such as server 128 executing the training engine 130). In some embodiments, one or more operations of the method 3400 are implemented in computer instructions stored on a memory device and executed by a processing device. The method 3400 may be performed in the same or a similar manner as described above in regard to method 3300. The operations of the method 3400 may be performed in some combination with any of the operations of any of the methods described herein.

Prior to the method 3400 being executed, various optimal treatment plans may be generated by one or more trained machine learning models 132 of the training engine 130. For example, based on a set of treatment plans pertaining to a medical condition of a patient, the one or more trained machine learning models 132 may generate the optimal treatment plans. The various treatment plans may be transmitted to one or computing devices of a patient and/or healthcare professional.

At block 3402 of the method 3400, the processing device may receive a selection of an optimal treatment plan from the optimal treatment plans. The selection may have been entered on a user interface presenting the optimal treatment plans on the patient interface and/or the assistant interface.

At block 3404, the processing device may control, based on the selected optimal treatment plan, the treatment apparatus while the patient uses the treatment apparatus. In some embodiments, the controlling is performed distally by the server 128. If the selection is made using a patient interface, one or more control signals may be transmitted from the patient interface to the treatment apparatus to configure, according to the selected treatment plan, a setting of the treatment apparatus to control operation of the treatment apparatus. Further, if the selection is made using an assistant interface, one or more control signals may be transmitted from the assistant interface to the treatment apparatus to configure, according to the selected treatment plan, a setting of the treatment apparatus to control operation of the treatment apparatus.

It should be noted, that as the patient uses the treatment apparatus, sensors may transmit measurement data to a processing device. The processing device may dynamically control, according to the treatment plan, the treatment apparatus by modifying, based on the sensor measurements, a setting of the treatment apparatus. For example, if the force measured by the sensors indicates the user is not applying enough force to a pedal, the treatment plan may indicate to reduce the required amount of force for an exercise.

It should be noted, that as the patient uses the treatment apparatus, the user may use the patient interface to enter input pertaining to a pain level experienced by the patient as the patient performs the treatment plan. For example, the user may enter a high degree of pain while pedaling with the pedals 110 set to a certain range of motion on the treatment apparatus. The pain level may cause the range of motion to be dynamically adjusted based on the treatment plan. For example, the treatment plan may specify alternative range of motion settings if a certain pain level is indicated when the user is performing an exercise at a certain range of motion.

Clause 1. A computer-implemented system, comprising: an electromechanical device configured to be manipulated by a user while the user performs a prehabilitation procedure; a user portal comprising an output device and an input device, the output device configured to communicate a prehabilitation plan to the user, wherein the prehabilitation plan includes at least one exercise session comprising one or more exercises to be performed on the electromechanical device; and a computing device configured to: receive user data relating to the user, wherein the user data comprises health history data relating to health indicators of the user, receive treatment data relating to a set of treatment plans and outcomes, wherein the set of treatment plans is capable of being offered to the user, generate the prehabilitation plan by using a machine learning model to process the user data and the treatment data, select, for the electromechanical device, an electromechanical device configuration that enables the one or more exercises of the prehabilitation plan to be performed by the user, wherein the electromechanical device configuration enables the one or more exercises to be performed to improve performance of an area of the user's body, and enable the electromechanical device to implement the electromechanical device configuration by providing the electromechanical device configuration to the electromechanical device.

Clause 2. The computer-implemented system of any clause herein, wherein the treatment data comprises treatment plan data relating to the set of treatment plans and treatment outcome data relating to outcomes of the set of treatment plans.

Clause 3. The computer-implemented system of any clause herein, wherein the computing device, when generating the prehabilitation plan, is configured to: provide the user data and the treatment data as inputs to the machine learning model such that the machine learning model is configured to generate machine learning scores for electromechanical device configurations capable of being selected for the prehabilitation plan, wherein the machine learning scores relate to probabilities of a given device configuration being suitable for a given application or applications for the user.

Clause 4. The computer-implemented system of any clause herein, wherein, based on the selected device configuration corresponding to a threshold probability of improving the performance of the area of the user's body, the selected electromechanical device is suitable for the given user application or applications.

Clause 5. The computer-implemented system of any clause herein, wherein, based on the selected device configuration corresponding to a threshold probability of preventing a health-related event from occurring that affects the area of the user's body, the selected electromechanical device configuration is suitable for the given application or applications for the user.

Clause 6. The computer-implemented system of any clause herein, wherein the electromechanical device configuration is configured such that the user, when performing the one or more exercises on the electromechanical device, is enabled to repeat one or more motions associated with at least one of developing muscle memory or improving muscle memory.

Clause 7. The computer-implement system of any clause herein, wherein the one or more exercises are one or more rehabilitation exercises, wherein the electromechanical device configuration comprises data related to one or more positions at which to configure one or more components of the electromechanical device, and wherein the one or more positions are configured such that the one or more rehabilitation exercises are performed by the user prior to a health-related event occurring that affects the area of the user's body.

Clause 8. A method for using machine learning to control an electromechanical device, comprising: receiving user data relating to a user capable of operating the electromechanical device as part of a prehabilitation procedure, wherein the user data comprises health history data relating to one or more health indicators of the user; receiving treatment data relating to a set of treatment plans and outcomes, wherein the set of treatment plans is capable of being offered to the user; generating a prehabilitation plan by using a machine learning model to process the user data and the treatment data, wherein the prehabilitation plan includes at least one exercise session comprising one or more exercises to be performed on the electromechanical device; enabling the prehabilitation plan to be distally accessible by one or more user portals; selecting, for the electromechanical device, an electromechanical device configuration that enables the one or more exercises of the prehabilitation plan to be performed by the user, wherein the electromechanical device configuration enables the one or more exercises to be performed to improve performance of an area of the user's body; and enabling the electromechanical device to implement the electromechanical device configuration by providing the electromechanical device configuration to the electromechanical device.

Clause 9. The method of any clause herein, wherein the treatment data comprises treatment plan data relating to the set of treatment plans and treatment outcome data relating to outcomes of the set of treatment plans.

Clause 10. The method of any clause herein, wherein generating the prehabilitation plan comprises: providing the user data and the treatment data as inputs to the machine learning model such that the machine learning model is configured to generate machine learning scores for electromechanical device configurations capable of being selected for the prehabilitation plan, wherein the machine learning scores relate to probabilities of a given device configuration being suitable for a given application or applications for the user.

Clause 11. The method of any clause herein, wherein, based on the selected device configuration corresponding to a threshold probability of improving the performance of the area of the user's body, the electromechanical device configuration that has been selected is suitable for the given application or applications for the user.

Clause 12. The method of any clause herein, wherein, based on the selected device configuration corresponding to a threshold probability of preventing a health-related event from occurring that affects the area of the user's body, the electromechanical device configuration that has been selected is suitable for the given application or applications for the user.

Clause 13. The method of any clause herein, wherein the electromechanical device configuration is configured such that the user, when performing the one or more exercises on the electromechanical device, is enabled to repeat one or more motions that develop muscle memory.

Clause 14. The method of any clause herein, wherein the one or more exercises are one or more rehabilitation exercises; wherein the electromechanical device configuration comprises data related to one or more positions at which to configure one or more components of the electromechanical device, and wherein the one or more positions are configured such that the one or more rehabilitation exercises are performed by the user prior to a health-related event occurring that affects the arear of the user's body.

Clause 15. The method of any clause herein, wherein the one or more exercises relate to one or more rehabilitation exercises; wherein the electromechanical device configuration comprises data related to one or more forces to apply to one or more components of the electromechanical device, and wherein said one or more forces, when applied to the one or more components of the electromechanical device, are to be applied by a motor of the electromechanical device as part of a rehabilitation exercise that is one of the one or more rehabilitation exercises.

Clause 16. The method of any clause herein, wherein the electromechanical device configuration is configured such that the one or more exercises, when performed by the user on the electromechanical device, enable the user to improve at least one of ROM, strength, and endurance.

Clause 17. The method of any clause herein, further comprising distally controlling, while the user is performing the one or more exercises, the electromechanical device based on the prehabilitation plan.

Clause 18. The method of any clause herein, further comprising: receiving sensor data comprising one or more data values related to determining the user's progress in the prehabilitation plan; and controlling, while the user is performing the one or more exercises, the electromechanical device based on the sensor data.

Clause 19. The method of any clause herein, further comprising: receiving sensor data comprising one or more data values related to determining the user's progress in the prehabilitation plan; providing the sensor data as an input to the machine learning model such that the machine learning model is configured to output a set of machine learning scores, wherein the set of machine learning scores relates to a set of configuration values capable of being used to modify the electromechanical device configuration; selecting one or more configuration values, from the set of configuration values, based on the one or more configuration values relating to a machine learning score that satisfies a threshold machine learning score; and providing, to the electromechanical device, a modification comprising the one or more configuration values, such that the electromechanical device is enabled to implement the modification.

Clause 19. The method of any clause herein, wherein providing the modification to the electromechanical device comprises: providing the modification to the electromechanical device such that the electromechanical device is enabled to implement the modification to compensate for a difference between a ROM applied by the user and an optimal ROM for the user.

Clause 20. The method of any clause herein, wherein providing the modification to the electromechanical device comprises: providing the modification to the electromechanical device such that the modification compensates for a difference between a force the user applied to one or more components of the electromechanical device and an optimal force the user is to apply to the one or more components.

Clause 21. The method of any clause herein, wherein providing the modification to the electromechanical device comprises: providing the modification to the electromechanical device such that the modification enables a motor of the electromechanical device to control one or more rotations of one or more components of the electromechanical device.

Clause 22. The method of any clause herein, further comprising: receiving sensor data comprising one or more data values related to determining the user's progress in the prehabilitation plan; providing the sensor data as an input to the machine learning model such that the machine learning model is configured to output one or more risk scores, wherein each of the one or more risk scores represents a probability of a health-related event occurring that affects the area of the user's body; determining that at least one of the one or more risk scores satisfy a threshold risk score; and responsive to determining that at least one of the one or more risk scores satisfy a corresponding threshold risk score, performing one or more actions to reduce or eliminate a probability of the health-related event from occurring to the user.

Clause 23. The method of any clause herein, wherein the exercise session is a prehabilitation exercise session, and wherein the method further comprises: receiving sensor data comprising one or more data values related to the user's progress in the prehabilitation plan; receiving medical procedure data relating to an updated health indicator that comprises the one or more health indicators of the user; providing the user data, the sensor data, and the medical procedure data as inputs to the machine learning model such that the machine learning model is configured to output a set of machine learning scores, wherein the set of machine learning scores relates to a set of configuration values capable of being used in a device configuration for a rehabilitation plan; selecting one or more configuration values, from the set of configuration values, based on the one or more configuration values relating to one or more machine learning scores that satisfy a threshold machine learning score; and providing the one or more configuration values to the electromechanical device, wherein the one or more configuration values are part of the electromechanical device configuration for the rehabilitation plan, and wherein said one or more configuration values are provided to the electromechanical device such that the electromechanical device is enabled to implement the electromechanical device configuration for the rehabilitation plan.

Clause 24. A system, comprising: a memory device storing instructions; and a processing device communicatively coupled to the memory device, wherein the processing device, when executing the instructions, is to: receive user data relating to a user capable of operating the electromechanical device as part of a prehabilitation procedure, wherein the user data comprises health history data relating to one or more health indicators of the user; receive treatment data relating to a set of treatment plans and outcomes, wherein the set of treatment plans is capable of being offered to the user; generate a prehabilitation plan by using a machine learning model to process the user data and the treatment data, wherein the prehabilitation plan includes at least one exercise session comprising one or more exercises to be performed on the electromechanical device; enable the prehabilitation plan to be distally accessible by one or more user portals; select, for the electromechanical device, an electromechanical device configuration that enables the one or more exercises of the prehabilitation plan to be performed by the user, wherein the electromechanical device configuration enables the one or more exercises to be performed to improve performance of an area of the user's body; and enable the electromechanical device to implement the electromechanical device configuration by providing the electromechanical device configuration to the electromechanical device.

Clause 25. The system of any clause herein, wherein the treatment data comprises treatment plan data relating to the set of treatment plans and treatment outcome data relating to outcomes of the set of treatment plans.

Clause 26. The system of any clause herein, wherein the processing device, when generating the prehabilitation plan, is configured to: provide the user data and the treatment data as inputs to the machine learning model such that the machine learning model is configured to generate machine learning scores for electromechanical device configurations capable of being selected for the prehabilitation plan, wherein the machine learning scores relate to probabilities of a given device configuration being suitable for a given application or applications for the user.

Clause 27. The system of any clause herein, wherein, based on the selected device configuration corresponding to a threshold probability of improving the performance of the area of the user's body, the electromechanical device configuration that has been selected is suitable for the given application or applications for the user.

Clause 28. The system of any clause herein, wherein, based on the selected device configuration corresponding to a threshold probability of preventing a health-related event from occurring that affects the area of the user's body, the electromechanical device configuration that has been selected is suitable for the given application or applications for the user.

Clause 29. The system of any clause herein, wherein the electromechanical device configuration is configured such that the user, when performing the one or more exercises on the electromechanical device, is enabled to repeat one or more motions that develop muscle memory.

Clause 30. The system of any clause herein, wherein the one or more exercises are one or more rehabilitation exercises; wherein the electromechanical device configuration comprises data related to one or more positions at which to configure one or more components of the electromechanical device, and wherein the one or more positions are configured such that the one or more rehabilitation exercises are performed by the user prior to a health-related event occurring that affects the area of the user's body.

Clause 31. The system of any clause herein, wherein the one or more exercises relate to one or more rehabilitation exercises; wherein the electromechanical device configuration comprises data related to one or more forces to apply to one or more components of the electromechanical device, and wherein said one or more forces, when applied to the one or more components of the electromechanical device, are to be applied by a motor of the electromechanical device as part of a rehabilitation exercise that is one of the one or more rehabilitation exercises.

Clause 32. The system of any clause herein, wherein the electromechanical device configuration is configured such that the one or more exercises, when performed by the user on the electromechanical device, enable the user to improve at least one of ROM, strength, and endurance.

Clause 33. The system of any clause herein, wherein the processing device is further configured to distally control, while the user is performing the one or more exercises, the electromechanical device based on the prehabilitation plan.

Clause 34. The system of any clause herein, wherein the processing device is further configured to: receive sensor data comprising one or more data values related to determining the user's progress in the prehabilitation plan; and control, while the user is performing the one or more exercises, the electromechanical device based on the sensor data.

Clause 35. The method of any clause herein, wherein the processing device is further configured to: receive sensor data comprising one or more data values related to determining the user's progress in the prehabilitation plan; provide the sensor data as an input to the machine learning model such that the machine learning model is configured to output a set of machine learning scores, wherein the set of machine learning scores relates to a set of configuration values capable of being used to modify the electromechanical device configuration; select one or more configuration values, from the set of configuration values, based on the one or more configuration values relating to a machine learning score that satisfies a threshold machine learning score; and provide, to the electromechanical device, a modification comprising the one or more configuration values, such that the electromechanical device is enabled to implement the modification.

Clause 36. The system of any clause herein, wherein the processing device, when providing the modification to the electromechanical device, is configured to: provide the modification to the electromechanical device such that the electromechanical device is enabled to implement the modification to compensate for a difference between a ROM applied by the user and an optimal ROM for the user.

Clause 37. The system of any clause herein, wherein the processing device, when providing the modification to the electromechanical device, is configured to: provide the modification to the electromechanical device such that the modification compensates for a difference between a force the user applied to one or more components of the electromechanical device and an optimal force the user is to apply to the one or more components.

Clause 38. The method of any clause herein, wherein the processing device, when providing the modification to the electromechanical device, is configured to: provide the modification to the electromechanical device such that the modification enables a motor of the electromechanical device to control one or more rotations of one or more components of the electromechanical device.

Clause 39. The system of any clause herein, wherein the processing device is further configured to: receive sensor data comprising one or more data values related to determining the user's progress in the prehabilitation plan; provide the sensor data as an input to the machine learning model such that the machine learning model is configured to output one or more risk scores, wherein each of the one or more risk scores represents a probability of a health-related event occurring that affects the area of the user's body; determine that at least one of the one or more risk scores satisfy a threshold risk score; and responsive to determining that at least one of the one or more risk scores satisfy a corresponding threshold risk score, perform one or more actions to reduce or eliminate a probability of the health-related event from occurring to the user.

Clause 40. The system of any clause herein, wherein the exercise session is a prehabilitation exercise session, and wherein the processing device is further configured to: receive sensor data comprising one or more data values related to the user's progress in the prehabilitation plan; receive medical procedure data relating to an updated health indicator that comprises the one or more health indicators of the user; providing the user data, the sensor data, and the medical procedure data as inputs to the machine learning model such that the machine learning model is configured to output a set of machine learning scores, wherein the set of machine learning scores relates to a set of configuration values capable of being used in a device configuration for a rehabilitation plan; select one or more configuration values, from the set of configuration values, based on the one or more configuration values relating to one or more machine learning scores that satisfy a threshold machine learning score; and provide the one or more configuration values to the electromechanical device, wherein the one or more configuration values are part of the electromechanical device configuration for the rehabilitation plan, and wherein said one or more configuration values are provided to the electromechanical device such that the electromechanical device is enabled to implement the electromechanical device configuration for the rehabilitation plan.

Clause 41. The system of any clause herein, wherein the processing device is further to: receive sensor data comprising one or more values related to determining the user's progress in the prehabilitation plan; and provide the sensor data to a clinical portal that is one of the one or more user portals, such that a healthcare professional is enabled to remotely monitor the user.

Clause 42. The system of any clause herein, wherein the processing device is further to: receive sensor data comprising one or more data values related to the user's progress in the prehabilitation plan; receive medical procedure data relating to an updated health indicator that comprises the one or more health indicators of the user; provide the user data, the sensor data, and the medical procedure data as inputs to the machine learning model such that the machine learning model is configured to output a set of machine learning scores, wherein the set of machine learning scores relates to a set of configuration values capable of being used in a device configuration for a rehabilitation plan; select one or more configuration values, from the set of configuration values, based on the one or more configuration values relating to one or more machine learning scores that satisfy a threshold machine learning score; and provide the one or more configuration values to the electromechanical device, wherein the one or more configuration values are part of the electromechanical device configuration for the rehabilitation plan, and wherein said one or more configuration values are provided to the electromechanical device such that the electromechanical device is enabled to implement the electromechanical device configuration for the rehabilitation plan.

Clause 43. A tangible, non-transitory computer-readable medium storing instructions that, when executed by a processing device, cause the processing device to: receive user data relating to a user capable of operating the electromechanical device as part of a prehabilitation procedure, wherein the user data comprises health history data relating to one or more health indicators of the user; receive treatment data relating to a set of treatment plans and outcomes, wherein the set of treatment plans is capable of being offered to the user; generate a prehabilitation plan by using a machine learning model to process the user data and the treatment data, wherein the prehabilitation plan includes at least one exercise session comprising one or more exercises to be performed on the electromechanical device; enable the prehabilitation plan to be distally accessible by one or more user portals; select, for the electromechanical device, an electromechanical device configuration that enables the one or more exercises of the prehabilitation plan to be performed by the user, wherein the electromechanical device configuration enables the one or more exercises to be performed to improve performance of an area of the user's body; and enable the electromechanical device to implement the electromechanical device configuration by providing the electromechanical device configuration to the electromechanical device.

Clause 44. The system of any clause herein, wherein the treatment data comprises treatment plan data relating to the set of treatment plans and treatment outcome data relating to outcomes of the set of treatment plans.

Clause 45. The tangible, non-transitory computer-readable medium of any clause herein, wherein the processing device, when generating the prehabilitation plan, is configured to: provide the user data and the treatment data as inputs to the machine learning model such that the machine learning model is configured to generate machine learning scores for electromechanical device configurations capable of being selected for the prehabilitation plan, wherein the machine learning scores relate to probabilities of a given device configuration being suitable for a given application or applications for the user.

Clause 46. The tangible, non-transitory computer-readable medium of any clause herein, wherein, based on the selected device configuration corresponding to a threshold probability of improving the performance of the area of the user's body, the electromechanical device configuration that has been selected is suitable for the given application or applications for the user.

Clause 47. The tangible, non-transitory computer-readable medium of any clause herein, wherein, based on the selected device configuration corresponding to a threshold probability of preventing a health-related event from occurring that affects the area of the user's body, the electromechanical device configuration that has been selected is suitable for the given application or applications for the user.

Clause 48. The tangible, non-transitory computer-readable medium of any clause herein, wherein the electromechanical device configuration is configured such that the user, when performing the one or more exercises on the electromechanical device, is enabled to repeat one or more motions that develop muscle memory.

Clause 49. The tangible, non-transitory computer-readable medium of any clause herein, wherein the one or more exercises are one or more rehabilitation exercises; wherein the electromechanical device configuration comprises data related to one or more positions at which to configure one or more components of the electromechanical device, and wherein the one or more positions are configured such that the one or more rehabilitation exercises are performed by the user prior to the health-related event occurring with respect to the user.

Clause 50. The tangible, non-transitory computer-readable medium of any clause herein, wherein the one or more exercises relate to one or more rehabilitation exercises; wherein the electromechanical device configuration comprises data related to one or more forces to apply to one or more components of the electromechanical device, and wherein said one or more forces, when applied to the one or more components of the electromechanical device, are to be applied by a motor of the electromechanical device as part of a rehabilitation exercise that is one of the one or more rehabilitation exercises.

Clause 51. The tangible, non-transitory computer-readable medium of any clause herein, wherein the electromechanical device configuration is configured such that the one or more exercises, when performed by the user on the electromechanical device, enable the user to improve at least one of ROM, strength, and endurance.

Clause 52. The tangible, non-transitory computer-readable medium of any clause herein, wherein the instructions, when executed by the processing device, further cause the processing device to distally control, while the user is performing the one or more exercises, the electromechanical device based on the prehabilitation plan.

Clause 53. The tangible, non-transitory computer-readable medium of any clause herein, wherein the instructions, when executed by the processing device, further cause the processing device to: receive sensor data comprising one or more data values related to determining the user's progress in the prehabilitation plan; and control, while the user is performing the one or more exercises, the electromechanical device based on the sensor data.

Clause 54. The tangible, non-transitory computer-readable medium of any clause herein, wherein the instructions, when executed by the processing device, further cause the processing device to: receive sensor data comprising one or more data values related to determining the user's progress in the prehabilitation plan; provide the sensor data as an input to the machine learning model such that the machine learning model is configured to output a set of machine learning scores, wherein the set of machine learning scores relates to a set of configuration values capable of being used to modify the electromechanical device configuration; select one or more configuration values, from the set of configuration values, based on the one or more configuration values relating to a machine learning score that satisfies a threshold machine learning score; and provide, to the electromechanical device, a modification comprising the one or more configuration values, such that the electromechanical device is enabled to implement the modification.

Clause 55. The tangible, non-transitory computer-readable medium of any clause herein, wherein the machine learning model is trained on historical data comprising safety data related to a set of constraints approved by a healthcare professional; and wherein the instructions, that cause the processing device to provide the modification to the electromechanical device, cause the processing device to: provide the modification to the electromechanical device such that the electromechanical device is enabled to implement the modification to compensate for a difference between a ROM applied by the user and an optimal ROM for the user.

Clause 56. The tangible, non-transitory computer-readable medium of any clause herein, wherein the instructions, that cause the processing device to provide the modification to the electromechanical device, cause the electromechanical device to: provide the modification to the electromechanical device such that the modification compensates for a difference between a force the user applied to one or more components of the electromechanical device and an optimal force the user is to apply to the one or more components.

Clause 57. The tangible, non-transitory computer-readable medium of any clause herein, wherein the instructions, that cause the processing device to provide the modification to the electromechanical device, cause the processing device to: provide the modification to the electromechanical device such that the modification enables a motor of the electromechanical device to control one or more rotations of one or more components of the electromechanical device.

Clause 58. The tangible, non-transitory computer-readable medium of any clause herein, wherein the instructions, that cause the processing device to provide the device configuration to the electromechanical device, cause the processing device to: receive sensor data comprising one or more data values related to determining the user's progress in the prehabilitation plan; provide the sensor data as an input to the machine learning model such that the machine learning model is configured to output one or more risk scores, wherein each of the one or more risk scores represents a probability of a health-related event occurring that affects the area of the user's body; determine that at least one of the one or more risk scores satisfy a threshold risk score; and responsive to determining that at least one of the one or more risk scores satisfy a corresponding threshold risk score, perform one or more actions to reduce or eliminate a probability of the health-related event from occurring to the user.

Clause 59. The tangible, non-transitory computer-readable medium of any clause herein, wherein the exercise session is a prehabilitation exercise session, and wherein the instructions, when executed by the processing device, further cause the processing device to: receive sensor data comprising one or more data values related to the user's progress in the prehabilitation plan; receive medical procedure data relating to an updated health indicator that comprises the one or more health indicators of the user; provide the user data, the sensor data, and the medical procedure data as inputs to the machine learning model such that the machine learning model is configured to output a set of machine learning scores, wherein the set of machine learning scores relates to a set of configuration values capable of being used in a device configuration for a rehabilitation plan; select one or more configuration values, from the set of configuration values, based on the one or more configuration values relating to one or more machine learning scores that satisfy a threshold machine learning score; and provide the one or more configuration values to the electromechanical device, wherein the one or more configuration values are part of the electromechanical device configuration for the rehabilitation plan, and wherein said one or more configuration values are provided to the electromechanical device such that the electromechanical device is enabled to implement the electromechanical device configuration for the rehabilitation plan.

What is claimed is:

1. A computer-implemented system, comprising:
an electromechanical device configured to be manipulated by a user while the user performs a prehabilitation procedure;
a user portal comprising an output device and input device, the output device configured to communicate a prehabilitation plan to the user, wherein the prehabilitation plan includes at least one exercise session comprising one or more exercises to be performed on the electromechanical device; and
a computing device configured to:
receive user data relating to the user, wherein the user data comprises health history data relating to health indicators of the user,
receive treatment data relating to a set of treatment plans and outcomes, wherein the set of treatment plans is capable of being offered to the user,
generate the prehabilitation plan by using a machine learning model to process the user data and the treatment data,
select, for the electromechanical device, an electromechanical device configuration that enables the one or more exercises of the prehabilitation plan to be performed by the user, wherein the electromechanical device configuration enables the one or more exercises to be performed to improve performance of an area of the user's body, and
enable the electromechanical device to implement the electromechanical device configuration by providing the electromechanical device configuration to the electromechanical device.

2. The computer-implemented system of claim 1, wherein the treatment data comprises treatment plan data relating to the set of treatment plans and treatment outcome data relating to outcomes of the set of treatment plans.

3. The computer-implemented system of claim 1, wherein the computing device, when generating the prehabilitation plan, is configured to:
provide the user data and the treatment data as inputs to the machine learning model such that the machine learning model is configured to generate machine learning scores for electromechanical device configurations capable of being selected for the prehabilitation plan, wherein the machine learning scores relate to probabilities of a given device configuration being suitable for a given application or applications for the user.

4. The computer-implemented system of claim 3, wherein, based on the selected device configuration corresponding to a threshold probability of improving the performance of the area of the user's body, the selected electromechanical device is suitable for the given user application or applications.

5. The computer-implemented system of claim 3, wherein, based on the selected device configuration corresponding to a threshold probability of preventing a health-related event from occurring that affects the area of the user's body, the selected electromechanical device configuration is suitable for the given application or applications for the user.

6. The computer-implemented system of claim 1, wherein the electromechanical device configuration is configured such that the user, when performing the one or more exercises on the electromechanical device, is enabled to repeat one or more motions associated with at least one of developing muscle memory or improving muscle memory.

7. The computer-implemented system of claim 1, wherein the one or more exercises are one or more rehabilitation exercises, wherein the electromechanical device configuration comprises data related to one or more positions at which to configure one or more components of the electromechanical device, and wherein the one or more positions are configured such that the one or more rehabilitation exercises are performed by the user prior to a health-related event occurring that affects the area of the user's body.

8. A method for using machine learning to control an electromechanical device, comprising:
receiving user data relating to a user capable of operating the electromechanical device as part of a prehabilitation procedure, wherein the user data comprises health history data relating to health indicators of the user;
receiving treatment data relating to a set of treatment plans and outcomes, wherein the set of treatment plans is capable of being offered to the user;

generating a prehabilitation plan by using a machine learning model to process the user data and the treatment data, wherein the prehabilitation plan includes at least one exercise session comprising one or more exercises to be performed on the electromechanical device;

enabling the prehabilitation plan to be distally accessible by one or more user portals;

selecting, for the electromechanical device, an electromechanical device configuration that enables the one or more exercises of the prehabilitation plan to be performed by the user, wherein the electromechanical device configuration enables the one or more exercises to be performed to improve performance of an area of the user's body; and enabling the electromechanical device to implement the electromechanical device configuration by providing the electromechanical device configuration to the electromechanical device.

9. The method of claim 8, wherein the treatment data comprises treatment plan data relating to the set of treatment plans and treatment outcome data relating to outcomes of the set of treatment plans.

10. The method of claim 8, wherein generating the prehabilitation plan comprises:

providing the user data and the treatment data as inputs to the machine learning model such that the machine learning model is configured to generate machine learning scores for electromechanical device configurations capable of being selected for the prehabilitation plan, wherein the machine learning scores relate to probabilities of a given device configuration being suitable for a given application or applications for the user.

11. The method of claim 10, wherein the selected electromechanical device is suitable for the given user application or applications based on the selected device configuration corresponding to a threshold probability of improving performance of the area of the user's body.

12. The method of claim 10, wherein the selected electromechanical device configuration is suitable for the given application or applications for the user based on the selected device configuration corresponding to a threshold probability of preventing a health-related event from occurring that affects the area of the user's body.

13. The method of claim 8, wherein the electromechanical device configuration is configured such that the user, when performing the one or more exercises on the electromechanical device, is enabled to repeat one or more motions associated with at least one of developing muscle memory or improving muscle memory.

14. The method of claim 8, wherein the one or more exercises are one or more rehabilitation exercises, wherein the electromechanical device configuration comprises data related to one or more positions at which to configure one or more components of the electromechanical device, and wherein the one or more positions are configured such that the one or more rehabilitation exercises are performed by the user prior to a health-related event occurring that affects that area of the user's body.

15. The method of claim 8, wherein the one or more exercises relate to one or more rehabilitation exercises; wherein the electromechanical device configuration comprises data related to one or more forces to apply to one or more components of the electromechanical device, and wherein said one or more forces, when applied to the one or more components of the electromechanical device, are capable of being applied by a motor of the electromechanical device as part of a rehabilitation exercise that is one of the one or more rehabilitation exercises.

16. A system for operating an electromechanical device, comprising:

a memory device storing instructions; and a processing device communicatively coupled to the memory device, wherein the processing device, when executing the instructions, is configured to:

receive user data relating to a user capable of operating the electromechanical device as part of a prehabilitation procedure, wherein the user data comprises health history data relating to health indicators of the user;

receive treatment data relating to a set of treatment plans and outcomes, wherein the set of treatment plans is capable of being offered to the user;

generate a prehabilitation plan by using a machine learning model to process the user data and the treatment data, wherein the prehabilitation plan includes at least one exercise session comprising one or more exercises to be performed on the electromechanical device;

enable the prehabilitation plan to be distally accessible by one or more user portals;

select, for the electromechanical device, an electromechanical device configuration that enables the one or more exercises of the prehabilitation plan to be performed by the user, wherein the electromechanical device configuration enables the one or more exercises to be performed to improve performance of an area of the user's body; and enable the electromechanical device to implement the electromechanical device configuration by providing the electromechanical device configuration to the electromechanical device.

17. The system of claim 16, wherein the processing device is further configured such that the one or more exercises, when performed by the user on the electromechanical device, enable the user to improve at least one of ROM, strength, and endurance.

18. The system of claim 16, wherein the processing device is further configured to further distally control, while the user is performing the one or more exercises, the electromechanical device based on the prehabilitation plan.

19. The system of claim 16, wherein the processing device is further configured to:

receive sensor data comprising one or more data values related to determining the user's progress in the prehabilitation plan; and control, while the user is performing the one or more exercises, the electromechanical device based on the sensor data.

20. The system of claim 16, wherein the processing device is further configured to:

receive sensor data comprising one or more data values related to determining the user's progress in the prehabilitation plan;

provide the sensor data as an input to the machine learning model such that the machine learning model is configured to output a set of machine learning scores, wherein the set of machine learning scores relates to a set of configuration values capable of being used to modify the electromechanical device configuration;

select one or more configuration values, from the set of configuration values, based on the one or more configuration values relating to a machine learning score that satisfies a threshold machine learning score; and provide, to the electromechanical device, a modification comprising the one or more configuration values, such that the electromechanical device is enabled to implement the modification.

21. The system of claim 20, wherein the processing device, when providing the modification to the electromechanical device, is configured to:
provide the modification to the electromechanical device such that the electromechanical device is enabled to implement the modification to partially or wholly compensate for a difference between a ROM applied by the user and an optimal ROM for the user.

22. The system of claim 20, wherein the processing device, when providing the modification to the electromechanical device, is configured to:
provide the modification to the electromechanical device such that the modification compensates for a difference between a force the user applied to one or more components of the electromechanical device and an optimal force the user is to apply to the one or more components.

23. The system of claim 20, wherein the processing device, when providing the modification to the electromechanical device, is configured to:
provide the modification to the electromechanical device such that the modification enables a motor of the electromechanical device to control one or more rotations of one or more components of the electromechanical device.

24. The system of claim 16, wherein the processing device is further configured to:
receive sensor data comprising one or more data values related to determining the user's progress in the prehabilitation plan;
provide the sensor data as an input to the machine learning model such that the machine learning model is configured to output one or more risk scores, wherein each of the one or more risk scores represents a probability of a health-related event occurring that affects the area of the user's body;
determine that at least one of the one or more risk scores satisfy a threshold risk score; and
responsive to determining that at least one of the one or more risk scores satisfy a corresponding threshold risk score, performing one or more actions to reduce or eliminate the probability of the health-related event from occurring to the user.

25. The system of claim 16, wherein the exercise session is a prehabilitation exercise session, and wherein the processing device is further configured to:
receive sensor data comprising one or more data values related to the user's progress in the prehabilitation plan;
receive medical procedure data relating to an updated health indicator that comprises the one or more health indicators of the user;
provide the user data, the sensor data, and the medical procedure data as inputs to the machine learning model such that the machine learning model is configured to output a set of machine learning scores, wherein the set of machine learning scores relates to a set of configuration values capable of being used in a device configuration for a rehabilitation plan;
select one or more configuration values, from the set of configuration values, based on the one or more configuration values relating to one or more machine learning scores that satisfy a threshold machine learning score; and provide the one or more configuration values to the electromechanical device, wherein the one or more configuration values are part of the electromechanical device configuration for the rehabilitation plan, and wherein said one or more configuration values are provided to the electromechanical device such that the electromechanical device is enabled to implement the electromechanical device configuration for the rehabilitation plan.

26. A tangible, non-transitory computer-readable medium storing instructions that, when executed by a processing device, cause the processing device to:
receive user data relating to a user capable of operating the electromechanical device as part of a prehabilitation procedure, wherein the user data comprises health history data relating to health indicators of the user;
receive treatment data relating to a set of treatment plans and outcomes, wherein the set of treatment plans is capable of being offered to the user;
generate a prehabilitation plan by using a machine learning model to process the user data and the treatment data, wherein the prehabilitation plan includes at least one exercise session comprising one or more exercises to be performed on the electromechanical device;
enable the prehabilitation plan to be distally accessible by one or more user portals;
select, for the electromechanical device, an electromechanical device configuration that enables the one or more exercises of the prehabilitation plan to be performed by the user, wherein the electromechanical device configuration enables the one or more exercises to be performed to improve performance of an area of the user's body; and
enable the electromechanical device to implement the electromechanical device configuration by providing the electromechanical device configuration to the electromechanical device.

27. The tangible, non-transitory computer-readable medium of claim 26, wherein the treatment data comprises treatment plan data relating to the set of treatment plans and treatment outcome data relating to outcomes of the set of treatment plans.

28. The tangible, non-transitory computer-readable medium of claim 26, wherein the instructions, that cause the processing device to generate the prehabilitation plan, cause the processing device to:
provide the user data and the treatment data as inputs to the machine learning model such that the machine learning model is configured to generate machine learning scores for electromechanical device configurations capable of being selected for the prehabilitation plan, wherein the machine learning scores relate to probabilities of a given device configuration being suitable for a given application or applications for the user.

29. The tangible, non-transitory computer-readable medium of claim 28, wherein, based on the selected device configuration corresponding to a threshold probability of improving the performance of the area of the user's body affected, the selected electromechanical device is suitable for the given user application or applications.

30. The tangible, non-transitory computer-readable medium of claim 28, wherein, based on the selected device configuration corresponding to a threshold probability of preventing a health-related event from occurring that affects the user's body, the selected electromechanical device configuration is suitable for the given application or applications for the user.

\* \* \* \* \*